United States Patent [19]

Harrison et al.

[11] Patent Number: 5,369,121
[45] Date of Patent: Nov. 29, 1994

[54] ARTHROPODICIDAL PYRAZOLINES, PYRAZOLIDINES AND HYDRAZINES

[75] Inventors: Charles R. Harrison, Newark; George P. Lahm, Wilmington, both of Del.

[73] Assignee: E. I. Du Pont de Nemours and Company, Wilmington, Del.

[21] Appl. No.: 917,073

[22] PCT Filed: Jan. 8, 1991

[86] PCT No.: PCT/US91/00013

§ 371 Date: Jul. 31, 1992

§ 102(e) Date: Jul. 31, 1992

Related U.S. Application Data

[63] Continuation-in-part of Ser. No. 472,901, Jan. 31, 1990, abandoned, and a continuation-in-part of Ser. No. 473,795, Feb. 2, 1990, abandoned.

[51] Int. Cl.$^5$ .................. A01N 43/56; A01N 43/90; C07D 231/54; C07D 471/04
[52] U.S. Cl. .................. 514/403; 548/359.5
[58] Field of Search .......... 548/359.5, 379.4; 514/408, 403

[56] References Cited

U.S. PATENT DOCUMENTS

| | | | |
|---|---|---|---|
| 4,070,365 | 1/1978 | van Daalen et al. | 548/379 |
| 4,572,914 | 2/1986 | van Hes et al. | 514/403 |
| 4,663,341 | 5/1987 | Jacobson | 514/403 |
| 4,863,947 | 9/1989 | Jacobson | 514/403 |
| 4,960,784 | 10/1990 | Lahm | 514/403 |
| 5,091,405 | 2/1992 | Stevenson | 514/403 |
| 5,109,014 | 4/1992 | Jacobson | 514/403 |
| 5,276,039 | 1/1994 | Lahm et al. | 514/287 |

FOREIGN PATENT DOCUMENTS

| | | | |
|---|---|---|---|
| 0021506 | 6/1980 | European Pat. Off. | C07D 231/06 |
| 0153127 | 8/1985 | European Pat. Off. | C07D 231/06 |
| 0267869 | 11/1987 | European Pat. Off. | C07D 231/06 |
| 0286346 | 10/1988 | European Pat. Off. | C07D 231/54 |
| 2304584 | 8/1973 | Germany | C07D 401/04 |
| WO88/06583 | 9/1988 | WIPO | C07D 231/06 |
| 6583 | 9/1988 | WIPO . | |
| WO88/07994 | 10/1988 | WIPO | C07D 231/54 |
| 3369 | 4/1990 | WIPO . | |

OTHER PUBLICATIONS

J. Org. Chem., 43(9):1664–1671 (1978).
J. Org. Chem., 46:1402–1409 (1981).
J. Org. Chem., 42(8):1389–1392 (1977).
J. Chem. Soc., Perkin I., pp. 2245–2249 (1981).

Primary Examiner—Joseph Paul Brust
Assistant Examiner—Mary Susan H. Gabilan
Attorney, Agent, or Firm—James A. Costello

[57] ABSTRACT

Compounds of Formula I

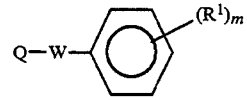

wherein Q, W, R$^1$ and m are as defined in the text; these compounds being useful in controlling agronomic and nonagronomic arthropods.

7 Claims, No Drawings

ARTHROPODICIDAL PYRAZOLINES, PYRAZOLIDINES AND HYDRAZINES

CROSS-REFERENCE TO RELATED APPLICATIONS

This is a continuation-in-part of U.S. applications bearing Ser. Nos. 07/472,901 filed on Jan. 31, 1990 and continuation-in-part 07/473,795 filed on Feb. 2, 1990, both now abandoned.

BACKGROUND OF THE INVENTION

1. Field of the Invention

This invention concerns arthropodicidal pyrazolines, pyrazolidines and hydrazines and their use to control arthropods.

2. State of the Art

These publications disclose insecticidal pyrazolines: WO 88/07,994, EPA 330,678, U.S. Pat. No. 4,070,365, and EPA 153,127. They are, however, not especially relevant to the class of pyrazolines described herein. These publications disclose pyrazolidines: *J. Org. Chem.*, 1987, 52, 2277 and *Chem. Soc. Japan*, 1982, 55, 2450.

SUMMARY OF THE INVENTION

The invention pertains to compounds of Formula I including all geometric and stereoisomers, agriculturally suitable salts thereof, agricultural compositions containing them and their use for the control of arthropods in both agronomic and nonagronomic environments. The compounds are:

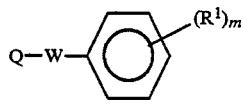

wherein:

Q is attached to the carbon terminus of W and is selected from the group

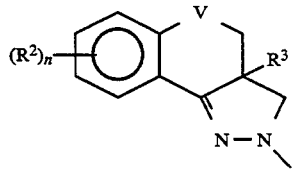 Q-1

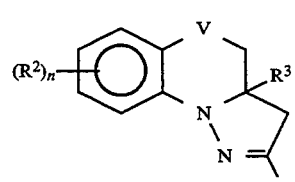 Q-2

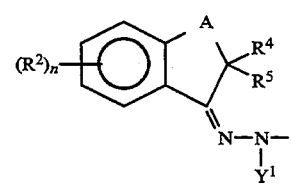 Q-3

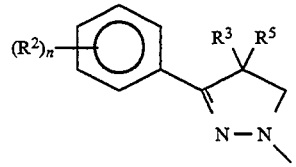 Q-4

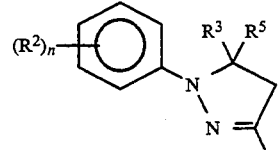 Q-5

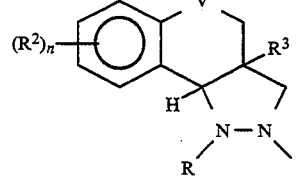 Q-6

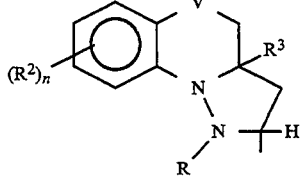 Q-7

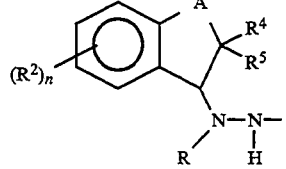 Q-8

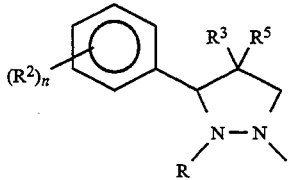 Q-9 and

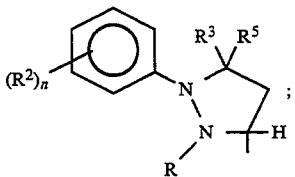 Q-10

W is selected from the group

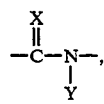 W-1

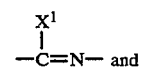 W-2 and

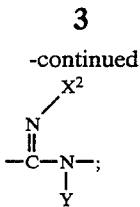

wherein:
V is selected from the group O, S, $NR^{11}$ and $CH_2$ optionally substituted with 1-2 $CH_3$;
A is selected from the group O, S, $NR^{11}$, $CH_2$, $CH_2$ optionally substituted with a group selected from $C_1$-$C_4$ alkyl and $CH_2$ optionally substituted with phenyl which is optionally substituted with $R^{12}$;
X is selected from the group O and S;
$X^1$ is selected from the group Cl, Br, $OR^6$, $SR^6$, and $NR^6R^7$;
$X^2$ is selected from the group $R^6$, OH, $OR^6$, CN, $SO_2R^6$, $OC(O)NR^7R^8$, $OC(O)OCH_3$, $NR^7R^8$, phenyl optionally substituted with $R^9$ and $SO_2Ph$ optionally substituted with $R^9$;
Y is selected from the group H, $C_1$-$C_6$ alkyl, benzyl, $C_2$-$C_6$ alkoxyalkyl, CHO, $C_2$-$C_6$ alkylcarbonyl, $C_2$-$C_6$ alkoxycarbonyl, $C_2$-$C_6$ haloalkylcarbonyl, $C_1$-$C_6$ alkylthio, $C_1$-$C_6$ haloalkylthio, phenylthio, $R^{17}OC(O)N(R)^{18}S$ and $SN(R^{19})R^{20}$;
$Y^1$ is selected from the group H, $C_1$-$C_3$ alkyl, $C_2$-$C_3$ alkylcarbonyl and $C_2$-$C_3$ alkoxycarbonyl;
R is selected from the group H, $C_1$-$C_4$ alkyl, $C_1$-$C_4$ haloalkyl, $C_2$-$C_4$ alkoxycarbonyl, $C_2$-$C_4$ haloalkylcarbonyl, $C_2$-$C_4$ alkoxycarbonyl, $C_2$-$C_4$ haloalkoxycarbonyl, $C_2$-$C_5$ alkylcarbamoyl, $C_3$-$C_6$ cycloalkyl, $C_3$-$C_6$ halocycloalkyl, $C_4$-$C_7$ alkylcycloalkyl, $C_4$-$C_7$ haloalkylcycloalkyl, $C_1$-$C_4$ alkylsulfonyl, $C_1$-$C_4$ haloalkylsulfonyl and $SO_2Ph$;
$R^1$, $R^2$, $R^9$, $R^{10}$, $R^{12}$, $R^{14}$, $R^{15}$ and $R^{16}$ are each independently selected from the group H, halogen, CN, $C_1$-$C_3$ haloalkyl, $C_1$-$C_3$ haloalkoxy and $OS(O)_2$-$C_1$-$C_3$ haloalkyl;
$R^3$ is selected from the group H, $C_1$-$C_6$ alkyl, $C_2$-$C_6$ alkenyl, $CO_2R^{13}$ and phenyl optionally substituted by $(R^{14})_p$;
$R^4$ is selected from the group H, $C_1$-$C_6$ alkyl, $C_2$-$C_6$ alkenyl and phenyl optionally substituted with $(R^{16})_s$;
$R^5$ is selected from the group H and $C_1$-$C_4$ alkyl;
$R^6$ is selected from the group $C_1$-$C_3$ alkyl, benzyl optionally substituted with $R^9$, $C_2$-$C_4$ alkenyl, $C_2$-$C_4$ alkynyl, $C_1$-$C_3$ haloalkyl, $C_2$-$C_4$ haloalkenyl, $C_2$-$C_3$ alkoxycarbonyl, $C_3$-$C_6$ cycloalkyl and $C_2$-$C_3$ alkylcarbonyl; or $R^6$ is $C_1$-$C_3$ alkyl substituted with a member selected from the group $OCH_3$, $OCH_2CH_3$, $NO_2$, CN, $CO_2CH_3$, $CO_2CH_2CH_3$, $SCH_3$ and $SCH_2CH_3$;
$R^7$ is selected from the group H, $C_1$-$C_4$ alkyl, $C_1$-$C_4$ haloalkyl, $C_2$-$C_4$ alkoxycarbonyl, phenyl optionally substituted with $R^{10}$ and pyridyl optionally substituted with $R^{10}$;
$R^6$ and $R^7$ can be taken together as $CH_2CH_2CH_2CH_2$, $CH_2CH_2CH_2CH_2CH_2$, or $CH_2CH_2OCH_2CH_2$ when $X^1$ is $NR^6R^7$;
$R^8$ is selected from the group H and $C_1$-$C_4$ alkyl;
$R^7$ and $R^8$ can be taken together as $CH_2CH_2CH_2CH_2$, $CH_2CH_2CH_2CH_2CH_2$, or $CH_2CH_2OCH_2CH_2$;
$R^{11}$ is selected from the group H, $C_1$-$C_4$ alkyl, $C_1$-$C_4$ haloalkyl, $C_1$-$C_3$ alkylsulfonyl, $C_2$-$C_5$ alkylcarbamoyl, $C_2$-$C_3$ alkylcarbonyl, $C_2$-$C_3$ haloalkylcarbonyl, $C_2$-$C_4$ alkenyl, $C_2$-$C_4$ haloalkenyl, $C_2$-$C_4$ alkoxycarbonyl, phenyl optionally substituted with $R^{15}$ and benzyl optionally substituted with $R^{15}$;
$R^{13}$ is selected from the group H and $C_1$-$C_3$ alkyl;
$R^{17}$ is selected from $C_1$-$C_6$ alkyl;
$R^{18}$ is selected from $C_1$-$C_6$ alkyl;
$R^{19}$ and $R^{20}$ are independently $C_1$-$C_4$ alkyl; or
$R^{19}$ and $R^{20}$ can be taken together as $CH_2CH_2CH_2CH_2CH_2$ or $CH_2CH_2OCH_2CH_2$;
m is 1 or 2;
n is 1 or 2;
p is 1 or 2; and
s is 1 or 2;
i) wherein when Q is Q-4 and W is W-3 then $R^5$ is H and $R^3$ is selected from the group H, $C_1$-$C_6$ alkyl and phenyl substituted by $(R^{14})_p$;
ii) wherein when Q is Q-1 to Q-5, then W is W-2 or W-3.

In the above definitions, the term "alkyl", used either alone or in compounds words such as "alkylthio" or "haloalkyl", denotes straight chain or branched alkyl such as methyl, ethyl, n-propyl, isopropyl or the different butyl, pentyl, hexyl isomers. Alkoxy denotes methoxy, ethoxy, n-propyloxy, isopropyloxy and the different butoxy, pentoxy or hexoxy isomers. Alkenyl denotes straight chain or branched alkenes such as vinyl, 1-propenyl, 2-propenyl, 3-propenyl and the different butenyl, pentenyl and hexenyl isomers. Alkynyl denotes straight chain or branched alkynes such as ethynyl, 1-propynyl, 3-propynyl and the different butynyl, pentynyl and hexynyl isomers. Alkylthio denotes methylthio, ethylthio and the different propylthio, butylthio, pentylthio and hexylthio isomers. Alkylsulfinyl, alkylsulfonyl, alkylamino, and the like, are defined analogously to the above examples. Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl can be partially or fully substituted with halogen atoms, which can be the same or different. Examples of haloalkyl include $CH_2CH_2F$, $CF_2CF_2H$ and $CH_2CHFCl$. The terms "halocyclo- alkyl", "haloalkenyl" and "haloalkynyl" are defined analogously to the term "haloalkyl".

The total number of carbon atoms in a substituent group is indicated by the "$C_i$-$C_j$" prefix where i and j are numbers from 1 to 8. For example, $C_1$-$C_3$ alkylsulfonyl designates methylsulfonyl through propylsulfonyl; $C_2$ alkoxyalkoxy designates $OCH_2OCH_3$; $C_4$ alkoxyalkoxy designates the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl designates $CH_2CH$ and $C_3$ cyanoalkyl designates $CH_2CH_2CN$ and $CH(CN)CH_3$; $C_2$ alkylcarbonyl designates $C(O)CH_3$ and $C_4$ alkylcarbonyl includes $C(O)CH_2CH_2CH_3$ and $C(O)CH(CH_3)_2$; and as a final example, $C_3$ alkoxycarbonylalkyl designates $CH_2CO_2CH_3$ and $C_4$ alkoxycarbonylalkyl includes $CH_2CH_2CO_2CH_3$, $CH_2CO_2CH_2CH_3$ and $CH(CH_3)CO_2CH_3$.

Preferred Compounds A are those compounds of Formula I wherein:
X is O;
$X^1$ is selected from the group Cl, $SR^6$, $N(CH_3)_2$ and $OR^6$;
$X^2$ is selected from the group CN, $OR^6$, OH and $N(CH_3)_2$;

V is selected from the group $CH_2$ and O;
A is selected from the group $CH_2$ and O;
R is H;
$R^1$, $R^2$, $R^{14}$ and $R^{16}$ are each independently selected from the group H, F, Cl, Br, $CF_3$, $OCF_3$, $OCF_2H$, $OCH_2CF_3$ and $OSO_2CF_3$;
$R^3$ is selected from the group $CO_2CH_3$, $CH(CH_3)_2$, $CH_3$ and phenyl optionally substituted with $R^{14}$;
$R^4$ is selected from the group $CH_3$, $CH(CH_3)_2$ and phenyl optionally substituted with $R^{16}$;
$R^5$ is selected from the group H and $CH_3$;
$R^6$ is $C_1$-$C_2$ alkyl;
$R^{11}$ is selected from the group H, $CH_3$, $SO_2CH_3$, $C(O)CH_3$, $C(O)NHCH_3$ and $CO_2CH_3$;
Y is selected from the group H, $C(O)CH_3$, $CH_3$ and $CO_2CH_3$; and
m and n are 1.

Preferred Compounds B are those compounds of Preferred A wherein Q is Q-1 and W is W-2.
Preferred Compounds C are those compounds of Preferred A wherein Q is Q-3 and W is W-2.
Preferred Compounds D are those compounds of Preferred A wherein Q is Q-1 and W is W-3.
Preferred Compounds E are those compounds of Preferred A wherein Q is Q-3 and W is W-3.
Preferred Compounds F are those compounds of Preferred A wherein Q is Q-6 and W is W-1.
Preferred Compounds G are those compounds of Preferred A wherein Q is Q-8 and W is W-1.

DETAILS OF THE INVENTION

Compounds of Formula I can be prepared as described in Schemes 1 through 24 and the previously defined variables will remain as defined unless otherwise noted.

Compounds of the Formula I (Q-1, W-2 or W-3) can be prepared by the reaction of imidoylhalides of the Formula I (Q-1, W-2) with sulfur, oxygen and nitrogen nucleophiles of the Formula III as illustrated in Scheme 1. Typical reactions involve the combination of equimolar amounts of I (Q-1, W-2) and III in the presence of a base such as an alkali metal, tertiary amine, metal hydride and the like in conventional organic solvents, including ether, tetrahydrofuran 1,2-dimethoxyethane, methylene chloride, chloroform, N,N-dimethylformamide and dimethylsulfoxide. The reaction can be conducted at temperatures ranging from $-20°$ C. to $100°$ C. with temperatures in the range of $-10°$ C. to $30°$ C. generally being preferred. One skilled in the art should recognize that reactions of this general type can be extended to other nucleophilic reagents.

SCHEME 1

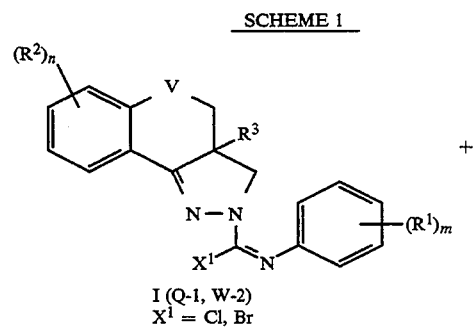

I (Q-1, W-2)
$X^1$ = Cl, Br

-continued
SCHEME 1

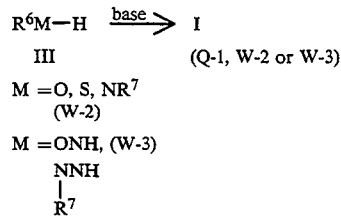

Compounds of the Formula I (Q-1, W-2) can be prepared by the reaction of Formula IV compound with an appropriate halogenating agent such as phosphorous trichloride, phosphorous pentachloride, phosphorous tribromide, phosphorous pentabromide, thionyl chloride, sulfuryl chloride, triphenyl phosphine and carbon tetrachloride (Wolkoff, Can. J. Chem., 1975, 53, 1333) and the like (see Fieser and Fieser, Reagents for Organic Synthesis, Vol. I, 1967) as illustrated in Scheme 2. Typical reactions involve the combination of Formula IV compounds with an excess of the halogenating agent ranging from 1.1 to 10 equivalents, with 2 to 4 equivalents being preferred. The reaction can be conducted in the absence of a solvent or in the presence of a conventional organic solvent such as benzene, toluene, xylene, chloroform, methylene chloride, hexane and the like. The reaction temperature can range from $-10°$ C. to $200°$ C. with $35°$ C. to $100°$ C. being preferred. The reaction is generally complete after 24 hours.

SCHEME 2

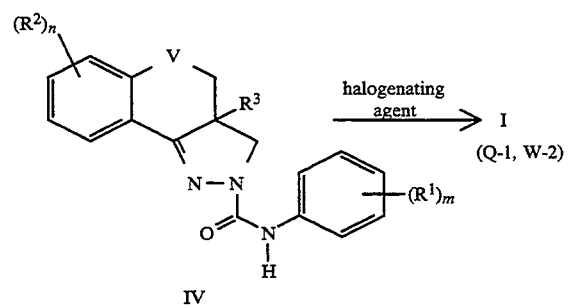

The preparation of Formula IV compounds is known. Compounds of Formula I (Q-1, W-2), when $X^1$ is equal to $R^6$-S, can be prepared by the reaction of compounds of Formula V with an electrophile of Formula VI in the presence of a suitable base, as illustrated in Scheme 3. Typical reactions involve the combination of equimolar amounts of Formula V compounds and the appropriate electrophile of Formula VI. A base such as an alkali metal, tertiary amine or metal hydride can be used.

SCHEME 3

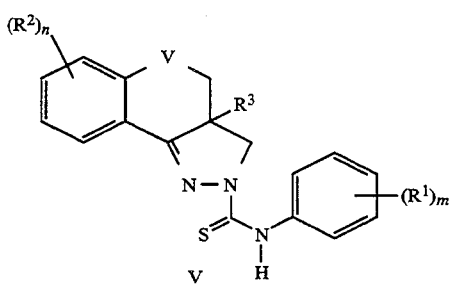

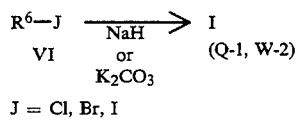

J = Cl, Br, I

Preparation of compounds of Formula V is known. Compounds of the Formula I (Q-2, W-2 or W-3) can be prepared from Formula I (Q-2, W-2) derivatives in an analogous fashion as that described for the preparation of Formula I (Q-1, W-2) compounds. Scheme 4 illustrates this method.

SCHEME 4

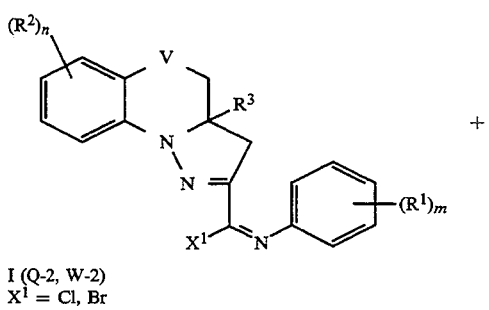

I (Q-2, W-2)
X¹ = Cl, Br

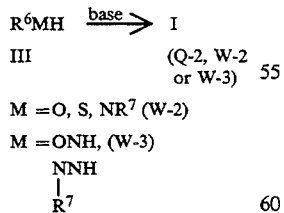

M = O, S, NR⁷ (W-2)

M = ONH, (W-3)
    |
   NNH
    |
    R⁷

Formula I (Q-2, W-2) compounds can be prepared from Formula VII compounds in an analogous fashion as that described for Formula I (Q-1, W-2) compounds. Scheme 5 illustrates this method.

SCHEME 5

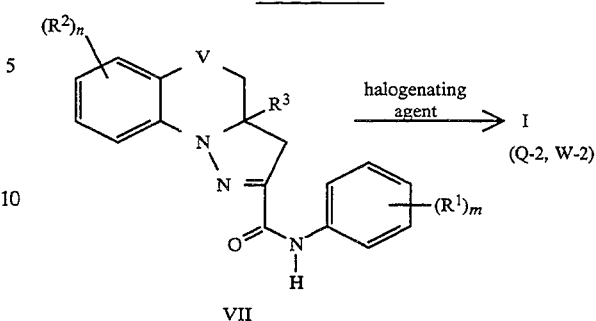

Compounds of Formula VII can be prepared by the reaction of the acid chloride VIII with a substituted aniline of Formula IX in equimolar proportions in the presence of an excess of acid scavenger, such as tertiary alkylamines or pyridines, but not limited to these, in an aprotic organic solvent such as ether, tetrahydrofuran, chloroform, methylene chloride, benzene and/or toluene. Scheme 6 illustrates this transformation.

SCHEME 6

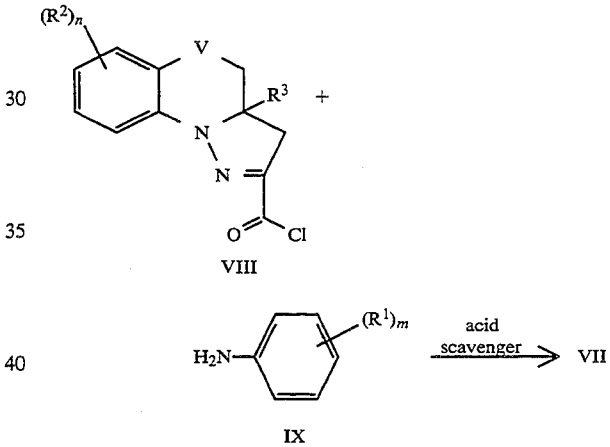

Compounds of the Formula VIII can be prepared from compounds of the Formula X through conventional methodology generally used for the conversion of esters to their corresponding acid chlorides as illustrated in Scheme 7.

SCHEME 7

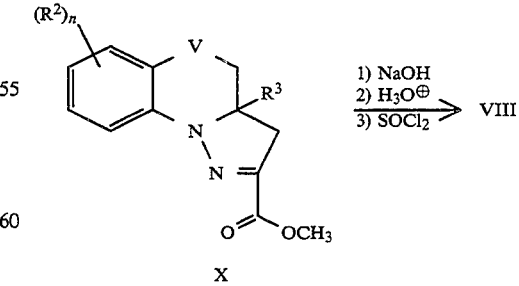

Compounds of Formula X can be obtained by the intramolecular dipolar cycloaddition reaction of nitrile-imines, generated from substituted phenylhydrazones of Formula XI (Scheme 8). The presence of an acid acceptor (generally an amine base, for example, triethylamine) is necessary for the formation of the nitrile-imine. Suitable solvents include, but are not restricted to benzene, toluene, 1,2-dichloroethane, chloroform, and tetrahydrofuran. The reaction can be carried out at temperatures ranging from 20° to 120° C with the relative reactivity of the alkene moiety governing the required temperature.

SCHEME 8

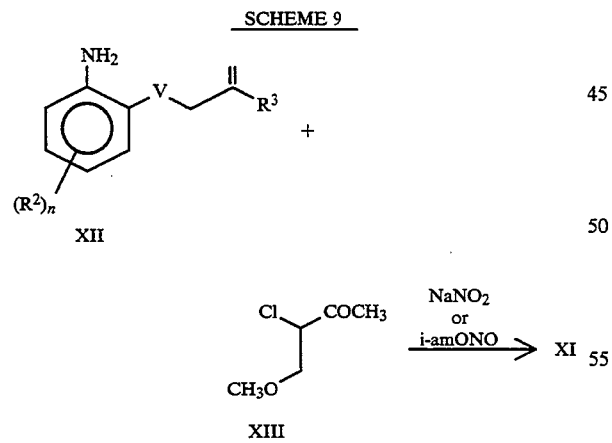

XI

The required hydrazones of Formula XI can be synthesized by the Japp-Klingemann reaction (Scheme 9). The coupling of diazonium salts with active methylene compounds is known. The more specific coupling of chloroacetoacetic acid derivatives of Formula XIII with diazotized anilines of Formula XII containing alkenyl substitutents is described in *J. Org. Chem.*, 43, 1664 (1978) and *J. Org. Chem.*, 46, 1402 (1981). A similar process for this type of aniline is described in *J. Org. Chem.*, 42, 1389(1977), and *J. Chem. Soc., Perkin I*, 2245 (1981).

SCHEME 9

Compounds of the Formula XII can be prepared by conventional methods known to one skilled in the art.

The Formula I (Q-3, W-3) compounds can be prepared from Formula I (Q-3, W-2) derivatives in an analogous fashion as that described for the preparation of Formula I (Q-1, W-3) compounds. Scheme 10 illustrates this method.

SCHEME 10

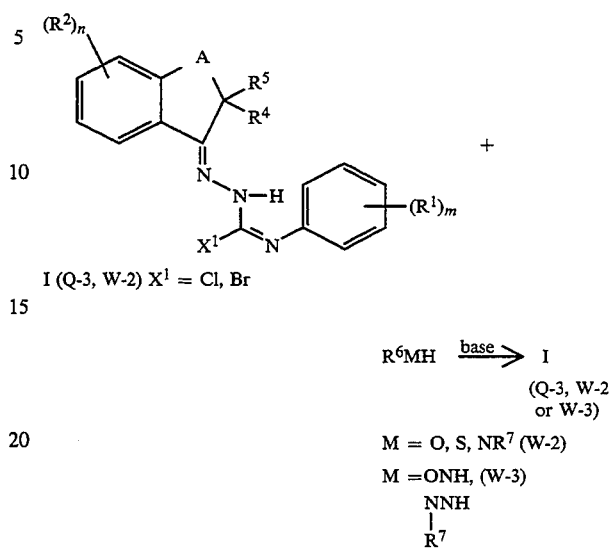

I (Q-3, W-2) $X^1$ = Cl, Br $R^6MH \xrightarrow{\text{base}} I$ (Q-3, W-2 or W-3)

$M = O, S, NR^7$ (W-2)

$M = ONH$, (W-3)

$\quad\quad NNH$
$\quad\quad\ \ |$
$\quad\quad\ \ R^7$

The compounds of the Formula I (Q-3, W-2) can be prepared from Formula XIV derivatives in an analogous fashion as that described for Formula I (Q-1, W-2) compounds. Scheme 11 illustrates this method.

SCHEME 11

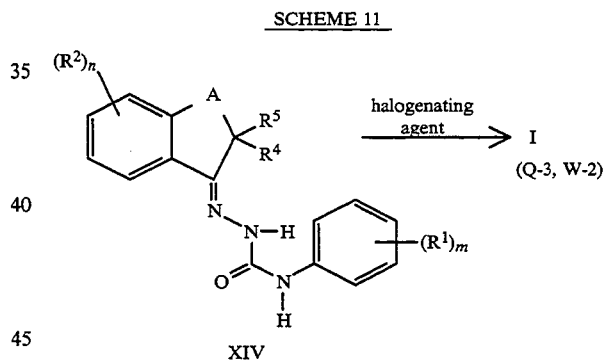

XIV

The compounds of Formula XIV can be prepared by the reaction of hydrazones of Formula XV with an aryl isocyanate of Formula XVI (Scheme 12). Typical reactions involve combination of equimolar amounts of XV and XVI in a suitable solvent at temperatures generally in the range of −10° C. to 100° C. Although the reaction can be run neat, a solvent is generally preferred. Suitable solvents typically have sufficient polarity to effect solution of the Formula XV hydrazones including, but not limited to, ethers such as diethyl ether, tetrahydrofuran and dioxane; halogenated hydrocarbons such as methylene chloride, chloroform and carbon tetrachloride; aromatic hydrocarbons such as benzene, toluene and xylene; esters such as ethyl acetate and polar aprotic solvents such as dimethylformamide and dimethylacetamide.

SCHEME 12

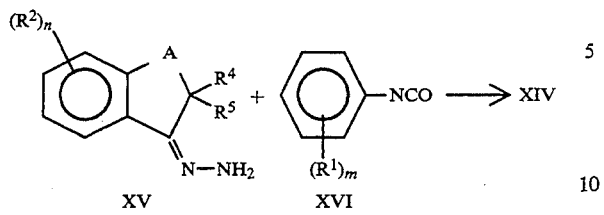

The hydrazones of Formula XV can be obtained by processes known in the art involving condensation of a ketone of Formula XVII with hydrazine (Scheme 13). This reaction is typically conducted with equimolar amounts of XVII and hydrazine although greater than stoichiometric amounts of hydrazine can be used. Suitable solvents include the alcohols such as methanol, ethanol, propanol, butanol and the like at temperatures in the range of 0° to 150° C., with the reflux temperature of the solvent generally being a convenient reaction temperature. Acid catalysis can also be useful, particularly for some of the more sterically hindered Formula XVII compounds. Typical acid catalysts include sulfuric, hydrochloric and p-toluene sulfonic acid.

SCHEME 13

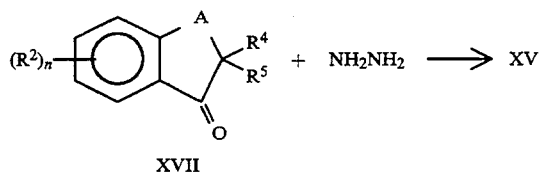

The starting ketones of Formula XVII are known in the art or can be obtained by methods analogous to known procedures. Those skilled in the art will recognize the Formula XVII compounds to include indanones, tetralones, chromanones, thiochromanones, benzofuran-3-ones, thiobenzofuran-3-ones, isochromanones and others.

The compounds of Formula I (Q-4, W-2 or W-3) can be prepared from Formula I (Q-4, W-2) derivatives in an analogous fashion as that described for the preparation of Formula I (Q-1, W-2 or W-3) compounds. Scheme 14 illustrates this method.

SCHEME 14

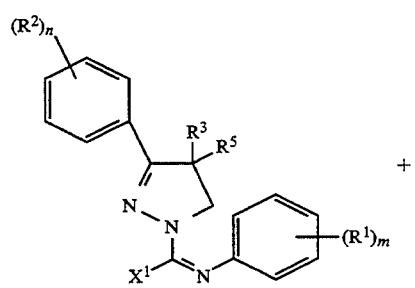

I (Q-4, W-2) X$^1$ = Cl, Br

-continued
SCHEME 14

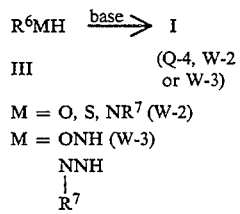

M = O, S, NR$^7$ (W-2)
M = ONH (W-3)
$\phantom{M =}$ NNH
$\phantom{M = ON}|$
$\phantom{M = ONH}$R$^7$ Formula I (Q-4, W-2 or W-3) compounds can be prepared from Formula XVIII derivatives in an analogous fashion as that described for Formula I (Q-1, W-2) compounds. Scheme 15 illustrates this method.

SCHEME 15

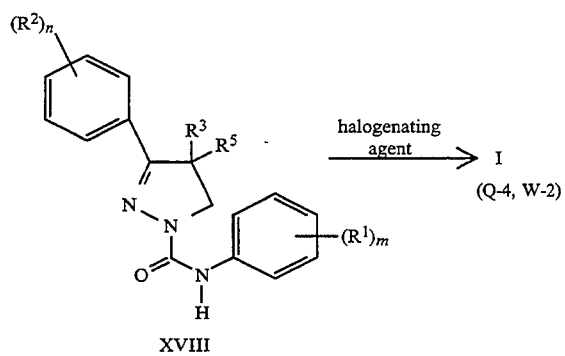

The preparation of compounds of Formula XVIII is known. The Formula I (Q-5, W-2 or W-3) compounds can be prepared from Formula I (Q-5, W-2) derivatives in an analogous fashion as that described for the preparation of Formula I (Q-1, W-2 or W-3) compounds. Scheme 16 illustrates this method.

SCHEME 16

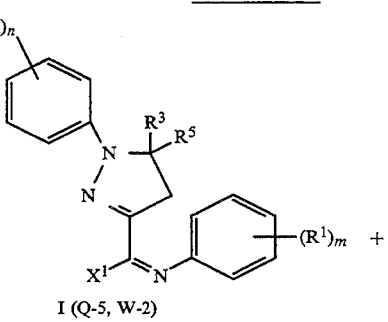

I (Q-5, W-2)

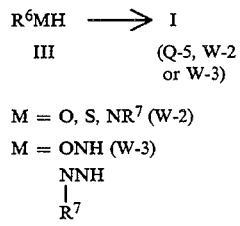

M = O, S, NR$^7$ (W-2)
M = ONH (W-3)
$\phantom{M =}$ NNH
$\phantom{M = ON}|$
$\phantom{M = ONH}$R$^7$ Formula I (Q-5, W-2) compounds can be prepared from Formula XIX derivatives in an analogous fashion as that described for Formula I (Q-1, W-2) compounds. Scheme 17 illustrates this method.

SCHEME 17

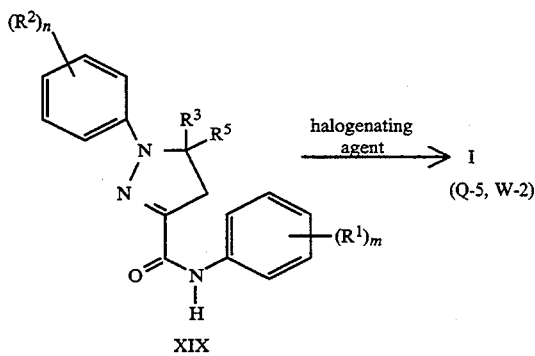

Compounds of Formula I (Q-6, W-1) wherein R is equal to H can be prepared by the reaction of aryl isocyanates of Formula XVI with substituted pyrazolidines of Formula XXI as illustrated in Scheme 18. Typical reactions involve the combination of equimolar amounts of XVI and XXI in conventional organic solvents including ethyl acetate, ether, tetrahydrofuran, methylene chloride, chloroform, benzene and toluene but not restricted to these. The reaction can be conducted at temperatures ranging from −20° C. to 100° C. with temperatures in the range of −10° C. to 30° C. generally preferred.

SCHEME 18

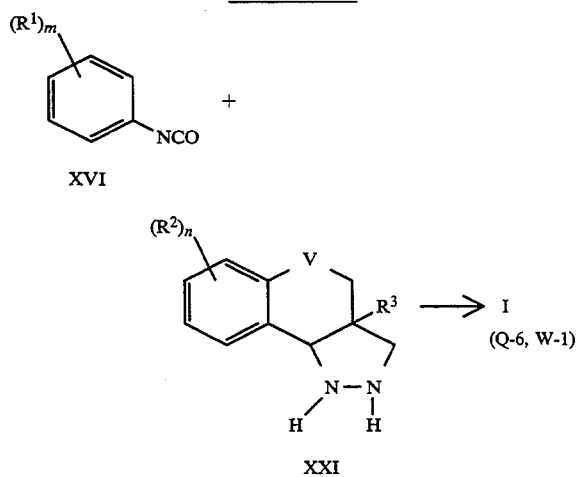

Compounds of Formula XXI can be prepared by the reaction of hydrazine dihydrochloride or hydrazine sulfate with compounds of Formula XXII as illustrated in Scheme 19. Modification of the procedure described in Bull. Chem. Soc. Jap., 1982, 55, 2450, and J. Org. Chem., 1987, 52, 2277, can be applied to the synthesis of compounds of the Formula XXI. Typical reactions involved the addition of an excess of hydrazine dihydrochloride or hydrazine sulfate, ranging from 1.1 to 20 equivalents with 5 to 15 equivalents being preferred, to one equivalent of a compound of Formula XXII in an alcohol/water solvent mixture ranging from 1 to 99% alcohol with 90% to 95% alcohol being preferred. Typical alcoholic solvents include methanol, ethanol, n-propanol, n-butanol, tert-butanol and the like. The reaction can be conducted at temperatures ranging from −20° C. to 140° C. with temperatures in the range of 20° C. to 80° C. being preferred. The reaction is usually complete within 24 hours.

SCHEME 19

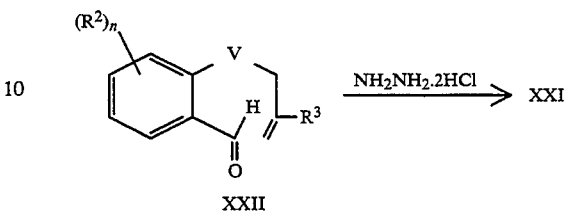

Substituted benzaldehydes of Formula XXII can be prepared utilizing known methods or obvious modifications thereof by one skilled in the art.

Compounds of formula I (Q-6, W-1) where R is not equal to H can be prepared by the reaction of Formula I (Q-6, W-1) compounds where R is equal to H with a variety of electrophiles. For example, these electrophiles include, but are not limited to, alkyl halides, alkyl and aryl isocyanates, acyl halides, sulfonyl halides and alkyl chlorocarbonates. Reactions to prepare Formula I (Q-6, W-1) compounds where R is not equal to H can be conducted through standard procedures known to those skilled in the art. For example, the reaction of Formula I (Q-6, W-1) compounds where R is equal to H with methyl isocyanate (Scheme 20) can be conducted by reaction of equal molar amounts of the reactants in an inert solvent such as, but not limited to, ether, tetrahydrofuran, dimethoxyethane, ethyl acetate, methylene chloride and chloroform, in the presence of an acid scavenger such as tertiary alkylamines, substituted pyridines, alkali metals, and the like.

SCHEME 20

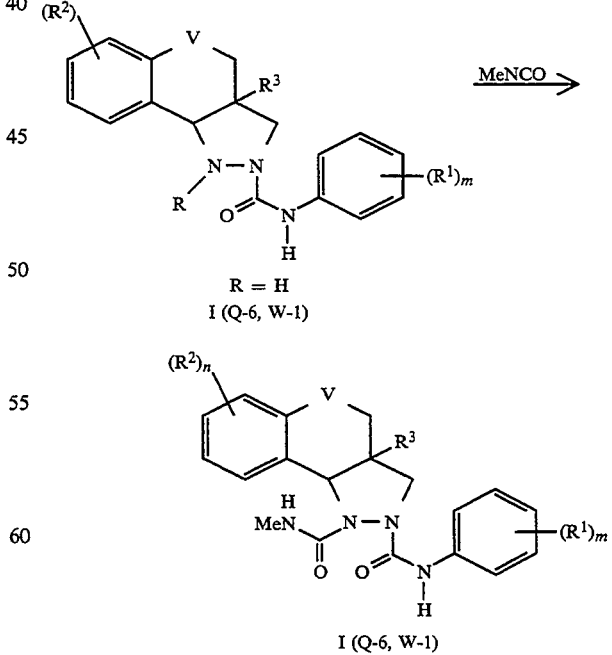

Compounds of Formula I (Q-7, W-1) can be prepared by the reaction of tri- and tetravalent metal species such as titanium, silicon, tin and the like in combination with a reducing agent such as sodium, lithium, or zinc borohydride, lithium aluminum hydride and the like with compounds of Formula VII as illustrated in Scheme 21. Literature precedent for analogous reactions can be found in *J. Org. Chem.*, 1987, 54, 3750, and *Synthesis*, 1980, 695. Typical reactions involve the addition of 1 equivalent of a compound of Formula VII to a solution of 1.1 to 4 equivalents of titanium tetrachloride, with 1.5 to 2.5 equivalents being preferred, and 2.1 to 6 equivalents of sodium borohydride with 3.5–4.5 equivalents being preferred.

Conventional organic solvents such as ether, tetrahydrofuran, dimethoxyethane, methylene chloride and chloroform can be used with 1,2-dimethoxyethane being preferred. The reaction can be conducted at temperatures ranging from −70° C. to 50° C. with −10° C. to 30° C. being preferred. The reaction time can be 0.1 hour to 48 hours with 2 to 4 hours being preferred.

SCHEME 21

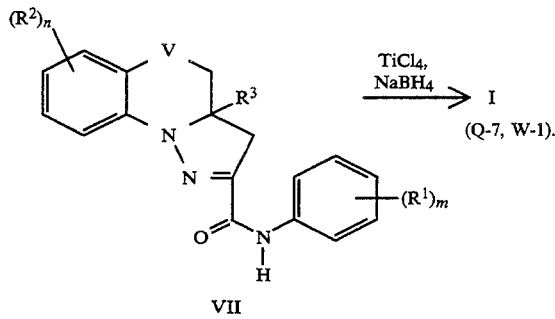

Formula I (Q-7, W-1) compounds where R is not equal to H can be prepared in the same fashion as described for Formula I (Q-7, W-1) compounds where R is not equal to H. Compounds of Formula VII can be prepared as described with respect to Scheme 5.

Compounds of Formula I (Q-8, W-1) can be prepared by a titanium tetrachloride/sodium borohydride reduction of Formula XIV analogs in a similar fashion as described for Formula I (Q-7, W-1) compounds. Scheme 22 illustrates the method utilized.

SCHEME 22

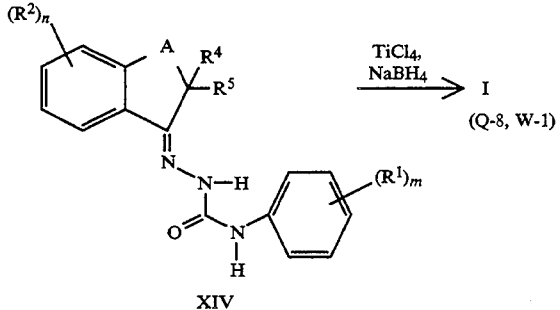

The compounds of Formula XIV can be prepared as described with respect to Scheme 11. The compounds represented by Formula I (Q-9, W-1) can be prepared by a titanium tetrachloride/sodium borohydride reduction of Formula XVII analogs in a similar fashion as described for Formula I (Q-7, W-1) compounds. Scheme 23 illustrates this method.

SCHEME 23

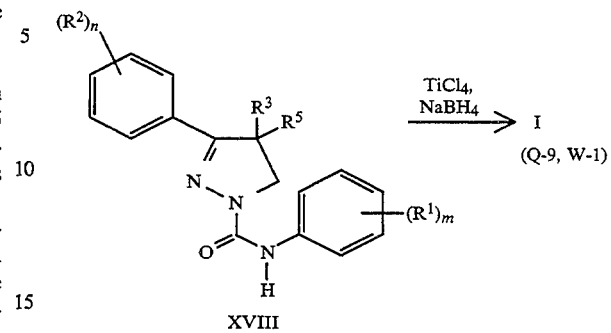

The preparation of the compounds represented by Formula XVIII is known. The compounds represented by Formula I (Q-10, W-1) can be prepared by a titanium tetrachloride/sodium borohydride reduction of Formula XIX analogs in a similar fashion as described for Formula I (Q-7, W-1) compounds. Scheme 24 illustrates this method.

SCHEME 24

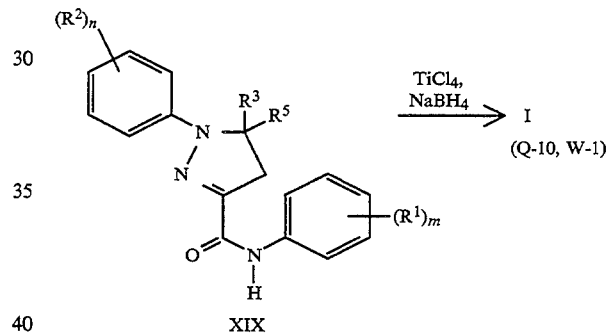

The preparation of the compounds represented by Formula XIX is known. The Formula I (Q-6, Q-7, Q-8, Q-9, Q-10, W-1) compounds where Y is other than H, can be prepared via the TiCl$_4$/NaBH$_4$ reductive methods described previously.

The preparation of compounds of Formula XIX is a known intramolecular dipolar cycloaddition reaction to generate the pyrazoline nucleus. Compounds of Formulas I where Y$^1$ and Y are other than H can be prepared by conventional alkylation, acylation and sulfenylation methods known to one skilled in the art.

The following Examples further illustrate the invention.

EXAMPLE 1

Step A: 4-Chloro-2-(3-methyl-2-methylenebutoxy)-benzaldehyde

To a solution of 8.8 g (0.064 mol) of potassium carbonate in 100 mL of dimethylformamide was added 10.0 g (0.064 mol) of 4-chlorosalicylaldehyde and 12.5 g (0.077 mol) of 2-(bromomethyl)-3-methyl-1-butene. The reaction mixture was heated at 70° C. for 2 hours, cooled to room temperature and poured into 600 mL ice/water. The crude mixture was extracted with ethyl acetate (3×100 mL). The ethyl acetate was washed with water (100 mL) and brine (100 mL), dried over anhydrous magnesium sulfate, filtered and concentrated under reduced pressure to afford 14.0 g of a yellow oil.

200 MHz $^1$H NMR (CDCl$_3$) $\delta$ 1.15 (d, 6H), 2.4 (m, 1H), 4.61 (s, 2H), 5.08 (s, 1H), 5.15 (s, 1H), 6.99 (s, 1H), 7.02 (d, 1H), 7.80 (d, 1H), 10.5 (s, 1H).

IR (neat): 1685 cm$^{-1}$.

Step B: Diethyl [[4-chloro-2-(3-methyl-2-methylenebutoxy)phenyl]methylene]phosphorohydrazidate To a solution of 11.8 g (0.070 mol) of diethyl phosphorohydrazidate in 140 mL ether was added 14.0 g (0.058 mol) of the product obtained in Step A. The reaction was stirred at room temperature for 30 minutes. The resultant precipitate was filtered and washed with ether (50 mL) and dried to afford 15.0 g of a white solid, mp 103° C. to 106° C.

200 MHz $^1$H NMR (CDCl$_3$) $\delta$ 1.15 (d, 6H), 1.35 (t, 6H), 2.45 (m, 1H), 4.2 (m, 4H), 4.52 (s, 2H), 5.06 (s, 1H), 5.10 (s, 1H), 6.9 (m, 3H), 7.80 (d, 1H), 8.1 (s, 1H).

IR (mineral oil): 3140, 1600, 1020 cm$^{-1}$.

Step C: 7-Chloro-2,3,3a,4-tetrahydro-3a-(1-methylethyl)-N-[4-(trifluoromethyl)phenyl][1]benzopyrano[4,3-c]pyrazole-2-carboxamide To a solution of 6.8 g (0.017 mol) of the product obtained in Step B dissolved in 90 mL methylene chloride was added 2.8 g (0.021 mol) of N-chlorosuccinimide. The reaction mixture was stirred at room temperature and 2.7 g (0.026 mol) of triethylamine dissolved in 20 mL methylene chloride was added dropwise over 1 hour. The reaction mixture was extracted with a 5% HCl solution (100 mL) and washed with water (100 mL), dried over anhydrous magnesium sulfate, filtered and concentrated under reduced pressure to afford 6.3 g of a red oil. This oil was taken up in 60 mL of methanol and 4.9 mL of concentrated HCl was added. The reaction mixture was refluxed for 3 hours, cooled and concentrated under reduced pressure. 200 mL of a saturated sodium bicarbonate solution was added and the reaction mixture was extracted with ethyl acetate (3×100 mL). The ethyl acetate was washed with brine (100 mL), dried over anhydrous magnesium sulfate and filtered into a flask where 3.0 g (0.016 mol) of $\alpha,\alpha,\alpha$-trifluoro-p-tolylisocyanate was added. The reaction mixture was stirred at room temperature for 30 minutes, concentrated under reduced pressure to afford a yellow solid. The yellow solid was chromatographed on silica gel using tetrahydrofuran (20%) and hexanes (80%) as the eluent which afforded 6.4 g of a white solid, mp 150° C. to 152° C. 200 MHz $^1$H NMR (CDCl$_3$) $\delta$ 0.82 (d, 3H), 1.1 (d, 3H), 2.11 (m, 1H), 3.45 (d, 1H), 4.10 (d, 1H), 4.15 (d, 1H), 4.63 (d, 1H), 6.98 (s, 1H), 7.0 (d, 1H), 7.60 (ABq, 4H), 7.75 (d, 1H), 8.11 (s, 1H).

IR (mineral oil): 3390, 1685 cm$^{-1}$.

Step D: 7-Chloro-2,3,3a,4-tetrahydro-3a-(1-methylethyl)-N-[4-(trifluoromethyl)phenyl][1]-benzopyrano[4,3-c]pyrazole-2-carboximidoyl chloride To 0.50 g (0.0012 mol) of the product obtained in Step C in 20 mL of benzene was added 0.25 g (0.0012 mol) of phosphorous pentachloride. The reaction mixture was refluxed for 42 hours, cooled to room temperature, poured into a saturated solution of sodium bicarbonate (100 mL) and extracted with ethyl acetate (3×50 mL). The ethyl acetate was washed with brine (100 mL), dried over anhydrous magnesium sulfate, filtered and concentrated under reduced pressure to afford an off-white solid. The solid was chromatographed on silica gel using ethyl acetate (15%) and hexanes (85%) as eluents which yielded 0.04 g of a white solid, mp 148° C. to 149° C.

200 MHz $^1$H NMR (CDCl$_3$) $\delta$ 0.88 (d, 3H), 1.1 (d, 3H), 2.15 (m, 1H), 3.6 (d, 1H), 4.16 (t, 2H), 4.60 (d, 1H), 7.0 (m, 4H), 7.60 (d, 2H), 7.78 (d, 1H)

EXAMPLE 2

Step A: 2-Phenyl-1-[4-(trifluoromethyl)phenyl]ethanone

To a solution of 45.0 g of 1-bromo-4-(trifluoromethyl)benzene in 300 mL of THF cooled to −78° C. was added 77.0 mL of 2.5M n-butyl lithium in hexane dropwise. An exothermic reaction to −55° C. was observed. The reaction was then stirred for 20 minutes after which time phenyl acetaldehyde (23.5 mL, 0.2 mol) was added dropwise. The reaction was then stirred for an additional hour with gradual warming to room temperature. The mixture was then partitioned between ether and water, dried over anhydrous magnesium sulfate and concentrated to 52.6 g of a yellow oil. The crude oil was dissolved in 600 mL of methylene chloride and 100 g of pyridinium dichromate was added in several portions over 20 minutes and the mixture was then stirred at room temperature overnight. The reaction was then diluted with ether and filtered through magnesium sulfate and concentrated. The crude product was dissolved in hot n-butyl chloride, insoluble material was filtered off and the mixture was cooled to 0° C. Filtration and drying of the precipitate afforded 12.7 g of the title compound as a white solid, mp 127°–128° C.

$^1$H NMR (CDCl$_3$) $\delta$ 4.30 (s, 2H), 7.3 (m), 7.75 (d, 2H), 8.16 (d, 2H).

Step B: 4,5-Dihydro-4-phenyl-3-[4-(trifluoromethyl)phenyl]-1H-pyrazole

A mixture of 12.0 g of the compound from Step A, 13.0 mL of 37% formaldehyde, 0.5 mL of piperidine and 0.5 mL of glaciel acetic acid in 100 mL of methanol were combined and heated at reflux for 3 hours. The reaction was then concentrated and the crude product partitioned between chloroform and water. The chloroform extracts were dried over anhydrous sodium sulfate, filtered and concentrated. The residue was taken up in about 35 mL of ethanol, 4.0 mL of hydrazine hydrate was added and the mixture was heated at reflux for 4 hours. The reaction was then cooled to 0° C. and the precipitated product was filtered and dried to afford 6.65 g of the title compound as a white solid, mp 98°–112° C.

$^1$H NMR (CDCl$_3$) $\delta$ 3.60 (dd, 1H), 4.04 (t, 1H), 4.56 (dd, 1H), 7.1–7.8 (m).

Step C: N-(4-Chlorophenyl)-4,5-dihydro-4-phenyl-3-[4-(trifluoromethyl)phenyl]-1H-pyrazole-1-carbothioamide A mixture of 0.7 g of the compound from Step B and 0.41 g of 4-chlorophenyl isothiocyanate were combined in a solvent mixture of 2 mL methylene chloride and 5 mL ether. After stirring overnight the precipitated solids were filtered and dried to afford 0.69 g of the title compound as a white solid, mp 208°–210° C.

$^1$H NMR (CDCl$_3$) $\delta$ 4.46 (m, 1H), 4.80 (m, 2H), 7.2–7.4 (m), 7.6 (m, 1H), 7.78 (d, 2H), 8.60 (s, 1H).

Step D: N-(4-Chlorophenyl)-4,5-dihydro-$\alpha$-(methylthio)-4-phenyl-3-[4-(trifluoromethyl)phenyl]-1H-pyrazole-1-methanimine A mixture of 0.54 g of the compound from Step C and 0.1 mL of iodomethane were stirred overnight after which time the precipitated solids were filtered and dried. This product was suspended in 2 mL of chloroform and 2 mL of 5% aqueous sodium bicarbonate was added. After stirring overnight the layers were separated and the chloroform extracts dried over magnesium sulfate and concentrated to afford 0.12 g of the title compound as a yellow oil.

$^1$H NMR (CDCl$_3$) δ 2.39 (s, 3H), 3.95 (dd, 1H), 4.40 (t, 1H), 4.70 (dd, 1H), 6.84 (d, 1H), 7.2–7.4 (m), 7.54 (d, 2H), 7.78 (d, 2H).

EXAMPLE 3

1-(4-Chlorophenyl)-5-(4-fluorophenyl)-4,5-dihydro-N-[4-(trifluoromethyl)phenyl]-1H-pyrazole-3-carboximidoyl chloride To a solution of 2.50 g (0.0054 mol) of 1-(4-chlorophenyl)-5-(4-fluorophenyl)-N-[4-(trifluoromethyl)phenyl]-1H-pyrazole-3-carboxamide dissolved in 15 mL of acetonitrile was added 1.80 g (0.0067 mol) of triphenylphosphine and 0.83 g (0.0054 mol) of carbon tetrachloride. The yellow solution was stirred at room temperature overnight and concentrated to afford 4.0 g of a yellow solid. The crude product was chromatographed on silica gel using ethyl acetate (10%) and hexanes (90%) as eluents which afforded 0.64 g of a yellow solid, mp 154° C. to 156° C.

200 MHz $^1$H NMR (CDCl$_3$) δ 3.2 (m, 1H), 3.85 (m, 1H), 5.50 (m, 1H), 7.0–7.4 (m, 10H), 7.65 (m, 2H).

IR (mineral oil): 1640, 1610 cm$^{-1}$.

EXAMPLE 4

1-(4-Chlorophenyl)-5-(4-fluorophenyl)-4,5-dihydro-N'-hydroxy-N-[4-(trifluoromethyl)phenyl]-1H-pyrazole-3-carboximidamide To a solution of 1.0 g (0.002 mol) of the product from Example 3 dissolved in 25 mL chloroform was added 0.217 g (0.0031 mol) of hydroxylamine hydrochloride and 0.525 g (0.0052 mol) of triethylamine. The reaction mixture was refluxed for 18 hours, cooled and ethyl acetate (150 mL) was added and water (100 mL). The organic phase was washed with water (100 mL) and brine (100 mL), dried over anhydrous magnesium sulfate, filtered and concentrated under reduced pressure to afford a yellow solid. The crude solid was chromatographed on silica gel using ethyl acetate (20%) and hexanes (80%) as eluent to afford 0.50 g of a white solid, mp 188° C. to 191° C.

200 MHz $^1$H NMR (CDCl$_3$) δ 2.89 (m, 1H), 3.78 (m, 1H), 5.50 (m, 1H), 6.75–7.5 (m, 12H), 8.6 (bs, 1H), 11.3 (bs, 1H).

IR (mineral oil): 3360, 3300 cm$^{-1}$.

EXAMPLE 5

1-(4-Chlorophenyl)-5-(4-fluorophenyl)-4,5-dihydro-N'-[[(methylamino)carbonyl]oxy]-N-[4-(trifluoromethyl)phenyl]-1H-pyrazole-3-carboximidamide To a solution of 0.75 g (0.0015 mol) of the product obtained from Example 4 dissolved in 15 mL tetrahydrofuran was added 0.097 g (0.0017 mol) of methyl isocyanate and 0.20 g (0.002 mol) of triethylamine. The reaction mixture was stirred at room temperature for 18 hours, poured into cold water (50 mL) and extracted with ethyl acetate (3×50 mL). The ethyl acetate layer was washed with brine (100 mL), dried over anhydrous magnesium sulfate, filtered and concentrated under reduced pressure to afford 0.44 g of a white solid, mp 75° C. to 77° C.

200 MHz $^1$H NMR (CDCl$_3$) δ 2.92 (d, 3H), 3.1 (s, 1H), 3.75 (m, 1H), 5.25 (m, 1H), 6.2 (bs, 1H), 6.5 (m, 2H), 7.0–7.6 (m, 11H).

IR (mineral oil): 3300, 1740 cm$^{-1}$.

EXAMPLE 6

Step A: Methyl 2-[(2-formylphenoxy)methyl]-2-propenoate

To a solution of 3.8 g (0.0279 mol) of potassium carbonate in 90 mL of dimethylformamide at room temperature was added 3.4 g (0.0279 mol) of salicylaldehyde and 5.0 g (0.0279 mol) of methyl (2-bromomethyl)acrylate. The reaction mixture was heated at 70° C. for 2 hours, cooled to room temperature and poured into 400 mL ice water. A white solid precipitated and was filtered, rinsed with water (100 mL), dried, rinsed with hexanes (100 mL) and dried to afford 3.85 g of a white powder; mp 50°–52° C.

200 MHz $^1$H NMR (CDCl$_3$): δ 3.83 (s, 3H), 4.88 (s, 2H), 6.05 (s, 1H), 6.45 (s, 1H), 7.1 (m, 2H), 7.55 (t, 1H), 7.85 (d, 1H), 10.52 (s, 1H).

IR (mineral oil): 1730, 1700 cm$^{-1}$.

Step B: Methyl 1,2,3,3a,4,9b-hexahydro-2[[[4-(trifluoromethyl)phenyl]amino]carbonyl][1]benzopyrano[4,3-c]pyrazole-3a-carboxylate A solution of 7.15 g (0.0681 mol) of hydrazine dihydrochloride in 95 mL of tert-butanol and 5 mL of water was heated at reflux for ½ hour at which time 1.50 g (0.0068 mol) of the product from Step A was added all at once. The reaction mixture was refluxed for 20 hours and the solvent was removed by evaporation under reduced pressure. 200 mL of 1N sodium hydroxide was added and the crude product was extracted with ethyl acetate (3×75 mL). The ethyl acetate was washed with water (100 mL), dried over anhydrous magnesium sulfate, filtered into a flask containing 1.27 g (0.0068 mol) of α,α,α-trifluoro-p-tolylisocyanate. The reaction mixture was stirred at room temperature for ½ hour, the solvent was removed under reduced pressure and the crude product was chromatographed using ether/hexanes (35%:65%) as eluent to afford 0.219 g of a white solid; mp 211°–212° C.

200 MHz $^1$H NMR(CDCl$_3$): δ3.64 (s, 3H), 3.8 (q, 2H), 4.11 (d, 1H), 4.32 (d, 1H), 5.04 (d, 1H), 5.50 (d, 1H), 6.9 (t, 1H), 6.95 (t, 1H), 7.2 (m, 2H), 7.6 (ABq, 4H), 8.57 (s, 1H).

IR (mineral oil): 3390, 3250, 1748, 1690 cm$^{-1}$.

EXAMPLE 7

Methyl 1,2,3,3a,4,9b-hexahydro-1-[(methylamino)carbonyl]-2-[[[4-(trifluoromethyl)phenyl]amino]carbonyl][1]benzopyrano[4,3-c]pyrazole-3a-carboxylate The product (0.125 g, 0.000296 mol) of Example 6, Step B was dissolved in 5 mL ether and 0.023 g of methyl isocyanate was added and stirred for 30 min. Three drops of triethylamine was added and the reaction was stirred for 18 hours at room temperature. A white precipitate had formed, was filtered, rinsed with ether and dried to afford 0.075 g of a white solid; mp 208°–209° C.

200 MHz $^1$H NMR(CDCl$_3$): δ 2.93 (s, 3H), 3.30 (d, 1H), 3.34 (s, 3H), 4.41 (d, 1H), 4.83 (d, 1H), 4.99 (d, 1H), 5.07 (s, 1H), 6.1 (q, 1H), 6.78 (d, 1H), 6.98 (t, 1H), 7.15 (t, 1H), 7.50 (m, 1H), 7.55 (ABq, 4H), 8.15 (s, 1H).

IR (mineral oil): 3360–3260, 1740, 1650 cm$^{-1}$.

EXAMPLE 8

3,4-Bis(4-chlorophenyl)-N-[4-(trifluoromethyl)phenyl]-1-pyrazolidinecarboxamide To a solution of 0.473 g (0.0025 mol) of titanium tetrachloride in 10 mL of 1,2-dimethoxyethane was added 0.189 g (0.0048 mol) of sodium borohydride all at once at 0° C. The green solution was stirred at 0° C. for 5 minutes and 0.500 g (0.0012 mol) of 3,4-bis(4-chlorophenyl)-4,5-dihydro-N-[4-(trifluoromethyl)phenyl]-1H-pyrazole-1-carboxamide dissolved in 5 mL of 1,2-dimethoxyethane was added dropwise over 5 minutes. The cooling bath was removed and the dark brown solution was stirred at room temperature for 3 hours. The crude reaction mixture was poured into 100 mL of saturated sodium bicarbonate solution and extracted with ethyl acetate (3×50 mL). The ethyl acetate was washed with brine (100 mL), dried over anhydrous magnesium sulfate, filtered and the solvent was removed under reduced pressure to afford a yellow solid. The crude reaction product was chromatographed on silica gel with ethyl acetate/hexanes (40%:60%) as eluent and afforded 0.140 g of the title compound as a white solid; mp 242°–243° C.

200 MHz $^1$H NMR(CDCl$_3$): δ 3.90 (m, 2H), 4.22 (dd, 1H), 4.48 (dd, 1H), 4.70 (d, 1H), 6.68 (d, 2H), 6.81 (d, 2H), 7.18 (m, 4H), 7.6 (ABq, 4H), 8.58 (s, 1H).

IR (mineral oil): 3330, 3220, 1650 cm$^{-1}$.

EXAMPLE 9

1-(4-Chlorophenyl)-5-(4-fluorophenyl)-N-[4-(trifluoromethyl)phenyl]-3-pyrazolidinecarboxamide The title compound (0.040 g) was obtained by reduction of 1-(4-chlorophenyl)-5-(4-fluorophenyl)-N-[4-(trifluoromethyl)phenyl]-1H-pyrazole-3-carboxamide via the procedure described in Example 8, (mp 50°–55° C.).

200 MHz $^1$H NMR (CDCl$_3$) δ 2.7 (m, 1H), 2.9–3.2 (m, 1H), 3.8 (dd, 1H), 4.4 (m, 2H), 5.4 (dd, 1H), 6.7–7.8 (m, 12H), 8.6 s, ⅓H), 9.2 (s, ⅔H).

IR (mineral oil) 3350, 1660 cm$^{-1}$.

By the general procedures described herein, or obvious modifications thereof, the compounds of Tables 1 through 36 can be prepared.

GENERAL STRUCTURES FOR TABLES 1-36

| Table | Q |
|---|---|

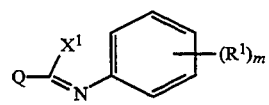

| | |
|---|---|
| 1 | Q-1 (R$^3$ = Me) |
| 2 | Q-1 (R$^3$ = iPr) |
| 3 | Q-1 (R$^3$ = CO$_2$Me) |
| 4 | Q-1 (R$^3$ = 4-F—Ph) |
| 5 | Q-1 (R$^3$ = 4-Cl—Ph) |
| 6 | Q-2 (V = O) |
| 7 | Q-3 (A = CH$_2$, Y$^1$ = H) |
| 8 | Q-3 (A = O, Y$^1$ = H) |
| 9 | Q-4 |
| 10 | Q-5 |

-continued
GENERAL STRUCTURES FOR TABLES 1-36

| Table | Q |
|---|---|

Q is 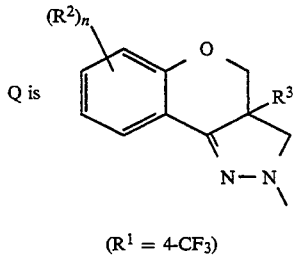

(R$^1$ = 4-CF$_3$)

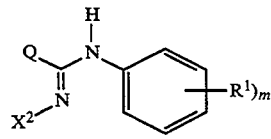

| | |
|---|---|
| 12 | Q-1 (R$^3$ = Me) |
| 13 | Q-1 (R$^3$ = iPr) |
| 14 | Q-1 (R$^3$ = CO$_2$Me) |
| 15 | Q-1 (R$^3$ = 4-F—Ph) |
| 16 | Q-1 (R$^3$ = 4-Cl—Ph) |
| 17 | Q-1 (V = O) |
| 18 | Q-2 (V = O) |
| 19 | Q-3 (A = CH$_2$, R$^5$ = H, Y$^1$ = H) |
| 20 | Q-3 (A = O, R$^5$ = H, Y$^1$ = H) |
| 21 | Q-5 |

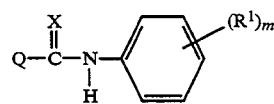

| | |
|---|---|
| 22 | Q-6 (R$^3$ = Me, R = H, X = O) |
| 23 | Q-6 (R$^3$ = iPr, R = H, X = O) |
| 24 | Q-6 (R$^3$ = CO$_2$Me, R = H, X = O) |
| 25 | Q-6 (R$^3$ = 4-F—Ph, R = H, X = O) |
| 26 | Q-6 (R$^3$ = 4-Cl—Ph, R = H, X = O) |
| 27 | Q-6 (R$^3$ = Me, R = Me, X = O) |
| 28 | Q-6 (R$^3$ = iPr, R = Me, X = O) |
| 29 | Q-6 (R$^3$ = CO$_2$Me, R = Me, X = O) |
| 30 | Q-6 (R$^3$ = 4-F—Ph, R = Me, X = O) |
| 31 | Q-6 (R$^3$ = 4-Cl—Ph, R = Me, X = O) |
| 32 | Q-7 (R = H, X = O) |
| 33 | Q-8 (A = CH$_2$, Y$^1$ = H, R = H, X = O) |
| 34 | Q-8 (A = O, Y$^1$ = H, R = H, X = O) |
| 35 | Q-9 (R = H, X = O) |
| 36 | Q-10 (R = H, X = O) |

For the Tables that follow, the values of Q-1 through Q-10 will be numbered as shown.

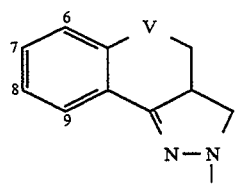

Q-1

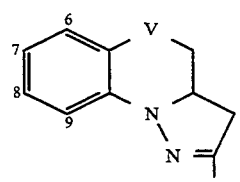

Q-2

-continued

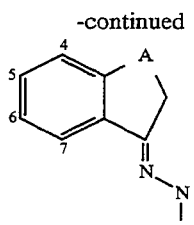
23

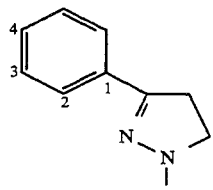
Q-4

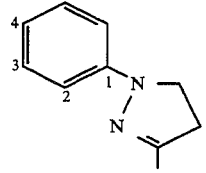
Q-5

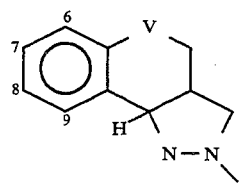
Q-6

-continued

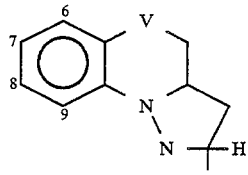
Q-7

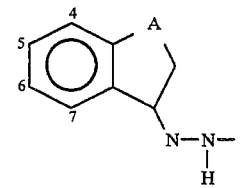
Q-8

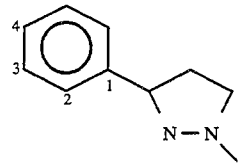
Q-9 and

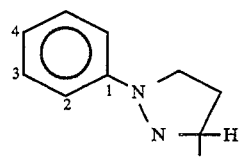
Q-10

TABLE 1

| R¹ | R² | V | X¹ | R¹ | R² | V | X¹ |
|---|---|---|---|---|---|---|---|
| 4-CF₃ | 7-F | CH₂ | Cl | 4-OCF₃ | 7-F | CH₂ | Cl |
| 4-CF₃ | 7-F | CH₂ | OMe | 4-OCF₃ | 7-F | CH₂ | OMe |
| 4-CF₃ | 7-F | CH₂ | SMe | 4-OCF₃ | 7-F | CH₂ | SMe |
| 4-CF₃ | 7-F | CH₂ | NMe₂ | 4-OCF₃ | 7-F | CH₂ | NMe₂ |
| 4-CF₃ | 7-Cl | CH₂ | Cl | 4-OCF₃ | 7-Cl | CH₂ | Cl |
| 4-CF₃ | 7-Cl | CH₂ | OMe | 4-OCF₃ | 7-Cl | CH₂ | OMe |
| 4-CF₃ | 7-Cl | CH₂ | SMe | 4-OCF₃ | 7-Cl | CH₂ | SMe |
| 4-CF₃ | 7-Cl | CH₂ | NMe₂ | 4-OCF₃ | 7-Cl | CH₂ | NMe₂ |
| 4-CF₃ | 7-CF₃ | CH₂ | Cl | 4-OCF₃ | 7-CF₃ | CH₂ | Cl |
| 4-CF₃ | 7-CF₃ | CH₂ | OMe | 4-OCF₃ | 7-CF₃ | CH₂ | OMe |
| 4-CF₃ | 7-CF₃ | CH₂ | SMe | 4-OCF₃ | 7-CF₃ | CH₂ | SMe |
| 4-CF₃ | 7-CF₃ | CH₂ | NMe₂ | 4-OCF₃ | 7-CF₃ | CH₂ | NMe₂ |
| 4-CF₃ | 6-F | CH₂ | Cl | 4-OCF₃ | 6-F | CH₂ | Cl |
| 4-CF₃ | 6-F | CH₂ | OMe | 4-OCF₃ | 6-F | CH₂ | OMe |
| 4-CF₃ | 6-F | CH₂ | SMe | 4-OCF₃ | 6-F | CH₂ | SMe |
| 4-CF₃ | 6-F | CH₂ | NMe₂ | 4-OCF₃ | 6-F | CH₂ | NMe₂ |
| 4-CF₃ | 7-F | O | Cl | 4-OCF₃ | 7-F | O | Cl |
| 4-CF₃ | 7-F | O | OMe | 4-OCF₃ | 7-F | O | OMe |
| 4-CF₃ | 7-F | O | SMe | 4-OCF₃ | 7-F | O | SMe |
| 4-CF₃ | 7-F | O | NMe₂ | 4-OCF₃ | 7-F | O | NMe₂ |
| 4-CF₃ | 7-Cl | O | Cl | 4-OCF₃ | 7-Cl | O | Cl |
| 4-CF₃ | 7-Cl | O | OMe | 4-OCF₃ | 7-Cl | O | OMe |
| 4-CF₃ | 7-Cl | O | SMe | 4-OCF₃ | 7-Cl | O | SMe |
| 4-CF₃ | 7-Cl | O | NMe₂ | 4-OCF₃ | 7-Cl | O | NMe₂ |
| 4-CF₃ | 7-CF₃ | O | Cl | 4-OCF₃ | 7-CF₃ | O | Cl |
| 4-CF₃ | 7-CF₃ | O | OMe | 4-OCF₃ | 7-CF₃ | O | OMe |
| 4-CF₃ | 7-CF₃ | O | SMe | 4-OCF₃ | 7-CF₃ | O | SMe |
| 4-CF₃ | 7-CF₃ | O | NMe₂ | 4-OCF₃ | 7-CF₃ | O | NMe₂ |
| 4-CF₃ | 6-F | O | Cl | 4-OCF₃ | 6-F | O | Cl |
| 4-CF₃ | 6-F | O | OMe | 4-OCF₃ | 6-F | O | OMe |
| 4-CF₃ | 6-F | O | SMe | 4-OCF₃ | 6-F | O | SMe |
| 4-CF₃ | 6-F | O | NMe₂ | 4-OCF₃ | 6-F | O | NMe₂ |
| 4-CF₃ | 7-F | NMe | Cl | 4-OCF₃ | 7-F | NMe | Cl |
| 4-CF₃ | 7-F | NMe | OMe | 4-OCF₃ | 7-F | NMe | OMe |
| 4-CF₃ | 7-F | NMe | SMe | 4-OCF₃ | 7-F | NMe | SMe |
| 4-CF₃ | 7-F | NMe | NMe₂ | 4-OCF₃ | 7-F | NMe | NMe₂ |
| 4-CF₃ | 7-Cl | NMe | Cl | 4-OCF₃ | 7-Cl | NMe | Cl |
| 4-CF₃ | 7-Cl | NMe | OMe | 4-OCF₃ | 7-Cl | NMe | OMe |

TABLE 1-continued

| R¹ | R² | V | X¹ | R¹ | R² | V | X¹ |
|---|---|---|---|---|---|---|---|
| 4-CF₃ | 7-Cl | NMe | SMe | 4-OCF₃ | 7-Cl | NMe | SMe |
| 4-CF₃ | 7-Cl | NMe | NMe₂ | 4-OCF₃ | 7-Cl | NMe | NMe₂ |
| 4-CF₃ | 7-CF₃ | NMe | Cl | 4-OCF₃ | 7-CF₃ | NMe | Cl |
| 4-CF₃ | 7-CF₃ | NMe | OMe | 4-OCF₃ | 7-CF₃ | NMe | OMe |
| 4-CF₃ | 7-CF₃ | NMe | SMe | 4-OCF₃ | 7-CF₃ | NMe | SMe |
| 4-CF₃ | 7-CF₃ | NMe | NMe₂ | 4-OCF₃ | 7-CF₃ | NMe | NMe₂ |
| 4-CF₃ | 6-F | NMe | Cl | 4-OCF₃ | 6-F | NMe | Cl |
| 4-CF₃ | 6-F | NMe | OMe | 4-OCF₃ | 6-F | NMe | OMe |
| 4-CF₃ | 6-F | NMe | SMe | 4-OCF₃ | 6-F | NMe | SMe |
| 4-CF₃ | 6-F | NMe | NMe₂ | 4-OCF₃ | 6-F | NMe | NMe₂ |
| 4-CF₃ | 7-F | NSO₂Me | Cl | 4-OCF₃ | 7-F | NSO₂Me | Cl |
| 4-CF₃ | 7-F | NSO₂Me | OMe | 4-OCF₃ | 7-F | NSO₂Me | OMe |
| 4-CF₃ | 7-F | NSO₂Me | SMe | 4-OCF₃ | 7-F | NSO₂Me | SMe |
| 4-CF₃ | 7-F | NSO₂Me | NMe₂ | 4-OCF₃ | 7-F | NSO₂Me | NMe₂ |
| 4-CF₃ | 7-Cl | NSO₂Me | Cl | 4-OCF₃ | 7-Cl | NSO₂Me | Cl |
| 4-CF₃ | 7-Cl | NSO₂Me | OMe | 4-OCF₃ | 7-Cl | NSO₂Me | OMe |
| 4-CF₃ | 7-Cl | NSO₂Me | SMe | 4-OCF₃ | 7-Cl | NSO₂Me | SMe |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | Cl | 4-OCF₃ | 7-CF₃ | NSO₂Me | Cl |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | SMe | 4-OCF₃ | 7-CF₃ | NSO₂Me | SMe |
| 4-CF₃ | 7-CF₃ | NSO₂Me | NMe₂ | 4-OCF₃ | 7-CF₃ | NSO₂Me | NMe₂ |
| 4-CF₃ | 6-F | NSO₂Me | Cl | 4-OCF₃ | 6-F | NSO₂Me | Cl |
| 4-CF₃ | 6-F | NSO₂Me | OMe | 4-OCF₃ | 6-F | NSO₂Me | OMe |
| 4-CF₃ | 6-F | NSO₂Me | SMe | 4-OCF₃ | 6-F | NSO₂Me | SMe |
| 4-CF₃ | 6-F | NSO₂Me | NMe₂ | 4-OCF₃ | 6-F | NSO₂Me | NMe₂ |

TABLE 2

| R¹ | R² | V | X¹ | R¹ | R² | V | X¹ |
|---|---|---|---|---|---|---|---|
| 4-CF₃ | 7-F | CH₂ | Cl | 4-OCF₃ | 7-F | CH₂ | Cl |
| 4-CF₃ | 7-F | CH₂ | OMe | 4-OCF₃ | 7-F | CH₂ | OMe |
| 4-CF₃ | 7-F | CH₂ | SMe | 4-OCF₃ | 7-F | CH₂ | SMe |
| 4-CF₃ | 7-F | CH₂ | NMe₂ | 4-OCF₃ | 7-F | CH₂ | NMe₂ |
| 4-CF₃ | 7-Cl | CH₂ | Cl | 4-OCF₃ | 7-Cl | CH₂ | Cl |
| 4-CF₃ | 7-Cl | CH₂ | OMe | 4-OCF₃ | 7-Cl | CH₂ | OMe |
| 4-CF₃ | 7-Cl | CH₂ | SMe | 4-OCF₃ | 7-Cl | CH₂ | SMe |
| 4-CF₃ | 7-Cl | CH₂ | NMe₂ | 4-OCF₃ | 7-Cl | CH₂ | NMe₂ |
| 4-CF₃ | 7-CF₃ | CH₂ | Cl | 4-OCF₃ | 7-CF₃ | CH₂ | Cl |
| 4-CF₃ | 7-CF₃ | CH₂ | OMe | 4-OCF₃ | 7-CF₃ | CH₂ | OMe |
| 4-CF₃ | 7-CF₃ | CH₂ | SMe | 4-OCF₃ | 7-CF₃ | CH₂ | SMe |
| 4-CF₃ | 7-CF₃ | CH₂ | NMe₂ | 4-OCF₃ | 7-CF₃ | CH₂ | NMe₂ |
| 4-CF₃ | 6-F | CH₂ | Cl | 4-OCF₃ | 6-F | CH₂ | Cl |
| 4-CF₃ | 6-F | CH₂ | OMe | 4-OCF₃ | 6-F | CH₂ | OMe |
| 4-CF₃ | 6-F | CH₂ | SMe | 4-OCF₃ | 6-F | CH₂ | SMe |
| 4-CF₃ | 6-F | CH₂ | NMe₂ | 4-OCF₃ | 6-F | CH₂ | NMe₂ |
| 4-CF₃ | 7-F | O | Cl | 4-OCF₃ | 7-F | O | Cl |
| 4-CF₃ | 7-F | O | OMe | 4-OCF₃ | 7-F | O | OMe |
| 4-CF₃ | 7-F | O | SMe | 4-OCF₃ | 7-F | O | SMe |
| 4-CF₃ | 7-F | O | NMe₂ | 4-OCF₃ | 7-F | O | NMe₂ |
| 4-CF₃ | 7-Cl | O | Cl | 4-OCF₃ | 7-Cl | O | Cl |
| 4-CF₃ | 7-Cl | O | OMe | 4-OCF₃ | 7-Cl | O | OMe |
| 4-CF₃ | 7-Cl | O | SMe | 4-OCF₃ | 7-Cl | O | SMe |
| 4-CF₃ | 7-Cl | O | NMe₂ | 4-OCF₃ | 7-Cl | O | NMe₂ |
| 4-CF₃ | 7-CF₃ | O | Cl | 4-OCF₃ | 7-CF₃ | O | Cl |
| 4-CF₃ | 7-CF₃ | O | OMe | 4-OCF₃ | 7-CF₃ | O | OMe |
| 4-CF₃ | 7-CF₃ | O | SMe | 4-OCF₃ | 7-CF₃ | O | SMe |
| 4-CF₃ | 7-CF₃ | O | NMe₂ | 4-OCF₃ | 7-CF₃ | O | NMe₂ |
| 4-CF₃ | 6-F | O | Cl | 4-OCF₃ | 6-F | O | Cl |
| 4-CF₃ | 6-F | O | OMe | 4-OCF₃ | 6-F | O | OMe |
| 4-CF₃ | 6-F | O | SMe | 4-OCF₃ | 6-F | O | SMe |
| 4-CF₃ | 6-F | O | NMe₂ | 4-OCF₃ | 6-F | O | NMe₂ |
| 4-CF₃ | 7-F | NMe | Cl | 4-OCF₃ | 7-F | NMe | Cl |
| 4-CF₃ | 7-F | NMe | OMe | 4-OCF₃ | 7-F | NMe | OMe |
| 4-CF₃ | 7-F | NMe | SMe | 4-OCF₃ | 7-F | NMe | SMe |
| 4-CF₃ | 7-F | NMe | NMe₂ | 4-OCF₃ | 7-F | NMe | NMe₂ |
| 4-CF₃ | 7-Cl | NMe | Cl | 4-OCF₃ | 7-Cl | NMe | Cl |
| 4-CF₃ | 7-Cl | NMe | OMe | 4-OCF₃ | 7-Cl | NMe | OMe |
| 4-CF₃ | 7-Cl | NMe | SMe | 4-OCF₃ | 7-Cl | NMe | SMe |
| 4-CF₃ | 7-Cl | NMe | NMe₂ | 4-OCF₃ | 7-Cl | NMe | NMe₂ |
| 4-CF₃ | 7-CF₃ | NMe | Cl | 4-OCF₃ | 7-CF₃ | NMe | Cl |
| 4-CF₃ | 7-CF₃ | NMe | OMe | 4-OCF₃ | 7-CF₃ | NMe | OMe |
| 4-CF₃ | 7-CF₃ | NMe | SMe | 4-OCF₃ | 7-CF₃ | NMe | SMe |
| 4-CF₃ | 7-CF₃ | NMe | NMe₂ | 4-OCF₃ | 7-CF₃ | NMe | NMe₂ |
| 4-CF₃ | 6-F | NMe | Cl | 4-OCF₃ | 6-F | NMe | Cl |
| 4-CF₃ | 6-F | NMe | OMe | 4-OCF₃ | 6-F | NMe | OMe |
| 4-CF₃ | 6-F | NMe | SMe | 4-OCF₃ | 6-F | NMe | SMe |
| 4-CF₃ | 6-F | NMe | NMe₂ | 4-OCF₃ | 6-F | NMe | NMe₂ |
| 4-CF₃ | 7-F | NSO₂Me | Cl | 4-OCF₃ | 7-F | NSO₂Me | Cl |

TABLE 2-continued

| R¹ | R² | V | X¹ | R¹ | R² | V | X¹ |
|---|---|---|---|---|---|---|---|
| 4-CF₃ | 7-F | NSO₂Me | OMe | 4-OCF₃ | 7-F | NSO₂Me | OMe |
| 4-CF₃ | 7-F | NSO₂Me | SMe | 4-OCF₃ | 7-F | NSO₂Me | SMe |
| 4-CF₃ | 7-F | NSO₂Me | NMe₂ | 4-OCF₃ | 7-F | NSO₂Me | NMe₂ |
| 4-CF₃ | 7-Cl | NSO₂Me | Cl | 4-OCF₃ | 7-Cl | NSO₂Me | Cl |
| 4-CF₃ | 7-Cl | NSO₂Me | OMe | 4-OCF₃ | 7-Cl | NSO₂Me | OMe |
| 4-CF₃ | 7-Cl | NSO₂Me | SMe | 4-OCF₃ | 7-Cl | NSO₂Me | SMe |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | Cl | 4-OCF₃ | 7-CF₃ | NSO₂Me | Cl |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | SMe | 4-OCF₃ | 7-CF₃ | NSO₂Me | SMe |
| 4-CF₃ | 7-CF₃ | NSO₂Me | NMe₂ | 4-OCF₃ | 7-CF₃ | NSO₂Me | NMe₂ |
| 4-CF₃ | 6-F | NSO₂Me | Cl | 4-OCF₃ | 6-F | NSO₂Me | Cl |
| 4-CF₃ | 6-F | NSO₂Me | OMe | 4-OCF₃ | 6-F | NSO₂Me | OMe |
| 4-CF₃ | 6-F | NSO₂Me | SMe | 4-OCF₃ | 6-F | NSO₂Me | SMe |
| 4-CF₃ | 6-F | NSO₂Me | NMe₂ | 4-OCF₃ | 6-F | NSO₂Me | NMe₂ |

TABLE 3

| R¹ | R² | V | X¹ | R¹ | R² | V | X¹ |
|---|---|---|---|---|---|---|---|
| 4-CF₃ | 7-F | CH₂ | Cl | 4-OCF₃ | 7-F | CH₂ | Cl |
| 4-CF₃ | 7-F | CH₂ | OMe | 4-OCF₃ | 7-F | CH₂ | OMe |
| 4-CF₃ | 7-F | CH₂ | SMe | 4-OCF₃ | 7-F | CH₂ | SMe |
| 4-CF₃ | 7-F | CH₂ | NMe₂ | 4-OCF₃ | 7-F | CH₂ | NMe₂ |
| 4-CF₃ | 7-Cl | CH₂ | Cl | 4-OCF₃ | 7-Cl | CH₂ | Cl |
| 4-CF₃ | 7-Cl | CH₂ | OMe | 4-OCF₃ | 7-Cl | CH₂ | OMe |
| 4-CF₃ | 7-Cl | CH₂ | SMe | 4-OCF₃ | 7-Cl | CH₂ | SMe |
| 4-CF₃ | 7-Cl | CH₂ | NMe₂ | 4-OCF₃ | 7-Cl | CH₂ | NMe₂ |
| 4-CF₃ | 7-CF₃ | CH₂ | Cl | 4-OCF₃ | 7-CF₃ | CH₂ | Cl |
| 4-CF₃ | 7-CF₃ | CH₂ | OMe | 4-OCF₃ | 7-CF₃ | CH₂ | OMe |
| 4-CF₃ | 7-CF₃ | CH₂ | SMe | 4-OCF₃ | 7-CF₃ | CH₂ | SMe |
| 4-CF₃ | 7-CF₃ | CH₂ | NMe₂ | 4-OCF₃ | 7-CF₃ | CH₂ | NMe₂ |
| 4-CF₃ | 6-F | CH₂ | Cl | 4-OCF₃ | 6-F | CH₂ | Cl |
| 4-CF₃ | 6-F | CH₂ | OMe | 4-OCF₃ | 6-F | CH₂ | OMe |
| 4-CF₃ | 6-F | CH₂ | SMe | 4-OCF₃ | 6-F | CH₂ | SMe |
| 4-CF₃ | 6-F | CH₂ | NMe₂ | 4-OCF₃ | 6-F | CH₂ | NMe₂ |
| 4-CF₃ | 7-F | O | Cl | 4-OCF₃ | 7-F | O | Cl |
| 4-CF₃ | 7-F | O | OMe | 4-OCF₃ | 7-F | O | OMe |
| 4-CF₃ | 7-F | O | SMe | 4-OCF₃ | 7-F | O | SMe |
| 4-CF₃ | 7-F | O | NMe₂ | 4-OCF₃ | 7-F | O | NMe₂ |
| 4-CF₃ | 7-Cl | O | Cl | 4-OCF₃ | 7-Cl | O | Cl |
| 4-CF₃ | 7-Cl | O | OMe | 4-OCF₃ | 7-Cl | O | OMe |
| 4-CF₃ | 7-Cl | O | SMe | 4-OCF₃ | 7-Cl | O | SMe |
| 4-CF₃ | 7-Cl | O | NMe₂ | 4-OCF₃ | 7-Cl | O | NMe₂ |
| 4-CF₃ | 7-CF₃ | O | Cl | 4-OCF₃ | 7-CF₃ | O | Cl |
| 4-CF₃ | 7-CF₃ | O | OMe | 4-OCF₃ | 7-CF₃ | O | OMe |
| 4-CF₃ | 7-CF₃ | O | SMe | 4-OCF₃ | 7-CF₃ | O | SMe |
| 4-CF₃ | 7-CF₃ | O | NMe₂ | 4-OCF₃ | 7-CF₃ | O | NMe₂ |
| 4-CF₃ | 7-CF₃ | O | OCO₂Me | 4-OCF₃ | 7-CF₃ | O | OCO₂Me |
| 4-CF₃ | 6-F | O | Cl | 4-OCF₃ | 6-F | O | Cl |
| 4-CF₃ | 6-F | O | OMe | 4-OCF₃ | 6-F | O | OMe |
| 4-CF₃ | 6-F | O | SMe | 4-OCF₃ | 6-F | O | SMe |
| 4-CF₃ | 6-F | O | NMe₂ | 4-OCF₃ | 6-F | O | NMe₂ |
| 4-CF₃ | 7-F | NMe | Cl | 4-OCF₃ | 7-F | NMe | Cl |
| 4-CF₃ | 7-F | NMe | OMe | 4-OCF₃ | 7-F | NMe | OMe |
| 4-CF₃ | 7-F | NMe | SMe | 4-OCF₃ | 7-F | NMe | SMe |
| 4-CF₃ | 7-F | NMe | NMe₂ | 4-OCF₃ | 7-F | NMe | NMe₂ |
| 4-CF₃ | 7-Cl | NMe | Cl | 4-OCF₃ | 7-Cl | NMe | Cl |
| 4-CF₃ | 7-Cl | NMe | OMe | 4-OCF₃ | 7-Cl | NMe | OMe |
| 4-CF₃ | 7-Cl | NMe | SMe | 4-OCF₃ | 7-Cl | NMe | SMe |
| 4-CF₃ | 7-Cl | NMe | NMe₂ | 4-OCF₃ | 7-Cl | NMe | NMe₂ |
| 4-CF₃ | 7-CF₃ | NMe | Cl | 4-OCF₃ | 7-CF₃ | NMe | Cl |
| 4-CF₃ | 7-CF₃ | NMe | OMe | 4-OCF₃ | 7-CF₃ | NMe | OMe |
| 4-CF₃ | 7-CF₃ | NMe | SMe | 4-OCF₃ | 7-CF₃ | NMe | SMe |
| 4-CF₃ | 7-CF₃ | NMe | NMe₂ | 4-OCF₃ | 7-CF₃ | NMe | NMe₂ |
| 4-CF₃ | 6-F | NMe | Cl | 4-OCF₃ | 6-F | NMe | Cl |
| 4-CF₃ | 6-F | NMe | OMe | 4-OCF₃ | 6-F | NMe | OMe |
| 4-CF₃ | 6-F | NMe | SMe | 4-OCF₃ | 6-F | NMe | SMe |
| 4-CF₃ | 6-F | NMe | NMe₂ | 4-OCF₃ | 6-F | NMe | NMe₂ |
| 4-CF₃ | 7-F | NSO₂Me | Cl | 4-OCF₃ | 7-F | NSO₂Me | Cl |
| 4-CF₃ | 7-F | NSO₂Me | OMe | 4-OCF₃ | 7-F | NSO₂Me | OMe |
| 4-CF₃ | 7-F | NSO₂Me | SMe | 4-OCF₃ | 7-F | NSO₂Me | SMe |
| 4-CF₃ | 7-F | NSO₂Me | NMe₂ | 4-OCF₃ | 7-F | NSO₂Me | NMe₂ |
| 4-CF₃ | 7-Cl | NSO₂Me | Cl | 4-OCF₃ | 7-Cl | NSO₂Me | Cl |
| 4-CF₃ | 7-Cl | NSO₂Me | OMe | 4-OCF₃ | 7-Cl | NSO₂Me | OMe |
| 4-CF₃ | 7-Cl | NSO₂Me | SMe | 4-OCF₃ | 7-Cl | NSO₂Me | SMe |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | Cl | 4-OCF₃ | 7-CF₃ | NSO₂Me | Cl |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | SMe | 4-OCF₃ | 7-CF₃ | NSO₂Me | SMe |

TABLE 3-continued

| R¹ | R² | V | X¹ | R¹ | R² | V | X¹ |
|---|---|---|---|---|---|---|---|
| 4-CF₃ | 7-CF₃ | NSO₂Me | NMe₂ | 4-OCF₃ | 7-CF₃ | NSO₂Me | NMe₂ |
| 4-CF₃ | 6-F | NSO₂Me | Cl | 4-OCF₃ | 6-F | NSO₂Me | Cl |
| 4-CF₃ | 6-F | NSO₂Me | OMe | 4-OCF₃ | 6-F | NSO₂Me | OMe |
| 4-CF₃ | 6-F | NSO₂Me | SMe | 4-OCF₃ | 6-F | NSO₂Me | SMe |
| 4-CF₃ | 6-F | NSO₂Me | NMe₂ | 4-OCF₃ | 6-F | NSO₂Me | NMe₂ |

TABLE 4

| R¹ | R² | V | X¹ | R¹ | R² | V | X¹ |
|---|---|---|---|---|---|---|---|
| 4-CF₃ | 7-F | CH₂ | Cl | 4-OCF₃ | 7-F | CH₂ | Cl |
| 4-CF₃ | 7-F | CH₂ | OMe | 4-OCF₃ | 7-F | CH₂ | OMe |
| 4-CF₃ | 7-F | CH₂ | SMe | 4-OCF₃ | 7-F | CH₂ | SMe |
| 4-CF₃ | 7-F | CH₂ | NMe₂ | 4-OCF₃ | 7-F | CH₂ | NMe₂ |
| 4-CF₃ | 7-Cl | CH₂ | Cl | 4-OCF₃ | 7-Cl | CH₂ | Cl |
| 4-CF₃ | 7-Cl | CH₂ | OMe | 4-OCF₃ | 7-Cl | CH₂ | OMe |
| 4-CF₃ | 7-Cl | CH₂ | SMe | 4-OCF₃ | 7-Cl | CH₂ | SMe |
| 4-CF₃ | 7-Cl | CH₂ | NMe₂ | 4-OCF₃ | 7-Cl | CH₂ | NMe₂ |
| 4-CF₃ | 7-CF₃ | CH₂ | Cl | 4-OCF₃ | 7-CF₃ | CH₂ | Cl |
| 4-CF₃ | 7-CF₃ | CH₂ | OMe | 4-OCF₃ | 7-CF₃ | CH₂ | OMe |
| 4-CF₃ | 7-CF₃ | CH₂ | SMe | 4-OCF₃ | 7-CF₃ | CH₂ | SMe |
| 4-CF₃ | 7-CF₃ | CH₂ | NMe₂ | 4-OCF₃ | 7-CF₃ | CH₂ | NMe₂ |
| 4-CF₃ | 6-F | CH₂ | Cl | 4-OCF₃ | 6-F | CH₂ | Cl |
| 4-CF₃ | 6-F | CH₂ | OMe | 4-OCF₃ | 6-F | CH₂ | OMe |
| 4-CF₃ | 6-F | CH₂ | SMe | 4-OCF₃ | 6-F | CH₂ | SMe |
| 4-CF₃ | 6-F | CH₂ | NMe₂ | 4-OCF₃ | 6-F | CH₂ | NMe₂ |
| 4-CF₃ | 7-F | O | Cl | 4-OCF₃ | 7-F | O | Cl |
| 4-CF₃ | 7-F | O | OMe | 4-OCF₃ | 7-F | O | OMe |
| 4-CF₃ | 7-F | O | SMe | 4-OCF₃ | 7-F | O | SMe |
| 4-CF₃ | 7-F | O | NMe₂ | 4-OCF₃ | 7-F | O | NMe₂ |
| 4-CF₃ | 7-Cl | O | Cl | 4-OCF₃ | 7-Cl | O | Cl |
| 4-CF₃ | 7-Cl | O | OMe | 4-OCF₃ | 7-Cl | O | OMe |
| 4-CF₃ | 7-Cl | O | SMe | 4-OCF₃ | 7-Cl | O | SMe |
| 4-CF₃ | 7-Cl | O | NMe₂ | 4-OCF₃ | 7-Cl | O | NMe₂ |
| 4-CF₃ | 7-CF₃ | O | Cl | 4-OCF₃ | 7-CF₃ | O | Cl |
| 4-CF₃ | 7-CF₃ | O | OMe | 4-OCF₃ | 7-CF₃ | O | OMe |
| 4-CF₃ | 7-CF₃ | O | SMe | 4-OCF₃ | 7-CF₃ | O | SMe |
| 4-CF₃ | 7-CF₃ | O | NMe₂ | 4-OCF₃ | 7-CF₃ | O | NMe₂ |
| 4-CF₃ | 6-F | O | Cl | 4-OCF₃ | 6-F | O | Cl |
| 4-CF₃ | 6-F | O | OMe | 4-OCF₃ | 6-F | O | OMe |
| 4-CF₃ | 6-F | O | SMe | 4-OCF₃ | 6-F | O | SMe |
| 4-CF₃ | 6-F | O | NMe₂ | 4-OCF₃ | 6-F | O | NMe₂ |
| 4-CF₃ | 7-F | NMe | Cl | 4-OCF₃ | 7-F | NMe | Cl |
| 4-CF₃ | 7-F | NMe | OMe | 4-OCF₃ | 7-F | NMe | OMe |
| 4-CF₃ | 7-F | NMe | SMe | 4-OCF₃ | 7-F | NMe | SMe |
| 4-CF₃ | 7-F | NMe | NMe₂ | 4-OCF₃ | 7-F | NMe | NMe₂ |
| 4-CF₃ | 7-Cl | NMe | Cl | 4-OCF₃ | 7-Cl | NMe | Cl |
| 4-CF₃ | 7-Cl | NMe | OMe | 4-OCF₃ | 7-Cl | NMe | OMe |
| 4-CF₃ | 7-Cl | NMe | SMe | 4-OCF₃ | 7-Cl | NMe | SMe |
| 4-CF₃ | 7-Cl | NMe | NMe₂ | 4-OCF₃ | 7-Cl | NMe | NMe₂ |
| 4-CF₃ | 7-CF₃ | NMe | Cl | 4-OCF₃ | 7-CF₃ | NMe | Cl |
| 4-CF₃ | 7-CF₃ | NMe | OMe | 4-OCF₃ | 7-CF₃ | NMe | OMe |
| 4-CF₃ | 7-CF₃ | NMe | SMe | 4-OCF₃ | 7-CF₃ | NMe | SMe |
| 4-CF₃ | 7-CF₃ | NMe | NMe₂ | 4-OCF₃ | 7-CF₃ | NMe | NMe₂ |
| 4-CF₃ | 6-F | NMe | Cl | 4-OCF₃ | 6-F | NMe | Cl |
| 4-CF₃ | 6-F | NMe | OMe | 4-OCF₃ | 6-F | NMe | OMe |
| 4-CF₃ | 6-F | NMe | SMe | 4-OCF₃ | 6-F | NMe | SMe |
| 4-CF₃ | 6-F | NMe | NMe₂ | 4-OCF₃ | 6-F | NMe | NMe₂ |
| 4-CF₃ | 7-F | NSO₂Me | Cl | 4-OCF₃ | 7-F | NSO₂Me | Cl |
| 4-CF₃ | 7-F | NSO₂Me | OMe | 4-OCF₃ | 7-F | NSO₂Me | OMe |
| 4-CF₃ | 7-F | NSO₂Me | SMe | 4-OCF₃ | 7-F | NSO₂Me | SMe |
| 4-CF₃ | 7-F | NSO₂Me | NMe₂ | 4-OCF₃ | 7-F | NSO₂Me | NMe₂ |
| 4-CF₃ | 7-Cl | NSO₂Me | Cl | 4-OCF₃ | 7-Cl | NSO₂Me | Cl |
| 4-CF₃ | 7-Cl | NSO₂Me | OMe | 4-OCF₃ | 7-Cl | NSO₂Me | OMe |
| 4-CF₃ | 7-Cl | NSO₂Me | SMe | 4-OCF₃ | 7-Cl | NSO₂Me | SMe |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | Cl | 4-OCF₃ | 7-CF₃ | NSO₂Me | Cl |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | SMe | 4-OCF₃ | 7-CF₃ | NSO₂Me | SMe |
| 4-CF₃ | 7-CF₃ | NSO₂Me | NMe₂ | 4-OCF₃ | 7-CF₃ | NSO₂Me | NMe₂ |
| 4-CF₃ | 6-F | NSO₂Me | Cl | 4-OCF₃ | 6-F | NSO₂Me | Cl |
| 4-CF₃ | 6-F | NSO₂Me | OMe | 4-OCF₃ | 6-F | NSO₂Me | OMe |
| 4-CF₃ | 6-F | NSO₂Me | SMe | 4-OCF₃ | 6-F | NSO₂Me | SMe |
| 4-CF₃ | 6-F | NSO₂Me | NMe₂ | 4-OCF₃ | 6-F | NSO₂Me | NMe₂ |

TABLE 5

| R¹ | R² | V | X¹ | R¹ | R² | V | X¹ |
|---|---|---|---|---|---|---|---|
| 4-CF₃ | 7-F | CH₂ | Cl | 4-OCF₃ | 7-F | CH₂ | Cl |

TABLE 5-continued

| R¹ | R² | V | X¹ | R¹ | R² | V | X¹ |
|---|---|---|---|---|---|---|---|
| 4-CF₃ | 7-F | CH₂ | OMe | 4-OCF₃ | 7-F | CH₂ | OMe |
| 4-CF₃ | 7-F | CH₂ | SMe | 4-OCF₃ | 7-F | CH₂ | SMe |
| 4-CF₃ | 7-F | CH₂ | NMe₂ | 4-OCF₃ | 7-F | CH₂ | NMe₂ |
| 4-CF₃ | 7-Cl | CH₂ | Cl | 4-OCF₃ | 7-Cl | CH₂ | Cl |
| 4-CF₃ | 7-Cl | CH₂ | OMe | 4-OCF₃ | 7-Cl | CH₂ | OMe |
| 4-CF₃ | 7-Cl | CH₂ | SMe | 4-OCF₃ | 7-Cl | CH₂ | SMe |
| 4-CF₃ | 7-Cl | CH₂ | NMe₂ | 4-OCF₃ | 7-Cl | CH₂ | NMe₂ |
| 4-CF₃ | 7-CF₃ | CH₂ | Cl | 4-OCF₃ | 7-CF₃ | CH₂ | Cl |
| 4-CF₃ | 7-CF₃ | CH₂ | OMe | 4-OCF₃ | 7-CF₃ | CH₂ | OMe |
| 4-CF₃ | 7-CF₃ | CH₂ | SMe | 4-OCF₃ | 7-CF₃ | CH₂ | SMe |
| 4-CF₃ | 7-CF₃ | CH₂ | NMe₂ | 4-OCF₃ | 7-CF₃ | CH₂ | NMe₂ |
| 4-CF₃ | 6-F | CH₂ | Cl | 4-OCF₃ | 6-F | CH₂ | Cl |
| 4-CF₃ | 6-F | CH₂ | OMe | 4-OCF₃ | 6-F | CH₂ | OMe |
| 4-CF₃ | 6-F | CH₂ | SMe | 4-OCF₃ | 6-F | CH₂ | SMe |
| 4-CF₃ | 6-F | CH₂ | NMe₂ | 4-OCF₃ | 6-F | CH₂ | NMe₂ |
| 4-CF₃ | 7-F | O | Cl | 4-OCF₃ | 7-F | O | Cl |
| 4-CF₃ | 7-F | O | OMe | 4-OCF₃ | 7-F | O | OMe |
| 4-CF₃ | 7-F | O | SMe | 4-OCF₃ | 7-F | O | SMe |
| 4-CF₃ | 7-F | O | NMe₂ | 4-OCF₃ | 7-F | O | NMe₂ |
| 4-CF₃ | 7-Cl | O | Cl | 4-OCF₃ | 7-Cl | O | Cl |
| 4-CF₃ | 7-Cl | O | OMe | 4-OCF₃ | 7-Cl | O | OMe |
| 4-CF₃ | 7-Cl | O | SMe | 4-OCF₃ | 7-Cl | O | SMe |
| 4-CF₃ | 7-Cl | O | NMe₂ | 4-OCF₃ | 7-Cl | O | NMe₂ |
| 4-CF₃ | 7-CF₃ | O | Cl | 4-OCF₃ | 7-CF₃ | O | Cl |
| 4-CF₃ | 7-CF₃ | O | OMe | 4-OCF₃ | 7-CF₃ | O | OMe |
| 4-CF₃ | 7-CF₃ | O | SMe | 4-OCF₃ | 7-CF₃ | O | SMe |
| 4-CF₃ | 7-CF₃ | O | NMe₂ | 4-OCF₃ | 7-CF₃ | O | NMe₂ |
| 4-CF₃ | 6-F | O | Cl | 4-OCF₃ | 6-F | O | Cl |
| 4-CF₃ | 6-F | O | OMe | 4-OCF₃ | 6-F | O | OMe |
| 4-CF₃ | 6-F | O | SMe | 4-OCF₃ | 6-F | O | SMe |
| 4-CF₃ | 6-F | O | NMe₂ | 4-OCF₃ | 6-F | O | NMe₂ |
| 4-CF₃ | 7-F | NMe | Cl | 4-OCF₃ | 7-F | NMe | Cl |
| 4-CF₃ | 7-F | NMe | OMe | 4-OCF₃ | 7-F | NMe | OMe |
| 4-CF₃ | 7-F | NMe | SMe | 4-OCF₃ | 7-F | NMe | SMe |
| 4-CF₃ | 7-F | NMe | NMe₂ | 4-OCF₃ | 7-F | NMe | NMe₂ |
| 4-CF₃ | 7-Cl | NMe | Cl | 4-OCF₃ | 7-Cl | NMe | Cl |
| 4-CF₃ | 7-Cl | NMe | OMe | 4-OCF₃ | 7-Cl | NMe | OMe |
| 4-CF₃ | 7-Cl | NMe | SMe | 4-OCF₃ | 7-Cl | NMe | SMe |
| 4-CF₃ | 7-Cl | NMe | NMe₂ | 4-OCF₃ | 7-Cl | NMe | NMe₂ |
| 4-CF₃ | 7-CF₃ | NMe | Cl | 4-OCF₃ | 7-CF₃ | NMe | Cl |
| 4-CF₃ | 7-CF₃ | NMe | OMe | 4-OCF₃ | 7-CF₃ | NMe | OMe |
| 4-CF₃ | 7-CF₃ | NMe | SMe | 4-OCF₃ | 7-CF₃ | NMe | SMe |
| 4-CF₃ | 7-CF₃ | NMe | NMe₂ | 4-OCF₃ | 7-CF₃ | NMe | NMe₂ |
| 4-CF₃ | 6-F | NMe | Cl | 4-OCF₃ | 6-F | NMe | Cl |
| 4-CF₃ | 6-F | NMe | OMe | 4-OCF₃ | 6-F | NMe | OMe |
| 4-CF₃ | 6-F | NMe | SMe | 4-OCF₃ | 6-F | NMe | SMe |
| 4-CF₃ | 6-F | NMe | NMe₂ | 4-OCF₃ | 6-F | NMe | NMe₂ |
| 4-CF₃ | 7-F | NSO₂Me | Cl | 4-OCF₃ | 7-F | NSO₂Me | Cl |
| 4-CF₃ | 7-F | NSO₂Me | OMe | 4-OCF₃ | 7-F | NSO₂Me | OMe |
| 4-CF₃ | 7-F | NSO₂Me | SMe | 4-OCF₃ | 7-F | NSO₂Me | SMe |
| 4-CF₃ | 7-F | NSO₂Me | NMe₂ | 4-OCF₃ | 7-F | NSO₂Me | NMe₂ |
| 4-CF₃ | 7-Cl | NSO₂Me | Cl | 4-OCF₃ | 7-Cl | NSO₂Me | Cl |
| 4-CF₃ | 7-Cl | NSO₂Me | OMe | 4-OCF₃ | 7-Cl | NSO₂Me | OMe |
| 4-CF₃ | 7-Cl | NSO₂Me | SMe | 4-OCF₃ | 7-Cl | NSO₂Me | SMe |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | Cl | 4-OCF₃ | 7-CF₃ | NSO₂Me | Cl |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | SMe | 4-OCF₃ | 7-CF₃ | NSO₂Me | SMe |
| 4-CF₃ | 7-CF₃ | NSO₂Me | NMe₂ | 4-OCF₃ | 7-CF₃ | NSO₂Me | NMe₂ |
| 4-CF₃ | 6-F | NSO₂Me | Cl | 4-OCF₃ | 6-F | NSO₂Me | Cl |
| 4-CF₃ | 6-F | NSO₂Me | OMe | 4-OCF₃ | 6-F | NSO₂Me | OMe |
| 4-CF₃ | 6-F | NSO₂Me | SMe | 4-OCF₃ | 6-F | NSO₂Me | SMe |
| 4-CF₃ | 6-F | NSO₂Me | NMe₂ | 4-OCF₃ | 6-F | NSO₂Me | NMe₂ |

TABLE 6

| R¹ | R² | R³ | X¹ | R¹ | R² | R³ | X¹ |
|---|---|---|---|---|---|---|---|
| 4-CF₃ | 7-F | CO₂Me | Cl | 4-OCF₃ | 7-F | CO₂Me | Cl |
| 4-CF₃ | 7-F | CO₂Me | OMe | 4-OCF₃ | 7-F | CO₂Me | OMe |
| 4-CF₃ | 7-F | CO₂Me | SMe | 4-OCF₃ | 7-F | CO₂Me | SMe |
| 4-CF₃ | 7-F | CO₂Me | NMe₂ | 4-OCF₃ | 7-F | CO₂Me | NMe₂ |
| 4-CF₃ | 7-Cl | CO₂Me | Cl | 4-OCF₃ | 7-Cl | CO₂Me | Cl |
| 4-CF₃ | 7-Cl | CO₂Me | OMe | 4-OCF₃ | 7-Cl | CO₂Me | OMe |
| 4-CF₃ | 7-Cl | CO₂Me | SMe | 4-OCF₃ | 7-Cl | CO₂Me | SMe |
| 4-CF₃ | 7-Cl | CO₂Me | NMe₂ | 4-OCF₃ | 7-Cl | CO₂Me | NMe₂ |
| 4-CF₃ | 7-F | 4-F-Ph | Cl | 4-OCF₃ | 7-F | 4-F-Ph | Cl |
| 4-CF₃ | 7-F | 4-F-Ph | OMe | 4-OCF₃ | 7-F | 4-F-Ph | OMe |
| 4-CF₃ | 7-F | 4-F-Ph | SMe | 4-OCF₃ | 7-F | 4-F-Ph | SMe |
| 4-CF₃ | 7-F | 4-F-Ph | NMe₂ | 4-OCF₃ | 7-F | 4-F-Ph | NMe₂ |
| 4-CF₃ | 7-Cl | 4-F-Ph | Cl | 4-OCF₃ | 7-Cl | 4-F-Ph | Cl |
| 4-CF₃ | 7-Cl | 4-F-Ph | OMe | 4-OCF₃ | 7-Cl | 4-F-Ph | OMe |
| 4-CF₃ | 7-Cl | 4-F-Ph | SMe | 4-OCF₃ | 7-Cl | 4-F-Ph | SMe |
| 4-CF₃ | 7-Cl | 4-F-Ph | NMe₂ | 4-OCF₃ | 7-Cl | 4-F-Ph | NMe₂ |

TABLE 7

| R¹ | R² | R⁴ | X¹ | R¹ | R² | R⁴ | X¹ |
|---|---|---|---|---|---|---|---|
| 4-CF₃ | 5-F | Me | Cl | 4-OCF₃ | 5-F | Me | Cl |
| 4-CF₃ | 5-F | iPr | Cl | 4-OCF₃ | 5-F | iPr | Cl |
| 4-CF₃ | 5-F | Ph | Cl | 4-OCF₃ | 5-F | Ph | Cl |
| 4-CF₃ | 5-F | 4-F-Ph | Cl | 4-OCF₃ | 5-F | 4-F-Ph | Cl |
| 4-CF₃ | 5-F | 4-Cl-Ph | Cl | 4-OCF₃ | 5-F | 4-Cl-Ph | Cl |
| 4-CF₃ | 5-Cl | Me | Cl | 4-OCF₃ | 5-Cl | Me | Cl |
| 4-CF₃ | 5-Cl | iPr | Cl | 4-OCF₃ | 5-Cl | iPr | Cl |
| 4-CF₃ | 5-Cl | Ph | Cl | 4-OCF₃ | 5-Cl | Ph | Cl |
| 4-CF₃ | 5-Cl | 4-F-Ph | Cl | 4-OCF₃ | 5-Cl | 4-F-Ph | Cl |
| 4-CF₃ | 5-Cl | 4-Cl-Ph | Cl | 4-OCF₃ | 5-Cl | 4-Cl-Ph | Cl |
| 4-CF₃ | 5-CF₃ | Me | Cl | 4-OCF₃ | 5-CF₃ | Me | Cl |
| 4-CF₃ | 5-CF₃ | iPr | Cl | 4-OCF₃ | 5-CF₃ | iPr | Cl |
| 4-CF₃ | 5-CF₃ | Ph | Cl | 4-OCF₃ | 5-CF₃ | Ph | Cl |
| 4-CF₃ | 5-CF₃ | 4-F-Ph | Cl | 4-OCF₃ | 5-CF₃ | 4-F-Ph | Cl |
| 4-CF₃ | 5-CF₃ | 4-Cl-Ph | Cl | 4-OCF₃ | 5-CF₃ | 4-Cl-Ph | Cl |
| 4-CF₃ | 5-OCF₃ | Me | Cl | 4-OCF₃ | 5-OCF₃ | Me | Cl |
| 4-CF₃ | 5-OCF₃ | iPr | Cl | 4-OCF₃ | 5-OCF₃ | iPr | Cl |
| 4-CF₃ | 5-OCF₃ | Ph | Cl | 4-OCF₃ | 5-OCF₃ | Ph | Cl |
| 4-CF₃ | 5-OCF₃ | 4-F-Ph | Cl | 4-OCF₃ | 5-OCF₃ | 4-F-Ph | Cl |
| 4-CF₃ | 5-OCF₃ | 4-Cl-Ph | Cl | 4-OCF₃ | 5-OCF₃ | 4-Cl-Ph | Cl |
| 4-CF₃ | 4-F | Me | Cl | 4-OCF₃ | 4-F | Me | Cl |
| 4-CF₃ | 4-F | iPr | Cl | 4-OCF₃ | 4-F | iPr | Cl |
| 4-CF₃ | 4-F | Ph | Cl | 4-OCF₃ | 4-F | Ph | Cl |
| 4-CF₃ | 4-F | 4-F-Ph | Cl | 4-OCF₃ | 4-F | 4-F-Ph | Cl |
| 4-CF₃ | 4-F | 4-Cl-Ph | Cl | 4-OCF₃ | 4-F | 4-Cl-Ph | Cl |
| 4-CF₃ | 5-F | Me | OMe | 4-OCF₃ | 5-F | Me | OMe |
| 4-CF₃ | 5-F | iPr | OMe | 4-OCF₃ | 5-F | iPr | OMe |
| 4-CF₃ | 5-F | Ph | OMe | 4-OCF₃ | 5-F | Ph | OMe |
| 4-CF₃ | 5-F | 4-F-Ph | OMe | 4-OCF₃ | 5-F | 4-F-Ph | OMe |
| 4-CF₃ | 5-F | 4-Cl-Ph | OMe | 4-OCF₃ | 5-F | 4-Cl-Ph | OMe |
| 4-CF₃ | 5-Cl | Me | OMe | 4-OCF₃ | 5-Cl | Me | OMe |
| 4-CF₃ | 5-Cl | iPr | OMe | 4-OCF₃ | 5-Cl | iPr | OMe |
| 4-CF₃ | 5-Cl | Ph | OMe | 4-OCF₃ | 5-Cl | Ph | OMe |
| 4-CF₃ | 5-Cl | 4-F-Ph | OMe | 4-OCF₃ | 5-Cl | 4-F-Ph | OMe |
| 4-CF₃ | 5-Cl | 4-Cl-Ph | OMe | 4-OCF₃ | 5-Cl | 4-Cl-Ph | OMe |
| 4-CF₃ | 5-CF₃ | Me | OMe | 4-OCF₃ | 5-CF₃ | Me | OMe |
| 4-CF₃ | 5-CF₃ | iPr | OMe | 4-OCF₃ | 5-CF₃ | iPr | OMe |
| 4-CF₃ | 5-CF₃ | Ph | OMe | 4-OCF₃ | 5-CF₃ | Ph | OMe |
| 4-CF₃ | 5-CF₃ | 4-F-Ph | OMe | 4-OCF₃ | 5-CF₃ | 4-F-Ph | OMe |
| 4-CF₃ | 5-CF₃ | 4-Cl-Ph | OMe | 4-OCF₃ | 5-CF₃ | 4-Cl-Ph | OMe |
| 4-CF₃ | 5-OCF₃ | Me | OMe | 4-OCF₃ | 5-OCF₃ | Me | OMe |
| 4-CF₃ | 5-OCF₃ | iPr | OMe | 4-OCF₃ | 5-OCF₃ | iPr | OMe |
| 4-CF₃ | 5-OCF₃ | Ph | OMe | 4-OCF₃ | 5-OCF₃ | Ph | OMe |
| 4-CF₃ | 5-OCF₃ | 4-F-Ph | OMe | 4-OCF₃ | 5-OCF₃ | 4-F-Ph | OMe |
| 4-CF₃ | 5-OCF₃ | 4-Cl-Ph | OMe | 4-OCF₃ | 5-OCF₃ | 4-Cl-Ph | OMe |
| 4-CF₃ | 4-F | Me | OMe | 4-OCF₃ | 4-F | Me | OMe |
| 4-CF₃ | 4-F | iPr | OMe | 4-OCF₃ | 4-F | iPr | OMe |
| 4-CF₃ | 4-F | Ph | OMe | 4-OCF₃ | 4-F | Ph | OMe |
| 4-CF₃ | 4-F | 4-F-Ph | OMe | 4-OCF₃ | 4-F | 4-F-Ph | OMe |
| 4-CF₃ | 4-F | 4-Cl-Ph | OMe | 4-OCF₃ | 4-F | 4-Cl-Ph | OMe |
| 4-CF₃ | 5-F | Me | SMe | 4-OCF₃ | 5-F | Me | SMe |
| 4-CF₃ | 5-F | iPr | SMe | 4-OCF₃ | 5-F | iPr | SMe |
| 4-CF₃ | 5-F | Ph | SMe | 4-OCF₃ | 5-F | Ph | SMe |
| 4-CF₃ | 5-F | 4-F-Ph | SMe | 4-OCF₃ | 5-F | 4-F-Ph | SMe |
| 4-CF₃ | 5-F | 4-Cl-Ph | SMe | 4-OCF₃ | 5-F | 4-Cl-Ph | SMe |
| 4-CF₃ | 5-Cl | Me | SMe | 4-OCF₃ | 5-Cl | Me | SMe |
| 4-CF₃ | 5-Cl | iPr | SMe | 4-OCF₃ | 5-Cl | iPr | SMe |
| 4-CF₃ | 5-Cl | Ph | SMe | 4-OCF₃ | 5-Cl | Ph | SMe |
| 4-CF₃ | 5-Cl | 4-F-Ph | SMe | 4-OCF₃ | 5-Cl | 4-F-Ph | SMe |
| 4-CF₃ | 5-Cl | 4-Cl-Ph | SMe | 4-OCF₃ | 5-Cl | 4-Cl-Ph | SMe |
| 4-CF₃ | 5-CF₃ | Me | SMe | 4-OCF₃ | 5-CF₃ | Me | SMe |
| 4-CF₃ | 5-CF₃ | iPr | SMe | 4-OCF₃ | 5-CF₃ | iPr | SMe |
| 4-CF₃ | 5-CF₃ | Ph | SMe | 4-OCF₃ | 5-CF₃ | Ph | SMe |
| 4-CF₃ | 5-CF₃ | 4-F-Ph | SMe | 4-OCF₃ | 5-CF₃ | 4-F-Ph | SMe |
| 4-CF₃ | 5-CF₃ | 4-Cl-Ph | SMe | 4-OCF₃ | 5-CF₃ | 4-Cl-Ph | SMe |
| 4-CF₃ | 5-OCF₃ | Me | SMe | 4-OCF₃ | 5-OCF₃ | Me | SMe |
| 4-CF₃ | 5-OCF₃ | iPr | SMe | 4-OCF₃ | 5-OCF₃ | iPr | SMe |
| 4-CF₃ | 5-OCF₃ | Ph | SMe | 4-OCF₃ | 5-OCF₃ | Ph | SMe |
| 4-CF₃ | 5-OCF₃ | 4-F-Ph | SMe | 4-OCF₃ | 5-OCF₃ | 4-F-Ph | SMe |
| 4-CF₃ | 5-OCF₃ | 4-Cl-Ph | SMe | 4-OCF₃ | 5-OCF₃ | 4-Cl-Ph | SMe |
| 4-CF₃ | 4-F | Me | SMe | 4-OCF₃ | 4-F | Me | SMe |
| 4-CF₃ | 4-F | iPr | SMe | 4-OCF₃ | 4-F | iPr | SMe |
| 4-CF₃ | 4-F | Ph | SMe | 4-OCF₃ | 4-F | Ph | SMe |
| 4-CF₃ | 4-F | 4-F-Ph | SMe | 4-OCF₃ | 4-F | 4-F-Ph | SMe |
| 4-CF₃ | 4-F | 4-Cl-Ph | SMe | 4-OCF₃ | 4-F | 4-Cl-Ph | SMe |
| 4-CF₃ | 5-F | Me | NMe₂ | 4-OCF₃ | 5-F | Me | NMe₂ |
| 4-CF₃ | 5-F | iPr | NMe₂ | 4-OCF₃ | 5-F | iPr | NMe₂ |
| 4-CF₃ | 5-F | Ph | NMe₂ | 4-OCF₃ | 5-F | Ph | NMe₂ |
| 4-CF₃ | 5-F | 4-F-Ph | NMe₂ | 4-OCF₃ | 5-F | 4-F-Ph | NMe₂ |
| 4-CF₃ | 5-F | 4-Cl-Ph | NMe₂ | 4-OCF₃ | 5-F | 4-Cl-Ph | NMe₂ |
| 4-CF₃ | 5-Cl | Me | NMe₂ | 4-OCF₃ | 5-Cl | Me | NMe₂ |

TABLE 7-continued

| R¹ | R² | R⁴ | X¹ | R¹ | R² | R⁴ | X¹ |
|---|---|---|---|---|---|---|---|
| 4-CF₃ | 5-Cl | iPr | NMe₂ | 4-OCF₃ | 5-Cl | iPr | NMe₂ |
| 4-CF₃ | 5-Cl | Ph | NMe₂ | 4-OCF₃ | 5-Cl | Ph | NMe₂ |
| 4-CF₃ | 5-Cl | 4-F-Ph | NMe₂ | 4-OCF₃ | 5-Cl | 4-F-Ph | NMe₂ |
| 4-CF₃ | 5-Cl | 4-Cl-Ph | NMe₂ | 4-OCF₃ | 5-Cl | 4-Cl-Ph | NMe₂ |
| 4-CF₃ | 5-CF₃ | Me | NMe₂ | 4-OCF₃ | 5-CF₃ | Me | NMe₂ |
| 4-CF₃ | 5-CF₃ | iPr | NMe₂ | 4-OCF₃ | 5-CF₃ | iPr | NMe₂ |
| 4-CF₃ | 5-CF₃ | Ph | NMe₂ | 4-OCF₃ | 5-CF₃ | Ph | NMe₂ |
| 4-CF₃ | 5-CF₃ | 4-F-Ph | NMe₂ | 4-OCF₃ | 5-CF₃ | 4-F-Ph | NMe₂ |
| 4-CF₃ | 5-CF₃ | 4-Cl-Ph | NMe₂ | 4-OCF₃ | 5-CF₃ | 4-Cl-Ph | NMe₂ |
| 4-CF₃ | 5-OCF₃ | Me | NMe₂ | 4-OCF₃ | 5-OCF₃ | Me | NMe₂ |
| 4-CF₃ | 5-OCF₃ | iPr | NMe₂ | 4-OCF₃ | 5-OCF₃ | iPr | NMe₂ |
| 4-CF₃ | 5-OCF₃ | Ph | NMe₂ | 4-OCF₃ | 5-OCF₃ | Ph | NMe₂ |
| 4-CF₃ | 5-OCF₃ | 4-F-Ph | NMe₂ | 4-OCF₃ | 5-OCF₃ | 4-F-Ph | NMe₂ |
| 4-CF₃ | 5-OCF₃ | 4-Cl-Ph | NMe₂ | 4-OCF₃ | 5-OCF₃ | 4-Cl-Ph | NMe₂ |
| 4-CF₃ | 4-F | Me | NMe₂ | 4-OCF₃ | 4-F | Me | NMe₂ |
| 4-CF₃ | 4-F | iPr | NMe₂ | 4-OCF₃ | 4-F | iPr | NMe₂ |
| 4-CF₃ | 4-F | Ph | NMe₂ | 4-OCF₃ | 4-F | Ph | NMe₂ |
| 4-CF₃ | 4-F | 4-F-Ph | NMe₂ | 4-OCF₃ | 4-F | 4-F-Ph | NMe₂ |
| 4-CF₃ | 4-F | 4-Cl-Ph | NMe₂ | 4-OCF₃ | 4-F | 4-Cl-Ph | NMe₂ |

TABLE 8

| R¹ | R² | R⁴ | X¹ | R¹ | R² | R⁴ | X¹ |
|---|---|---|---|---|---|---|---|
| 4-CF₃ | 5-F | Me | Cl | 4-OCF₃ | 5-F | Me | Cl |
| 4-CF₃ | 5-F | iPr | Cl | 4-OCF₃ | 5-F | iPr | Cl |
| 4-CF₃ | 5-F | Ph | Cl | 4-OCF₃ | 5-F | Ph | Cl |
| 4-CF₃ | 5-F | 4-F-Ph | Cl | 4-OCF₃ | 5-F | 4-F-Ph | Cl |
| 4-CF₃ | 5-F | 4-Cl-Ph | Cl | 4-OCF₃ | 5-F | 4-Cl-Ph | Cl |
| 4-CF₃ | 5-Cl | Me | Cl | 4-OCF₃ | 5-Cl | Me | Cl |
| 4-CF₃ | 5-Cl | iPr | Cl | 4-OCF₃ | 5-Cl | iPr | Cl |
| 4-CF₃ | 5-Cl | Ph | Cl | 4-OCF₃ | 5-Cl | Ph | Cl |
| 4-CF₃ | 5-Cl | 4-F-Ph | Cl | 4-OCF₃ | 5-Cl | 4-F-Ph | Cl |
| 4-CF₃ | 5-Cl | 4-Cl-Ph | Cl | 4-OCF₃ | 5-Cl | 4-Cl-Ph | Cl |
| 4-CF₃ | 5-CF₃ | Me | Cl | 4-OCF₃ | 5-CF₃ | Me | Cl |
| 4-CF₃ | 5-CF₃ | iPr | Cl | 4-OCF₃ | 5-CF₃ | iPr | Cl |
| 4-CF₃ | 5-CF₃ | Ph | Cl | 4-OCF₃ | 5-CF₃ | Ph | Cl |
| 4-CF₃ | 5-CF₃ | 4-F-Ph | Cl | 4-OCF₃ | 5-CF₃ | 4-F-Ph | Cl |
| 4-CF₃ | 5-CF₃ | 4-Cl-Ph | Cl | 4-OCF₃ | 5-CF₃ | 4-Cl-Ph | Cl |
| 4-CF₃ | 5-OCF₃ | Me | Cl | 4-OCF₃ | 5-OCF₃ | Me | Cl |
| 4-CF₃ | 5-OCF₃ | iPr | Cl | 4-OCF₃ | 5-OCF₃ | iPr | Cl |
| 4-CF₃ | 5-OCF₃ | Ph | Cl | 4-OCF₃ | 5-OCF₃ | Ph | Cl |
| 4-CF₃ | 5-OCF₃ | 4-F-Ph | Cl | 4-OCF₃ | 5-OCF₃ | 4-F-Ph | Cl |
| 4-CF₃ | 5-OCF₃ | 4-Cl-Ph | Cl | 4-OCF₃ | 5-OCF₃ | 4-Cl-Ph | Cl |
| 4-CF₃ | 4-F | Me | Cl | 4-OCF₃ | 4-F | Me | Cl |
| 4-CF₃ | 4-F | iPr | Cl | 4-OCF₃ | 4-F | iPr | Cl |
| 4-CF₃ | 4-F | Ph | Cl | 4-OCF₃ | 4-F | Ph | Cl |
| 4-CF₃ | 4-F | 4-F-Ph | Cl | 4-OCF₃ | 4-F | 4-F-Ph | Cl |
| 4-CF₃ | 4-F | 4-Cl-Ph | Cl | 4-OCF₃ | 4-F | 4-Cl-Ph | Cl |
| 4-CF₃ | 5-F | Me | OMe | 4-OCF₃ | 5-F | Me | OMe |
| 4-CF₃ | 5-F | iPr | OMe | 4-OCF₃ | 5-F | iPr | OMe |
| 4-CF₃ | 5-F | Ph | OMe | 4-OCF₃ | 5-F | Ph | OMe |
| 4-CF₃ | 5-F | 4-F-Ph | OMe | 4-OCF₃ | 5-F | 4-F-Ph | OMe |
| 4-CF₃ | 5-F | 4-Cl-Ph | OMe | 4-OCF₃ | 5-F | 4-Cl-Ph | OMe |
| 4-CF₃ | 5-Cl | Me | OMe | 4-OCF₃ | 5-Cl | Me | OMe |
| 4-CF₃ | 5-Cl | iPr | OMe | 4-OCF₃ | 5-Cl | iPr | OMe |
| 4-CF₃ | 5-Cl | Ph | OMe | 4-OCF₃ | 5-Cl | Ph | OMe |
| 4-CF₃ | 5-Cl | 4-F-Ph | OMe | 4-OCF₃ | 5-Cl | 4-F-Ph | OMe |
| 4-CF₃ | 5-Cl | 4-Cl-Ph | OMe | 4-OCF₃ | 5-Cl | 4-Cl-Ph | OMe |
| 4-CF₃ | 5-CF₃ | Me | OMe | 4-OCF₃ | 5-CF₃ | Me | OMe |
| 4-CF₃ | 5-CF₃ | iPr | OMe | 4-OCF₃ | 5-CF₃ | iPr | OMe |
| 4-CF₃ | 5-CF₃ | Ph | OMe | 4-OCF₃ | 5-CF₃ | Ph | OMe |
| 4-CF₃ | 5-CF₃ | 4-F-Ph | OMe | 4-OCF₃ | 5-CF₃ | 4-F-Ph | OMe |
| 4-CF₃ | 5-CF₃ | 4-Cl-Ph | OMe | 4-OCF₃ | 5-CF₃ | 4-Cl-Ph | OMe |
| 4-CF₃ | 5-OCF₃ | Me | OMe | 4-OCF₃ | 5-OCF₃ | Me | OMe |
| 4-CF₃ | 5-OCF₃ | iPr | OMe | 4-OCF₃ | 5-OCF₃ | iPr | OMe |
| 4-CF₃ | 5-OCF₃ | Ph | OMe | 4-OCF₃ | 5-OCF₃ | Ph | OMe |
| 4-CF₃ | 5-OCF₃ | 4-F-Ph | OMe | 4-OCF₃ | 5-OCF₃ | 4-F-Ph | OMe |
| 4-CF₃ | 5-OCF₃ | 4-Cl-Ph | OMe | 4-OCF₃ | 5-OCF₃ | 4-Cl-Ph | OMe |
| 4-CF₃ | 4-F | Me | OMe | 4-OCF₃ | 4-F | Me | OMe |
| 4-CF₃ | 4-F | iPr | OMe | 4-OCF₃ | 4-F | iPr | OMe |
| 4-CF₃ | 4-F | Ph | OMe | 4-OCF₃ | 4-F | Ph | OMe |
| 4-CF₃ | 4-F | 4-F-Ph | OMe | 4-OCF₃ | 4-F | 4-F-Ph | OMe |
| 4-CF₃ | 4-F | 4-Cl-Ph | OMe | 4-OCF₃ | 4-F | 4-Cl-Ph | OMe |
| 4-CF₃ | 5-F | Me | SMe | 4-OCF₃ | 5-F | Me | SMe |
| 4-CF₃ | 5-F | iPr | SMe | 4-OCF₃ | 5-F | iPr | SMe |
| 4-CF₃ | 5-F | Ph | SMe | 4-OCF₃ | 5-F | Ph | SMe |
| 4-CF₃ | 5-F | 4-F-Ph | SMe | 4-OCF₃ | 5-F | 4-F-Ph | SMe |
| 4-CF₃ | 5-F | 4-Cl-Ph | SMe | 4-OCF₃ | 5-F | 4-Cl-Ph | SMe |
| 4-CF₃ | 5-Cl | Me | SMe | 4-OCF₃ | 5-Cl | Me | SMe |

TABLE 8-continued

| R$^1$ | R$^2$ | R$^4$ | X$^1$ | R$^1$ | R$^2$ | R$^4$ | X$^1$ |
|---|---|---|---|---|---|---|---|
| 4-CF$_3$ | 5-Cl | iPr | SMe | 4-OCF$_3$ | 5-Cl | iPr | SMe |
| 4-CF$_3$ | 5-Cl | Ph | SMe | 4-OCF$_3$ | 5-Cl | Ph | SMe |
| 4-CF$_3$ | 5-Cl | 4-F-Ph | SMe | 4-OCF$_3$ | 5-Cl | 4-F-Ph | SMe |
| 4-CF$_3$ | 5-Cl | 4-Cl-Ph | SMe | 4-OCF$_3$ | 5-Cl | 4-Cl-Ph | SMe |
| 4-CF$_3$ | 5-CF$_3$ | Me | SMe | 4-OCF$_3$ | 5-CF$_3$ | Me | SMe |
| 4-CF$_3$ | 5-CF$_3$ | iPr | SMe | 4-OCF$_3$ | 5-CF$_3$ | iPr | SMe |
| 4-CF$_3$ | 5-CF$_3$ | Ph | SMe | 4-OCF$_3$ | 5-CF$_3$ | Ph | SMe |
| 4-CF$_3$ | 5-CF$_3$ | 4-F-Ph | SMe | 4-OCF$_3$ | 5-CF$_3$ | 4-F-Ph | SMe |
| 4-CF$_3$ | 5-CF$_3$ | 4-Cl-Ph | SMe | 4-OCF$_3$ | 5-CF$_3$ | 4-Cl-Ph | SMe |
| 4-CF$_3$ | 5-OCF$_3$ | Me | SMe | 4-OCF$_3$ | 5-OCF$_3$ | Me | SMe |
| 4-CF$_3$ | 5-OCF$_3$ | iPr | SMe | 4-OCF$_3$ | 5-OCF$_3$ | iPr | SMe |
| 4-CF$_3$ | 5-OCF$_3$ | Ph | SMe | 4-OCF$_3$ | 5-OCF$_3$ | Ph | SMe |
| 4-CF$_3$ | 5-OCF$_3$ | 4-F-Ph | SMe | 4-OCF$_3$ | 5-OCF$_3$ | 4-F-Ph | SMe |
| 4-CF$_3$ | 5-OCF$_3$ | 4-Cl-Ph | SMe | 4-OCF$_3$ | 5-OCF$_3$ | 4-Cl-Ph | SMe |
| 4-CF$_3$ | 4-F | Me | SMe | 4-OCF$_3$ | 4-F | Me | SMe |
| 4-CF$_3$ | 4-F | iPr | SMe | 4-OCF$_3$ | 4-F | iPr | SMe |
| 4-CF$_3$ | 4-F | Ph | SMe | 4-OCF$_3$ | 4-F | Ph | SMe |
| 4-CF$_3$ | 4-F | 4-F-Ph | SMe | 4-OCF$_3$ | 4-F | 4-F-Ph | SMe |
| 4-CF$_3$ | 4-F | 4-Cl-Ph | SMe | 4-OCF$_3$ | 4-F | 4-Cl-Ph | SMe |
| 4-CF$_3$ | 5-F | Me | NMe$_2$ | 4-OCF$_3$ | 5-F | Me | NMe$_2$ |
| 4-CF$_3$ | 5-F | iPr | NMe$_2$ | 4-OCF$_3$ | 5-F | iPr | NMe$_2$ |
| 4-CF$_3$ | 5-F | Ph | NMe$_2$ | 4-OCF$_3$ | 5-F | Ph | NMe$_2$ |
| 4-CF$_3$ | 5-F | 4-F-Ph | NMe$_2$ | 4-OCF$_3$ | 5-F | 4-F-Ph | NMe$_2$ |
| 4-CF$_3$ | 5-F | 4-Cl-Ph | NMe$_2$ | 4-OCF$_3$ | 5-F | 4-Cl-Ph | NMe$_2$ |
| 4-CF$_3$ | 5-Cl | Me | NMe$_2$ | 4-OCF$_3$ | 5-Cl | Me | NMe$_2$ |
| 4-CF$_3$ | 5-Cl | iPr | NMe$_2$ | 4-OCF$_3$ | 5-Cl | iPr | NMe$_2$ |
| 4-CF$_3$ | 5-Cl | Ph | NMe$_2$ | 4-OCF$_3$ | 5-Cl | Ph | NMe$_2$ |
| 4-CF$_3$ | 5-Cl | 4-F-Ph | NMe$_2$ | 4-OCF$_3$ | 5-Cl | 4-F-Ph | NMe$_2$ |
| 4-CF$_3$ | 5-Cl | 4-Cl-Ph | NMe$_2$ | 4-OCF$_3$ | 5-Cl | 4-Cl-Ph | NMe$_2$ |
| 4-CF$_3$ | 5-CF$_3$ | Me | NMe$_2$ | 4-OCF$_3$ | 5-CF$_3$ | Me | NMe$_2$ |
| 4-CF$_3$ | 5-CF$_3$ | iPr | NMe$_2$ | 4-OCF$_3$ | 5-CF$_3$ | iPr | NMe$_2$ |
| 4-CF$_3$ | 5-CF$_3$ | Ph | NMe$_2$ | 4-OCF$_3$ | 5-CF$_3$ | Ph | NMe$_2$ |
| 4-CF$_3$ | 5-CF$_3$ | 4-F-Ph | NMe$_2$ | 4-OCF$_3$ | 5-CF$_3$ | 4-F-Ph | NMe$_2$ |
| 4-CF$_3$ | 5-CF$_3$ | 4-Cl-Ph | NMe$_2$ | 4-OCF$_3$ | 5-CF$_3$ | 4-Cl-Ph | NMe$_2$ |
| 4-CF$_3$ | 5-OCF$_3$ | Me | NMe$_2$ | 4-OCF$_3$ | 5-OCF$_3$ | Me | NMe$_2$ |
| 4-CF$_3$ | 5-OCF$_3$ | iPr | NMe$_2$ | 4-OCF$_3$ | 5-OCF$_3$ | iPr | NMe$_2$ |
| 4-CF$_3$ | 5-OCF$_3$ | Ph | NMe$_2$ | 4-OCF$_3$ | 5-OCF$_3$ | Ph | NMe$_2$ |
| 4-CF$_3$ | 5-OCF$_3$ | 4-F-Ph | NMe$_2$ | 4-OCF$_3$ | 5-OCF$_3$ | 4-F-Ph | NMe$_2$ |
| 4-CF$_3$ | 5-OCF$_3$ | 4-Cl-Ph | NMe$_2$ | 4-OCF$_3$ | 5-OCF$_3$ | 4-Cl-Ph | NMe$_2$ |
| 4-CF$_3$ | 4-F | Me | NMe$_2$ | 4-OCF$_3$ | 4-F | Me | NMe$_2$ |
| 4-CF$_3$ | 4-F | iPr | NMe$_2$ | 4-OCF$_3$ | 4-F | iPr | NMe$_2$ |
| 4-CF$_3$ | 4-F | Ph | NMe$_2$ | 4-OCF$_3$ | 4-F | Ph | NMe$_2$ |
| 4-CF$_3$ | 4-F | 4-F-Ph | NMe$_2$ | 4-OCF$_3$ | 4-F | 4-F-Ph | NMe$_2$ |
| 4-CF$_3$ | 4-F | 4-Cl-Ph | NMe$_2$ | 4-OCF$_3$ | 4-F | 4-Cl-Ph | NMe$_2$ |

TABLE 9

| R$^1$ | R$^2$ | R$^3$ | R$^5$ | X$^1$ | R$^1$ | R$^2$ | R$^3$ | R$^{45}$ | X$^1$ |
|---|---|---|---|---|---|---|---|---|---|
| 4-CF$_3$ | 4-Cl | CO$_2$Me | H | Cl | 4-OCF$_3$ | 4-Cl | 4-Cl-Ph | H | NMe$_2$ |
| 4-CF$_3$ | 4-Cl | CO$_2$Me | H | OMe | 4-CF$_3$ | 4-Cl | CO$_2$Me | Me | Cl |
| 4-CF$_3$ | 4-Cl | CO$_2$Me | H | SMe | 4-CF$_3$ | 4-Cl | CO$_2$Me | Me | OMe |
| 4-CF$_3$ | 4-Cl | CO$_2$Me | H | NMe$_2$ | 4-CF$_3$ | 4-Cl | CO$_2$Me | Me | SMe |
| 4-CF$_3$ | 4-CF$_3$ | CO$_2$Me | H | Cl | 4-CF$_3$ | 4-Cl | CO$_2$Me | Me | NMe$_2$ |
| 4-CF$_3$ | 4-CF$_3$ | CO$_2$Me | H | OMe | 4-CF$_3$ | 4-CF$_3$ | CO$_2$Me | Me | Cl |
| 4-CF$_3$ | 4-CF$_3$ | CO$_2$Me | H | SMe | 4-CF$_3$ | 4-CF$_3$ | CO$_2$Me | Me | OMe |
| 4-CF$_3$ | 4-CF$_3$ | CO$_2$Me | H | NMe$_2$ | 4-CF$_3$ | 4-CF$_3$ | CO$_2$Me | Me | SMe |
| 4-CF$_3$ | 4-Cl | 4-Cl-Ph | H | Cl | 4-CF$_3$ | 4-CF$_3$ | CO$_2$Me | Me | NMe$_2$ |
| 4-CF$_3$ | 4-Cl | 4-Cl-Ph | H | OMe | 4-CF$_3$ | 4-Cl | CO$_2$Me | Me | Cl |
| 4-CF$_3$ | 4-Cl | 4-Cl-Ph | H | SMe | 4-CF$_3$ | 4-Cl | CO$_2$Me | Me | OMe |
| 4-CF$_3$ | 4-Cl | 4-Cl-Ph | H | NMe$_2$ | 4-CF$_3$ | 4-Cl | CO$_2$Me | Me | SMe |
| 4-CF$_3$ | 4-CF$_3$ | 4-Cl-Ph | H | Cl | 4-CF$_3$ | 4-Cl | CO$_2$Me | Me | NMe$_2$ |
| 4-CF$_3$ | 4-CF$_3$ | 4-Cl-Ph | H | OMe | 4-CF$_3$ | 4-CF$_3$ | CO$_2$Me | Me | Cl |
| 4-CF$_3$ | 4-CF$_3$ | 4-Cl-Ph | H | SMe | 4-CF$_3$ | 4-CF$_3$ | CO$_2$Me | Me | OMe |
| 4-CF$_3$ | 4-CF$_3$ | 4-Cl-Ph | H | NMe$_2$ | 4-CF$_3$ | 4-CF$_3$ | CO$_2$Me | Me | SMe |
| 4-OCF$_3$ | 4-Cl | CO$_2$Me | H | Cl | 4-CF$_3$ | 4-CF$_3$ | CO$_2$Me | Me | NMe$_2$ |
| 4-OCF$_3$ | 4-Cl | CO$_2$Me | H | OMe | | | | | |
| 4-OCF$_3$ | 4-Cl | CO$_2$Me | H | SMe | | | | | |
| 4-OCF$_3$ | 4-Cl | CO$_2$Me | H | NMe$_2$ | | | | | |
| 4-OCF$_3$ | 4-CF$_3$ | CO$_2$Me | H | Cl | | | | | |
| 4-OCF$_3$ | 4-CF$_3$ | CO$_2$Me | H | OMe | | | | | |
| 4-OCF$_3$ | 4-CF$_3$ | CO$_2$Me | H | SMe | | | | | |
| 4-OCF$_3$ | 4-CF$_3$ | CO$_2$Me | H | NMe$_2$ | | | | | |
| 4-OCF$_3$ | 4-Cl | 4-Cl-Ph | H | Cl | | | | | |
| 4-OCF$_3$ | 4-Cl | 4-Cl-Ph | H | OMe | | | | | |
| 4-OCF$_3$ | 4-Cl | 4-Cl-Ph | H | SMe | | | | | |

TABLE 10

| R¹ | R² | R³ | R⁵ | X¹ | R¹ | R² | R³ | R⁵ | X¹ |
|---|---|---|---|---|---|---|---|---|---|
| 4-CF₃ | 4-Cl | CO₂Me | H | Cl | 4-OCF₃ | 4-CF₃ | 4-F-Ph | H | NMe₂ |
| 4-CF₃ | 4-Cl | CO₂Me | H | OMe | 4-CF₃ | 4-Cl | CO₂Me | Me | Cl |
| 4-CF₃ | 4-Cl | CO₂Me | H | SMe | 4-CF₃ | 4-Cl | CO₂Me | Me | OMe |
| 4-CF₃ | 4-Cl | CO₂Me | H | NMe₂ | 4-CF₃ | 4-Cl | CO₂Me | Me | SMe |
| 4-CF₃ | 4-CF₃ | CO₂Me | H | Cl | 4-CF₃ | 4-Cl | CO₂Me | Me | NMe₂ |
| 4-CF₃ | 4-CF₃ | CO₂Me | H | OMe | 4-CF₃ | 4-CF₃ | CO₂Me | Me | Cl |
| 4-CF₃ | 4-CF₃ | CO₂Me | H | SMe | 4-CF₃ | 4-CF₃ | CO₂Me | Me | OMe |
| 4-CF₃ | 4-CF₃ | CO₂Me | H | NMe₂ | 4-CF₃ | 4-CF₃ | CO₂Me | Me | SMe |
| 4-CF₃ | 4-Cl | 4-F-Ph | H | Cl | 4-CF₃ | 4-CF₃ | CO₂Me | Me | NMe₂ |
| 4-CF₃ | 4-Cl | 4-F-Ph | H | OMe | 4-CF₃ | 4-Cl | CO₂Me | Me | Cl |
| 4-CF₃ | 4-Cl | 4-F-Ph | H | SMe | 4-CF₃ | 4-Cl | CO₂Me | Me | OMe |
| 4-CF₃ | 4-Cl | 4-F-Ph | H | NMe₂ | 4-CF₃ | 4-Cl | CO₂Me | Me | SMe |
| 4-CF₃ | 4-CF₃ | 4-F-Ph | H | Cl | 4-CF₃ | 4-Cl | CO₂Me | Me | NMe₂ |
| 4-CF₃ | 4-CF₃ | 4-F-Ph | H | OMe | 4-CF₃ | 4-CF₃ | CO₂Me | Me | Cl |
| 4-CF₃ | 4-CF₃ | 4-F-Ph | H | SMe | 4-CF₃ | 4-CF₃ | CO₂Me | Me | OMe |
| 4-CF₃ | 4-CF₃ | 4-F-Ph | H | NMe₂ | 4-CF₃ | 4-CF₃ | CO₂Me | Me | SMe |
| 4-OCF₃ | 4-Cl | CO₂Me | H | Cl | 4-CF₃ | 4-CF₃ | CO₂Me | Me | NMe₂ |
| 4-OCF₃ | 4-Cl | CO₂Me | H | OMe | | | | | |
| 4-OCF₃ | 4-Cl | CO₂Me | H | SMe | | | | | |
| 4-OCF₃ | 4-Cl | CO₂Me | H | NMe₂ | | | | | |
| 4-OCF₃ | 4-CF₃ | CO₂Me | H | Cl | | | | | |
| 4-OCF₃ | 4-CF₃ | CO₂Me | H | OMe | | | | | |
| 4-OCF₃ | 4-CF₃ | CO₂Me | H | SMe | | | | | |
| 4-OCF₃ | 4-CF₃ | CO₂Me | H | NMe₂ | | | | | |
| 4-OCF₃ | 4-Cl | 4-F-Ph | H | Cl | | | | | |
| 4-OCF₃ | 4-Cl | 4-F-Ph | H | OMe | | | | | |
| 4-OCF₃ | 4-Cl | 4-F-Ph | H | SMe | | | | | |
| 4-OCF₃ | 4-Cl | 4-F-Ph | H | NMe₂ | | | | | |
| 4-OCF₃ | 4-CF₃ | 4-F-Ph | H | Cl | | | | | |
| 4-OCF₃ | 4-CF₃ | 4-F-Ph | H | OMe | | | | | |
| 4-OCF₃ | 4-CF₃ | 4-F-Ph | H | SMe | | | | | |

TABLE 11

| R² | R³ | X¹ | R² | R³ | X¹ |
|---|---|---|---|---|---|
| 4-Cl | iPr | SCH₂Ph | 4-CF₃ | CO₂Me | SCH₂Ph |
| 4-Cl | iPr | SCH₂CHCH₂ | 4-CF₃ | CO₂Me | SCH₂CHCH₂ |
| 4-Cl | iPr | SCH₂CCH | 4-CF₃ | CO₂Me | SCH₂CCH |
| 4-Cl | iPr | SCF₃ | 4-CF₃ | CO₂Me | SCF₃ |
| 4-Cl | iPr | SCH₂CF₃ | 4-CF₃ | CO₂Me | SCH₂CF₃ |
| 4-Cl | iPr | SCH₂CO₂Me | 4-CF₃ | CO₂Me | SCH₂CO₂Me |
| 4-Cl | iPr | SCH₂CN | 4-CF₃ | CO₂Me | SCH₂CN |
| 4-Cl | iPr | SCH₂NO₂ | 4-CF₃ | CO₂Me | SCH₂NO₂ |
| 4-Cl | iPr | SCH₂CH₂OMe | 4-CF₃ | CO₂Me | SCH₂CH₂OMe |
| 4-Cl | iPr | SCH₂CH₂SMe | 4-CF₃ | CO₂Me | SCH₂CH₂SMe |
| 4-Cl | iPr | OCH₂Ph | 4-CF₃ | CO₂Me | OCH₂Ph |
| 4-Cl | iPr | OCH₂CHCH₂ | 4-CF₃ | CO₂Me | OCH₂CHCH₂ |
| 4-Cl | iPr | OCH₂CCH | 4-CF₃ | CO₂Me | OCH₂CCH |
| 4-Cl | iPr | OCH₂CF₃ | 4-CF₃ | CO₂Me | OCH₂CF₃ |
| 4-Cl | iPr | OCH₂CO₂Me | 4-CF₃ | CO₂Me | OCH₂CO₂Me |
| 4-Cl | iPr | OCH₂CN | 4-CF₃ | CO₂Me | OCH₂CN |
| 4-Cl | iPr | OCH₂CH₂OMe | 4-CF₃ | CO₂Me | OCH₂CH₂OMe |
| 4-Cl | iPr | OCH₂CH₂SMe | 4-CF₃ | CO₂Me | OCH₂CH₂SMe |
| 4-Cl | iPr | NMe₂ | 4-CF₃ | CO₂Me | NMe₂ |
| 4-Cl | iPr | NH-4-Cl-Ph | 4-CF₃ | CO₂Me | NH-4-Cl-Ph |
| 4-Cl | iPr | NH-4-CF₃-Ph | 4-CF₃ | CO₂Me | NH-4-CF₃-Ph |
| 4-Cl | iPr | N(CH₂)₄ | 4-CF₃ | CO₂Me | N(CH₂)₄ |
| 4-Cl | iPr | N(CH₂)₅ | 4-CF₃ | CO₂Me | N(CH₂)₅ |
| 4-Cl | iPr | N(—CH₂CH₂OCH₂CH₂—) | 4-CF₃ | CO₂Me | N(—CH₂CH₂OCH₂CH₂—) |

TABLE 12

| R¹ | R² | V | X² | R¹ | R² | V | X² |
|---|---|---|---|---|---|---|---|
| 4-CF₃ | 7-F | CH₂ | OH | 4-OCF₃ | 7-F | CH₂ | OH |
| 4-CF₃ | 7-F | CH₂ | OMe | 4-OCF₃ | 7-F | CH₂ | OMe |
| 4-CF₃ | 7-F | CH₂ | OCONHMe | 4-OCF₃ | 7-F | CH₂ | OCONHMe |
| 4-CF₃ | 7-F | CH₂ | CN | 4-OCF₃ | 7-F | CH₂ | CN |
| 4-CF₃ | 7-F | CH₂ | NMe₂ | 4-OCF₃ | 7-F | CH₂ | NMe₂ |
| 4-CF₃ | 7-Cl | CH₂ | OH | 4-OCF₃ | 7-Cl | CH₂ | OH |
| 4-CF₃ | 7-Cl | CH₂ | OMe | 4-OCF₃ | 7-Cl | CH₂ | OMe |
| 4-CF₃ | 7-Cl | CH₂ | OCONHMe | 4-OCF₃ | 7-Cl | CH₂ | OCONHMe |
| 4-CF₃ | 7-Cl | CH₂ | CN | 4-OCF₃ | 7-Cl | CH₂ | CN |
| 4-CF₃ | 7-Cl | CH₂ | NMe₂ | 4-OCF₃ | 7-Cl | CH₂ | NMe₂ |
| 4-CF₃ | 7-CF₃ | CH₂ | OH | 4-OCF₃ | 7-CF₃ | CH₂ | OH |
| 4-CF₃ | 7-CF₃ | CH₂ | OMe | 4-OCF₃ | 7-CF₃ | CH₂ | OMe |
| 4-CF₃ | 7-CF₃ | CH₂ | OCONHMe | 4-OCF₃ | 7-CF₃ | CH₂ | OCONHMe |
| 4-CF₃ | 7-CF₃ | CH₂ | CN | 4-OCF₃ | 7-CF₃ | CH₂ | CN |
| 4-CF₃ | 7-CF₃ | CH₂ | NMe₂ | 4-OCF₃ | 7-CF₃ | CH₂ | NMe₂ |

TABLE 12-continued

| R¹ | R² | V | X² | R¹ | R² | V | X² |
|---|---|---|---|---|---|---|---|
| 4-CF₃ | 7-OCF₃ | CH₂ | OH | 4-OCF₃ | 7-OCF₃ | CH₂ | OH |
| 4-CF₃ | 7-OCF₃ | CH₂ | OMe | 4-OCF₃ | 7-OCF₃ | CH₂ | OMe |
| 4-CF₃ | 7-OCF₃ | CH₂ | OCONHMe | 4-OCF₃ | 7-OCF₃ | CH₂ | OCONHMe |
| 4-CF₃ | 7-OCF₃ | CH₂ | CN | 4-OCF₃ | 7-OCF₃ | CH₂ | CN |
| 4-CF₃ | 7-OCF₃ | CH₂ | NMe₂ | 4-OCF₃ | 7-OCF₃ | CH₂ | NMe₂ |
| 4-CF₃ | 6-F | CH₂ | OH | 4-OCF₃ | 6-F | CH₂ | OH |
| 4-CF₃ | 6-F | CH₂ | OMe | 4-OCF₃ | 6-F | CH₂ | OMe |
| 4-CF₃ | 6-F | CH₂ | OCONHMe | 4-OCF₃ | 6-F | CH₂ | OCONHMe |
| 4-CF₃ | 6-F | CH₂ | CN | 4-OCF₃ | 6-F | CH₂ | CN |
| 4-CF₃ | 6-F | CH₂ | NMe₂ | 4-OCF₃ | 6-F | CH₂ | NMe₂ |
| 4-CF₃ | 7-F | O | OH | 4-OCF₃ | 7-F | O | OH |
| 4-CF₃ | 7-F | O | OMe | 4-OCF₃ | 7-F | O | OMe |
| 4-CF₃ | 7-F | O | OCONHMe | 4-OCF₃ | 7-F | O | OCONHMe |
| 4-CF₃ | 7-F | O | CN | 4-OCF₃ | 7-F | O | CN |
| 4-CF₃ | 7-F | O | NMe₂ | 4-OCF₃ | 7-F | O | NMe₂ |
| 4-CF₃ | 7-Cl | O | OH | 4-OCF₃ | 7-Cl | O | OH |
| 4-CF₃ | 7-Cl | O | OMe | 4-OCF₃ | 7-Cl | O | OMe |
| 4-CF₃ | 7-Cl | O | OCONHMe | 4-OCF₃ | 7-Cl | O | OCONHMe |
| 4-CF₃ | 7-Cl | O | CN | 4-OCF₃ | 7-Cl | O | CN |
| 4-CF₃ | 7-Cl | O | NMe₂ | 4-OCF₃ | 7-Cl | O | NMe₂ |
| 4-CF₃ | 7-CF₃ | O | OH | 4-OCF₃ | 7-CF₃ | O | OH |
| 4-CF₃ | 7-CF₃ | O | OMe | 4-OCF₃ | 7-CF₃ | O | OMe |
| 4-CF₃ | 7-CF₃ | O | OCONHMe | 4-OCF₃ | 7-CF₃ | O | OCONHMe |
| 4-CF₃ | 7-CF₃ | O | CN | 4-OCF₃ | 7-CF₃ | O | CN |
| 4-CF₃ | 7-CF₃ | O | NMe₂ | 4-OCF₃ | 7-CF₃ | O | NMe₂ |
| 4-CF₃ | 7-OCF₃ | O | OH | 4-OCF₃ | 7-OCF₃ | O | OH |
| 4-CF₃ | 7-OCF₃ | O | OMe | 4-OCF₃ | 7-OCF₃ | O | OMe |
| 4-CF₃ | 7-OCF₃ | O | OCONHMe | 4-OCF₃ | 7-OCF₃ | O | OCONHMe |
| 4-CF₃ | 7-OCF₃ | O | CN | 4-OCF₃ | 7-OCF₃ | O | CN |
| 4-CF₃ | 7-OCF₃ | O | NMe₂ | 4-OCF₃ | 7-OCF₃ | O | NMe₂ |
| 4-CF₃ | 6-F | O | OH | 4-OCF₃ | 6-F | O | OH |
| 4-CF₃ | 6-F | O | OMe | 4-OCF₃ | 6-F | O | OMe |
| 4-CF₃ | 6-F | O | OCONHMe | 4-OCF₃ | 6-F | O | OCONHMe |
| 4-CF₃ | 6-F | O | CN | 4-OCF₃ | 6-F | O | CN |
| 4-CF₃ | 6-F | O | NMe₂ | 4-OCF₃ | 6-F | O | NMe₂ |
| 4-CF₃ | 7-F | NMe | OH | 4-OCF₃ | 7-F | NMe | OH |
| 4-CF₃ | 7-F | NMe | OMe | 4-OCF₃ | 7-F | NMe | OMe |
| 4-CF₃ | 7-F | NMe | OCONHMe | 4-OCF₃ | 7-F | NMe | OCONHMe |
| 4-CF₃ | 7-F | NMe | CN | 4-OCF₃ | 7-F | NMe | CN |
| 4-CF₃ | 7-F | NMe | NMe₂ | 4-OCF₃ | 7-F | NMe | NMe₂ |
| 4-CF₃ | 7-Cl | NMe | OH | 4-OCF₃ | 7-Cl | NMe | OH |
| 4-CF₃ | 7-Cl | NMe | OMe | 4-OCF₃ | 7-Cl | NMe | OMe |
| 4-CF₃ | 7-Cl | NMe | OCONHMe | 4-OCF₃ | 7-Cl | NMe | OCONHMe |
| 4-CF₃ | 7-Cl | NMe | CN | 4-OCF₃ | 7-Cl | NMe | CN |
| 4-CF₃ | 7-Cl | NMe | NMe₂ | 4-OCF₃ | 7-Cl | NMe | NMe₂ |
| 4-CF₃ | 7-CF₃ | NMe | OH | 4-OCF₃ | 7-CF₃ | NMe | OH |
| 4-CF₃ | 7-CF₃ | NMe | OMe | 4-OCF₃ | 7-CF₃ | NMe | OMe |
| 4-CF₃ | 7-CF₃ | NMe | OCONHMe | 4-OCF₃ | 7-CF₃ | NMe | OCONHMe |
| 4-CF₃ | 7-CF₃ | NMe | CN | 4-OCF₃ | 7-CF₃ | NMe | CN |
| 4-CF₃ | 7-CF₃ | NMe | NMe₂ | 4-OCF₃ | 7-CF₃ | NMe | NMe₂ |
| 4-CF₃ | 7-OCF₃ | NMe | OH | 4-OCF₃ | 7-OCF₃ | NMe | OH |
| 4-CF₃ | 7-OCF₃ | NMe | OMe | 4-OCF₃ | 7-OCF₃ | NMe | OMe |
| 4-CF₃ | 7-OCF₃ | NMe | OCONHMe | 4-OCF₃ | 7-OCF₃ | NMe | OCONHMe |
| 4-CF₃ | 7-OCF₃ | NMe | CN | 4-OCF₃ | 7-OCF₃ | NMe | CN |
| 4-CF₃ | 7-OCF₃ | NMe | NMe₂ | 4-OCF₃ | 7-OCF₃ | NMe | NMe₂ |
| 4-CF₃ | 6-F | NMe | OH | 4-OCF₃ | 6-F | NMe | OH |
| 4-CF₃ | 6-F | NMe | OMe | 4-OCF₃ | 6-F | NMe | OMe |
| 4-CF₃ | 6-F | NMe | OCONHMe | 4-OCF₃ | 6-F | NMe | OCONHMe |
| 4-CF₃ | 6-F | NMe | CN | 4-OCF₃ | 6-F | NMe | CN |
| 4-CF₃ | 6-F | NMe | NMe₂ | 4-OCF₃ | 6-F | NMe | NMe₂ |
| 4-CF₃ | 7-F | NSO₂Me | OH | 4-OCF₃ | 7-F | NSO₂Me | OH |
| 4-CF₃ | 7-F | NSO₂Me | OMe | 4-OCF₃ | 7-F | NSO₂Me | OMe |
| 4-CF₃ | 7-F | NSO₂Me | OCONHMe | 4-OCF₃ | 7-F | NSO₂Me | OCONHMe |
| 4-CF₃ | 7-F | NSO₂Me | CN | 4-OCF₃ | 7-F | NSO₂Me | CN |
| 4-CF₃ | 7-F | NSO₂Me | NMe₂ | 4-OCF₃ | 7-F | NSO₂Me | NMe₂ |
| 4-CF₃ | 7-Cl | NSO₂Me | OH | 4-OCF₃ | 7-Cl | NSO₂Me | OH |
| 4-CF₃ | 7-Cl | NSO₂Me | OMe | 4-OCF₃ | 7-Cl | NSO₂Me | OMe |
| 4-CF₃ | 7-Cl | NSO₂Me | OCONHMe | 4-OCF₃ | 7-Cl | NSO₂Me | OCONHMe |
| 4-CF₃ | 7-Cl | NSO₂Me | CN | 4-OCF₃ | 7-Cl | NSO₂Me | CN |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | OH | 4-OCF₃ | 7-CF₃ | NSO₂Me | OH |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | OCONHMe | 4-OCF₃ | 7-CF₃ | NSO₂Me | OCONHMe |
| 4-CF₃ | 7-CF₃ | NSO₂Me | CN | 4-OCF₃ | 7-CF₃ | NSO₂Me | CN |
| 4-CF₃ | 7-CF₃ | NSO₂Me | NMe₂ | 4-OCF₃ | 7-CF₃ | NSO₂Me | NMe₂ |
| 4-CF₃ | 7-OCF₃ | NSO₂Me | OH | 4-OCF₃ | 7-OCF₃ | NSO₂Me | OH |
| 4-CF₃ | 7-OCF₃ | NSO₂Me | OMe | 4-OCF₃ | 7-OCF₃ | NSO₂Me | OMe |
| 4-CF₃ | 7-OCF₃ | NSO₂Me | OCONHMe | 4-OCF₃ | 7-OCF₃ | NSO₂Me | OCONHMe |
| 4-CF₃ | 7-OCF₃ | NSO₂Me | CN | 4-OCF₃ | 7-OCF₃ | NSO₂Me | CN |
| 4-CF₃ | 7-OCF₃ | NSO₂Me | NMe₂ | 4-OCF₃ | 7-OCF₃ | NSO₂Me | NMe₂ |
| 4-CF₃ | 6-F | NSO₂Me | OH | 4-OCF₃ | 6-F | NSO₂Me | OH |

TABLE 12-continued

| R¹ | R² | V | X² | R¹ | R² | V | X² |
|---|---|---|---|---|---|---|---|
| 4-CF₃ | 6-F | NSO₂Me | OMe | 4-OCF₃ | 6-F | NSO₂Me | OMe |
| 4-CF₃ | 6-F | NSO₂Me | OCONHMe | 4-OCF₃ | 6-F | NSO₂Me | OCONHMe |
| 4-CF₃ | 6-F | NSO₂Me | CN | 4-OCF₃ | 6-F | NSO₂Me | CN |
| 4-CF₃ | 6-F | NSO₂Me | NMe₂ | 4-OCF₃ | 6-F | NSO₂Me | NMe₂ |

TABLE 13

| R¹ | R² | V | X² | R¹ | R² | V | X² |
|---|---|---|---|---|---|---|---|
| 4-CF₃ | 7-F | CH₂ | OH | 4-OCF₃ | 7-F | CH₂ | OH |
| 4-CF₃ | 7-F | CH₂ | OMe | 4-OCF₃ | 7-F | CH₂ | OMe |
| 4-CF₃ | 7-F | CH₂ | OCONHMe | 4-OCF₃ | 7-F | CH₂ | OCONHMe |
| 4-CF₃ | 7-F | CH₂ | CN | 4-OCF₃ | 7-F | CH₂ | CN |
| 4-CF₃ | 7-F | CH₂ | NMe₂ | 4-OCF₃ | 7-F | CH₂ | NMe₂ |
| 4-CF₃ | 7-Cl | CH₂ | OH | 4-OCF₃ | 7-Cl | CH₂ | OH |
| 4-CF₃ | 7-Cl | CH₂ | OMe | 4-OCF₃ | 7-Cl | CH₂ | OMe |
| 4-CF₃ | 7-Cl | CH₂ | OCONHMe | 4-OCF₃ | 7-Cl | CH₂ | OCONHMe |
| 4-CF₃ | 7-Cl | CH₂ | CN | 4-OCF₃ | 7-Cl | CH₂ | CN |
| 4-CF₃ | 7-Cl | CH₂ | NMe₂ | 4-OCF₃ | 7-Cl | CH₂ | NMe₂ |
| 4-CF₃ | 7-CF₃ | CH₂ | OH | 4-OCF₃ | 7-CF₃ | CH₂ | OH |
| 4-CF₃ | 7-CF₃ | CH₂ | OMe | 4-OCF₃ | 7-CF₃ | CH₂ | OMe |
| 4-CF₃ | 7-CF₃ | CH₂ | OCONHMe | 4-OCF₃ | 7-CF₃ | CH₂ | OCONHMe |
| 4-CF₃ | 7-CF₃ | CH₂ | CN | 4-OCF₃ | 7-CF₃ | CH₂ | CN |
| 4-CF₃ | 7-CF₃ | CH₂ | NMe₂ | 4-OCF₃ | 7-CF₃ | CH₂ | NMe₂ |
| 4-CF₃ | 7-OCF₃ | CH₂ | OH | 4-OCF₃ | 7-OCF₃ | CH₂ | OH |
| 4-CF₃ | 7-OCF₃ | CH₂ | OMe | 4-OCF₃ | 7-OCF₃ | CH₂ | OMe |
| 4-CF₃ | 7-OCF₃ | CH₂ | OCONHMe | 4-OCF₃ | 7-OCF₃ | CH₂ | OCONHMe |
| 4-CF₃ | 7-OCF₃ | CH₂ | CN | 4-OCF₃ | 7-OCF₃ | CH₂ | CN |
| 4-CF₃ | 7-OCF₃ | CH₂ | NMe₂ | 4-OCF₃ | 7-OCF₃ | CH₂ | NMe₂ |
| 4-CF₃ | 6-F | CH₂ | OH | 4-OCF₃ | 6-F | CH₂ | OH |
| 4-CF₃ | 6-F | CH₂ | OMe | 4-OCF₃ | 6-F | CH₂ | OMe |
| 4-CF₃ | 6-F | CH₂ | OCONHMe | 4-OCF₃ | 6-F | CH₂ | OCONHMe |
| 4-CF₃ | 6-F | CH₂ | CN | 4-OCF₃ | 6-F | CH₂ | CN |
| 4-CF₃ | 6-F | CH₂ | NMe₂ | 4-OCF₃ | 6-F | CH₂ | NMe₂ |
| 4-CF₃ | 7-F | O | OH | 4-OCF₃ | 7-F | O | OH |
| 4-CF₃ | 7-F | O | OMe | 4-OCF₃ | 7-F | O | OMe |
| 4-CF₃ | 7-F | O | OCONHMe | 4-OCF₃ | 7-F | O | OCONHMe |
| 4-CF₃ | 7-F | O | CN | 4-OCF₃ | 7-F | O | CN |
| 4-CF₃ | 7-F | O | NMe₂ | 4-OCF₃ | 7-F | O | NMe₂ |
| 4-CF₃ | 7-Cl | O | OH | 4-OCF₃ | 7-Cl | O | OH |
| 4-CF₃ | 7-Cl | O | OMe | 4-OCF₃ | 7-Cl | O | OMe |
| 4-CF₃ | 7-Cl | O | OCONHMe | 4-OCF₃ | 7-Cl | O | OCONHMe |
| 4-CF₃ | 7-Cl | O | CN | 4-OCF₃ | 7-Cl | O | CN |
| 4-CF₃ | 7-Cl | O | NMe₂ | 4-OCF₃ | 7-Cl | O | NMe₂ |
| 4-CF₃ | 7-CF₃ | O | OH | 4-OCF₃ | 7-CF₃ | O | OH |
| 4-CF₃ | 7-CF₃ | O | OMe | 4-OCF₃ | 7-CF₃ | O | OMe |
| 4-CF₃ | 7-CF₃ | O | OCONHMe | 4-OCF₃ | 7-CF₃ | O | OCONHMe |
| 4-CF₃ | 7-CF₃ | O | CN | 4-OCF₃ | 7-CF₃ | O | CN |
| 4-CF₃ | 7-CF₃ | O | NMe₂ | 4-OCF₃ | 7-CF₃ | O | NMe₂ |
| 4-CF₃ | 7-OCF₃ | O | OH | 4-OCF₃ | 7-OCF₃ | O | OH |
| 4-CF₃ | 7-OCF₃ | O | OMe | 4-OCF₃ | 7-OCF₃ | O | OMe |
| 4-CF₃ | 7-OCF₃ | O | OCONHMe | 4-OCF₃ | 7-OCF₃ | O | OCONHMe |
| 4-CF₃ | 7-OCF₃ | O | CN | 4-OCF₃ | 7-OCF₃ | O | CN |
| 4-CF₃ | 7-OCF₃ | O | NMe₂ | 4-OCF₃ | 7-OCF₃ | O | NMe₂ |
| 4-CF₃ | 6-F | O | OH | 4-OCF₃ | 6-F | O | OH |
| 4-CF₃ | 6-F | O | OMe | 4-OCF₃ | 6-F | O | OMe |
| 4-CF₃ | 6-F | O | OCONHMe | 4-OCF₃ | 6-F | O | OCONHMe |
| 4-CF₃ | 6-F | O | CN | 4-OCF₃ | 6-F | O | CN |
| 4-CF₃ | 6-F | O | NMe₂ | 4-OCF₃ | 6-F | O | NMe₂ |
| 4-CF₃ | 7-F | NMe | OH | 4-OCF₃ | 7-F | NMe | OH |
| 4-CF₃ | 7-F | NMe | OMe | 4-OCF₃ | 7-F | NMe | OMe |
| 4-CF₃ | 7-F | NMe | OCONHMe | 4-OCF₃ | 7-F | NMe | OCONHMe |
| 4-CF₃ | 7-F | NMe | CN | 4-OCF₃ | 7-F | NMe | CN |
| 4-CF₃ | 7-F | NMe | NMe₂ | 4-OCF₃ | 7-F | NMe | NMe₂ |
| 4-CF₃ | 7-Cl | NMe | OH | 4-OCF₃ | 7-Cl | NMe | OH |
| 4-CF₃ | 7-Cl | NMe | OMe | 4-OCF₃ | 7-Cl | NMe | OMe |
| 4-CF₃ | 7-Cl | NMe | OCONHMe | 4-OCF₃ | 7-Cl | NMe | OCONHMe |
| 4-CF₃ | 7-Cl | NMe | CN | 4-OCF₃ | 7-Cl | NMe | CN |
| 4-CF₃ | 7-Cl | NMe | NMe₂ | 4-OCF₃ | 7-Cl | NMe | NMe₂ |
| 4-CF₃ | 7-CF₃ | NMe | OH | 4-OCF₃ | 7-CF₃ | NMe | OH |
| 4-CF₃ | 7-CF₃ | NMe | OMe | 4-OCF₃ | 7-CF₃ | NMe | OMe |
| 4-CF₃ | 7-CF₃ | NMe | OCONHMe | 4-OCF₃ | 7-CF₃ | NMe | OCONHMe |
| 4-CF₃ | 7-CF₃ | NMe | CN | 4-OCF₃ | 7-CF₃ | NMe | CN |
| 4-CF₃ | 7-CF₃ | NMe | NMe₂ | 4-OCF₃ | 7-CF₃ | NMe | NMe₂ |
| 4-CF₃ | 7-OCF₃ | NMe | OH | 4-OCF₃ | 7-OCF₃ | NMe | OH |
| 4-CF₃ | 7-OCF₃ | NMe | OMe | 4-OCF₃ | 7-OCF₃ | NMe | OMe |
| 4-CF₃ | 7-OCF₃ | NMe | OCONHMe | 4-OCF₃ | 7-OCF₃ | NMe | OCONHMe |
| 4-CF₃ | 7-OCF₃ | NMe | CN | 4-OCF₃ | 7-OCF₃ | NMe | CN |
| 4-CF₃ | 7-OCF₃ | NMe | NMe₂ | 4-OCF₃ | 7-OCF₃ | NMe | NMe₂ |
| 4-CF₃ | 6-F | NMe | OH | 4-OCF₃ | 6-F | NMe | OH |

TABLE 13-continued

| R¹ | R² | V | X² | R¹ | R² | V | X² |
|---|---|---|---|---|---|---|---|
| 4-CF₃ | 6-F | NMe | OMe | 4-OCF₃ | 6-F | NMe | OMe |
| 4-CF₃ | 6-F | NMe | OCONHMe | 4-OCF₃ | 6-F | NMe | OCONHMe |
| 4-CF₃ | 6-F | NMe | CN | 4-OCF₃ | 6-F | NMe | CN |
| 4-CF₃ | 6-F | NMe | NMe₂ | 4-OCF₃ | 6-F | NMe | NMe₂ |
| 4-CF₃ | 7-F | NSO₂Me | OH | 4-OCF₃ | 7-F | NSO₂Me | OH |
| 4-CF₃ | 7-F | NSO₂Me | OMe | 4-OCF₃ | 7-F | NSO₂Me | OMe |
| 4-CF₃ | 7-F | NSO₂Me | OCONHMe | 4-OCF₃ | 7-F | NSO₂Me | OCONHMe |
| 4-CF₃ | 7-F | NSO₂Me | CN | 4-OCF₃ | 7-F | NSO₂Me | CN |
| 4-CF₃ | 7-F | NSO₂Me | NMe₂ | 4-OCF₃ | 7-F | NSO₂Me | NMe₂ |
| 4-CF₃ | 7-Cl | NSO₂Me | OH | 4-OCF₃ | 7-Cl | NSO₂Me | OH |
| 4-CF₃ | 7-Cl | NSO₂Me | OMe | 4-OCF₃ | 7-Cl | NSO₂Me | OMe |
| 4-CF₃ | 7-Cl | NSO₂Me | OCONHMe | 4-OCF₃ | 7-Cl | NSO₂Me | OCONHMe |
| 4-CF₃ | 7-Cl | NSO₂Me | CN | 4-OCF₃ | 7-Cl | NSO₂Me | CN |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | OH | 4-OCF₃ | 7-CF₃ | NSO₂Me | OH |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | OCONHMe | 4-OCF₃ | 7-CF₃ | NSO₂Me | OCONHMe |
| 4-CF₃ | 7-CF₃ | NSO₂Me | CN | 4-OCF₃ | 7-CF₃ | NSO₂Me | CN |
| 4-CF₃ | 7-CF₃ | NSO₂Me | NMe₂ | 4-OCF₃ | 7-CF₃ | NSO₂Me | NMe₂ |
| 4-CF₃ | 7-OCF₃ | NSO₂Me | OH | 4-OCF₃ | 7-OCF₃ | NSO₂Me | OH |
| 4-CF₃ | 7-OCF₃ | NSO₂Me | OMe | 4-OCF₃ | 7-OCF₃ | NSO₂Me | OMe |
| 4-CF₃ | 7-OCF₃ | NSO₂Me | OCONHMe | 4-OCF₃ | 7-OCF₃ | NSO₂Me | OCONHMe |
| 4-CF₃ | 7-OCF₃ | NSO₂Me | CN | 4-OCF₃ | 7-OCF₃ | NSO₂Me | CN |
| 4-CF₃ | 7-OCF₃ | NSO₂Me | NMe₂ | 4-OCF₃ | 7-OCF₃ | NSO₂Me | NMe₂ |
| 4-CF₃ | 6-F | NSO₂Me | OH | 4-OCF₃ | 6-F | NSO₂Me | OH |
| 4-CF₃ | 6-F | NSO₂Me | OMe | 4-OCF₃ | 6-F | NSO₂Me | OMe |
| 4-CF₃ | 6-F | NSO₂Me | OCONHMe | 4-OCF₃ | 6-F | NSO₂Me | OCONHMe |
| 4-CF₃ | 6-F | NSO₂Me | CN | 4-OCF₃ | 6-F | NSO₂Me | CN |
| 4-CF₃ | 6-F | NSO₂Me | NMe₂ | 4-OCF₃ | 6-F | NSO₂Me | NMe₂ |

TABLE 14

| R¹ | R² | V | X² | R¹ | R² | V | X² |
|---|---|---|---|---|---|---|---|
| 4-CF₃ | 7-F | CH₂ | OH | 4-OCF₃ | 7-F | CH₂ | OH |
| 4-CF₃ | 7-F | CH₂ | OMe | 4-OCF₃ | 7-F | CH₂ | OMe |
| 4-CF₃ | 7-F | CH₂ | OCONHMe | 4-OCF₃ | 7-F | CH₂ | OCONHMe |
| 4-CF₃ | 7-F | CH₂ | CN | 4-OCF₃ | 7-F | CH₂ | CN |
| 4-CF₃ | 7-F | CH₂ | NMe₂ | 4-OCF₃ | 7-F | CH₂ | NMe₂ |
| 4-CF₃ | 7-Cl | CH₂ | OH | 4-OCF₃ | 7-Cl | CH₂ | OH |
| 4-CF₃ | 7-Cl | CH₂ | OMe | 4-OCF₃ | 7-Cl | CH₂ | OMe |
| 4-CF₃ | 7-Cl | CH₂ | OCONHMe | 4-OCF₃ | 7-Cl | CH₂ | OCONHMe |
| 4-CF₃ | 7-Cl | CH₂ | CN | 4-OCF₃ | 7-Cl | CH₂ | CN |
| 4-CF₃ | 7-Cl | CH₂ | NMe₂ | 4-OCF₃ | 7-Cl | CH₂ | NMe₂ |
| 4-CF₃ | 7-CF₃ | CH₂ | OH | 4-OCF₃ | 7-CF₃ | CH₂ | OH |
| 4-CF₃ | 7-CF₃ | CH₂ | OMe | 4-OCF₃ | 7-CF₃ | CH₂ | OMe |
| 4-CF₃ | 7-CF₃ | CH₂ | OCONHMe | 4-OCF₃ | 7-CF₃ | CH₂ | OCONHMe |
| 4-CF₃ | 7-CF₃ | CH₂ | CN | 4-OCF₃ | 7-CF₃ | CH₂ | CN |
| 4-CF₃ | 7-CF₃ | CH₂ | NMe₂ | 4-OCF₃ | 7-CF₃ | CH₂ | NMe₂ |
| 4-CF₃ | 7-OCF₃ | CH₂ | OH | 4-OCF₃ | 7-OCF₃ | CH₂ | OH |
| 4-CF₃ | 7-OCF₃ | CH₂ | OMe | 4-OCF₃ | 7-OCF₃ | CH₂ | OMe |
| 4-CF₃ | 7-OCF₃ | CH₂ | OCONHMe | 4-OCF₃ | 7-OCF₃ | CH₂ | OCONHMe |
| 4-CF₃ | 7-OCF₃ | CH₂ | CN | 4-OCF₃ | 7-OCF₃ | CH₂ | CN |
| 4-CF₃ | 7-OCF₃ | CH₂ | NMe₂ | 4-OCF₃ | 7-OCF₃ | CH₂ | NMe₂ |
| 4-CF₃ | 6-F | CH₂ | OH | 4-OCF₃ | 6-F | CH₂ | OH |
| 4-CF₃ | 6-F | CH₂ | OMe | 4-OCF₃ | 6-F | CH₂ | OMe |
| 4-CF₃ | 6-F | CH₂ | OCONHMe | 4-OCF₃ | 6-F | CH₂ | OCONHMe |
| 4-CF₃ | 6-F | CH₂ | CN | 4-OCF₃ | 6-F | CH₂ | CN |
| 4-CF₃ | 6-F | CH₂ | NMe₂ | 4-OCF₃ | 6-F | CH₂ | NMe₂ |
| 4-CF₃ | 7-F | O | OH | 4-OCF₃ | 7-F | O | OH |
| 4-CF₃ | 7-F | O | OMe | 4-OCF₃ | 7-F | O | OMe |
| 4-CF₃ | 7-F | O | OCONHMe | 4-OCF₃ | 7-F | O | OCONHMe |
| 4-CF₃ | 7-F | O | CN | 4-OCF₃ | 7-F | O | CN |
| 4-CF₃ | 7-F | O | NMe₂ | 4-OCF₃ | 7-F | O | NMe₂ |
| 4-CF₃ | 7-Cl | O | OH | 4-OCF₃ | 7-Cl | O | OH |
| 4-CF₃ | 7-Cl | O | OMe | 4-OCF₃ | 7-Cl | O | OMe |
| 4-CF₃ | 7-Cl | O | OCONHMe | 4-OCF₃ | 7-Cl | O | OCONHMe |
| 4-CF₃ | 7-Cl | O | CN | 4-OCF₃ | 7-Cl | O | CN |
| 4-CF₃ | 7-Cl | O | NMe₂ | 4-OCF₃ | 7-Cl | O | NMe₂ |
| 4-CF₃ | 7-CF₃ | O | OH | 4-OCF₃ | 7-CF₃ | O | OH |
| 4-CF₃ | 7-CF₃ | O | OMe | 4-OCF₃ | 7-CF₃ | O | OMe |
| 4-CF₃ | 7-CF₃ | O | OCONHMe | 4-OCF₃ | 7-CF₃ | O | OCONHMe |
| 4-CF₃ | 7-CF₃ | O | CN | 4-OCF₃ | 7-CF₃ | O | CN |
| 4-CF₃ | 7-CF₃ | O | NMe₂ | 4-OCF₃ | 7-CF₃ | O | NMe₂ |
| 4-CF₃ | 7-OCF₃ | O | OH | 4-OCF₃ | 7-OCF₃ | O | OH |
| 4-CF₃ | 7-OCF₃ | O | OMe | 4-OCF₃ | 7-OCF₃ | O | OMe |
| 4-CF₃ | 7-OCF₃ | O | OCONHMe | 4-OCF₃ | 7-OCF₃ | O | OCONHMe |
| 4-CF₃ | 7-OCF₃ | O | CN | 4-OCF₃ | 7-OCF₃ | O | CN |
| 4-CF₃ | 7-OCF₃ | O | NMe₂ | 4-OCF₃ | 7-OCF₃ | O | NMe₂ |
| 4-CF₃ | 6-F | O | OH | 4-OCF₃ | 6-F | O | OH |

TABLE 14-continued

| R¹ | R² | V | X² | R¹ | R² | V | X² |
|---|---|---|---|---|---|---|---|
| 4-CF₃ | 6-F | O | OMe | 4-OCF₃ | 6-F | O | OMe |
| 4-CF₃ | 6-F | O | OCONHMe | 4-OCF₃ | 6-F | O | OCONHMe |
| 4-CF₃ | 6-F | O | CN | 4-OCF₃ | 6-F | O | CN |
| 4-CF₃ | 6-F | O | NMe₂ | 4-OCF₃ | 6-F | O | NMe₂ |
| 4-CF₃ | 7-F | NMe | OH | 4-OCF₃ | 7-F | NMe | OH |
| 4-CF₃ | 7-F | NMe | OMe | 4-OCF₃ | 7-F | NMe | OMe |
| 4-CF₃ | 7-F | NMe | OCONHMe | 4-OCF₃ | 7-F | NMe | OCONHMe |
| 4-CF₃ | 7-F | NMe | CN | 4-OCF₃ | 7-F | NMe | CN |
| 4-CF₃ | 7-F | NMe | NMe₂ | 4-OCF₃ | 7-F | NMe | NMe₂ |
| 4-CF₃ | 7-Cl | NMe | OH | 4-OCF₃ | 7-Cl | NMe | OH |
| 4-CF₃ | 7-Cl | NMe | OMe | 4-OCF₃ | 7-Cl | NMe | OMe |
| 4-CF₃ | 7-Cl | NMe | OCONHMe | 4-OCF₃ | 7-Cl | NMe | OCONHMe |
| 4-CF₃ | 7-Cl | NMe | CN | 4-OCF₃ | 7-Cl | NMe | CN |
| 4-CF₃ | 7-Cl | NMe | NMe₂ | 4-OCF₃ | 7-Cl | NMe | NMe₂ |
| 4-CF₃ | 7-CF₃ | NMe | OH | 4-OCF₃ | 7-CF₃ | NMe | OH |
| 4-CF₃ | 7-CF₃ | NMe | OMe | 4-OCF₃ | 7-CF₃ | NMe | OMe |
| 4-CF₃ | 7-CF₃ | NMe | OCONHMe | 4-OCF₃ | 7-CF₃ | NMe | OCONHMe |
| 4-CF₃ | 7-CF₃ | NMe | CN | 4-OCF₃ | 7-CF₃ | NMe | CN |
| 4-CF₃ | 7-CF₃ | NMe | NMe₂ | 4-OCF₃ | 7-CF₃ | NMe | NMe₂ |
| 4-CF₃ | 7-OCF₃ | NMe | OH | 4-OCF₃ | 7-OCF₃ | NMe | OH |
| 4-CF₃ | 7-OCF₃ | NMe | OMe | 4-OCF₃ | 7-OCF₃ | NMe | OMe |
| 4-CF₃ | 7-OCF₃ | NMe | OCONHMe | 4-OCF₃ | 7-OCF₃ | NMe | OCONHMe |
| 4-CF₃ | 7-OCF₃ | NMe | CN | 4-OCF₃ | 7-OCF₃ | NMe | CN |
| 4-CF₃ | 7-OCF₃ | NMe | NMe₂ | 4-OCF₃ | 7-OCF₃ | NMe | NMe₂ |
| 4-CF₃ | 6-F | NMe | OH | 4-OCF₃ | 6-F | NMe | OH |
| 4-CF₃ | 6-F | NMe | OMe | 4-OCF₃ | 6-F | NMe | OMe |
| 4-CF₃ | 6-F | NMe | OCONHMe | 4-OCF₃ | 6-F | NMe | OCONHMe |
| 4-CF₃ | 6-F | NMe | CN | 4-OCF₃ | 6-F | NMe | CN |
| 4-CF₃ | 6-F | NMe | NMe₂ | 4-OCF₃ | 6-F | NMe | NMe₂ |
| 4-CF₃ | 7-F | NSO₂Me | OH | 4-OCF₃ | 7-F | NSO₂Me | OH |
| 4-CF₃ | 7-F | NSO₂Me | OMe | 4-OCF₃ | 7-F | NSO₂Me | OMe |
| 4-CF₃ | 7-F | NSO₂Me | OCONHMe | 4-OCF₃ | 7-F | NSO₂Me | OCONHMe |
| 4-CF₃ | 7-F | NSO₂Me | CN | 4-OCF₃ | 7-F | NSO₂Me | CN |
| 4-CF₃ | 7-F | NSO₂Me | NMe₂ | 4-OCF₃ | 7-F | NSO₂Me | NMe₂ |
| 4-CF₃ | 7-Cl | NSO₂Me | OH | 4-OCF₃ | 7-Cl | NSO₂Me | OH |
| 4-CF₃ | 7-Cl | NSO₂Me | OMe | 4-OCF₃ | 7-Cl | NSO₂Me | OMe |
| 4-CF₃ | 7-Cl | NSO₂Me | OCONHMe | 4-OCF₃ | 7-Cl | NSO₂Me | OCONHMe |
| 4-CF₃ | 7-Cl | NSO₂Me | CN | 4-OCF₃ | 7-Cl | NSO₂Me | CN |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | OH | 4-OCF₃ | 7-CF₃ | NSO₂Me | OH |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | OCONHMe | 4-OCF₃ | 7-CF₃ | NSO₂Me | OCONHMe |
| 4-CF₃ | 7-CF₃ | NSO₂Me | CN | 4-OCF₃ | 7-CF₃ | NSO₂Me | CN |
| 4-CF₃ | 7-CF₃ | NSO₂Me | NMe₂ | 4-OCF₃ | 7-CF₃ | NSO₂Me | NMe₂ |
| 4-CF₃ | 7-OCF₃ | NSO₂Me | OH | 4-OCF₃ | 7-OCF₃ | NSO₂Me | OH |
| 4-CF₃ | 7-OCF₃ | NSO₂Me | OMe | 4-OCF₃ | 7-OCF₃ | NSO₂Me | OMe |
| 4-CF₃ | 7-OCF₃ | NSO₂Me | OCONHMe | 4-OCF₃ | 7-OCF₃ | NSO₂Me | OCONHMe |
| 4-CF₃ | 7-OCF₃ | NSO₂Me | CN | 4-OCF₃ | 7-OCF₃ | NSO₂Me | CN |
| 4-CF₃ | 7-OCF₃ | NSO₂Me | NMe₂ | 4-OCF₃ | 7-OCF₃ | NSO₂Me | NMe₂ |
| 4-CF₃ | 6-F | NSO₂Me | OH | 4-OCF₃ | 6-F | NSO₂Me | OH |
| 4-CF₃ | 6-F | NSO₂Me | OMe | 4-OCF₃ | 6-F | NSO₂Me | OMe |
| 4-CF₃ | 6-F | NSO₂Me | OCONHMe | 4-OCF₃ | 6-F | NSO₂Me | OCONHMe |
| 4-CF₃ | 6-F | NSO₂Me | CN | 4-OCF₃ | 6-F | NSO₂Me | CN |
| 4-CF₃ | 6-F | NSO₂Me | NMe₂ | 4-OCF₃ | 6-F | NSO₂Me | NMe₂ |

TABLE 15

| R¹ | R² | V | X² | R¹ | R² | V | X² |
|---|---|---|---|---|---|---|---|
| 4-CF₃ | 7-F | CH₂ | OH | 4-OCF₃ | 7-F | CH₂ | OH |
| 4-CF₃ | 7-F | CH₂ | OMe | 4-OCF₃ | 7-F | CH₂ | OMe |
| 4-CF₃ | 7-F | CH₂ | OCONHMe | 4-OCF₃ | 7-F | CH₂ | OCONHMe |
| 4-CF₃ | 7-F | CH₂ | CN | 4-OCF₃ | 7-F | CH₂ | CN |
| 4-CF₃ | 7-F | CH₂ | NMe₂ | 4-OCF₃ | 7-F | CH₂ | NMe₂ |
| 4-CF₃ | 7-Cl | CH₂ | OH | 4-OCF₃ | 7-Cl | CH₂ | OH |
| 4-CF₃ | 7-Cl | CH₂ | OMe | 4-OCF₃ | 7-Cl | CH₂ | OMe |
| 4-CF₃ | 7-Cl | CH₂ | OCONHMe | 4-OCF₃ | 7-Cl | CH₂ | OCONHMe |
| 4-CF₃ | 7-Cl | CH₂ | CN | 4-OCF₃ | 7-Cl | CH₂ | CN |
| 4-CF₃ | 7-Cl | CH₂ | NMe₂ | 4-OCF₃ | 7-Cl | CH₂ | NMe₂ |
| 4-CF₃ | 7-CF₃ | CH₂ | OH | 4-OCF₃ | 7-CF₃ | CH₂ | OH |
| 4-CF₃ | 7-CF₃ | CH₂ | OMe | 4-OCF₃ | 7-CF₃ | CH₂ | OMe |
| 4-CF₃ | 7-CF₃ | CH₂ | OCONHMe | 4-OCF₃ | 7-CF₃ | CH₂ | OCONHMe |
| 4-CF₃ | 7-CF₃ | CH₂ | CN | 4-OCF₃ | 7-CF₃ | CH₂ | CN |
| 4-CF₃ | 7-CF₃ | CH₂ | NMe₂ | 4-OCF₃ | 7-CF₃ | CH₂ | NMe₂ |
| 4-CF₃ | 7-OCF₃ | CH₂ | OH | 4-OCF₃ | 7-OCF₃ | CH₂ | OH |
| 4-CF₃ | 7-OCF₃ | CH₂ | OMe | 4-OCF₃ | 7-OCF₃ | CH₂ | OMe |
| 4-CF₃ | 7-OCF₃ | CH₂ | OCONHMe | 4-OCF₃ | 7-OCF₃ | CH₂ | OCONHMe |
| 4-CF₃ | 7-OCF₃ | CH₂ | CN | 4-OCF₃ | 7-OCF₃ | CH₂ | CN |
| 4-CF₃ | 7-OCF₃ | CH₂ | NMe₂ | 4-OCF₃ | 7-OCF₃ | CH₂ | NMe₂ |
| 4-CF₃ | 6-F | CH₂ | OH | 4-OCF₃ | 6-F | CH₂ | OH |

TABLE 15-continued

| R¹ | R² | V | X² | R¹ | R² | V | X² |
|---|---|---|---|---|---|---|---|
| 4-CF₃ | 6-F | CH₂ | OMe | 4-OCF₃ | 6-F | CH₂ | OMe |
| 4-CF₃ | 6-F | CH₂ | OCONHMe | 4-OCF₃ | 6-F | CH₂ | OCONHMe |
| 4-CF₃ | 6-F | CH₂ | CN | 4-OCF₃ | 6-F | CH₂ | CN |
| 4-CF₃ | 6-F | CH₂ | NMe₂ | 4-OCF₃ | 6-F | CH₂ | NMe₂ |
| 4-CF₃ | 7-F | O | OH | 4-OCF₃ | 7-F | O | OH |
| 4-CF₃ | 7-F | O | OMe | 4-OCF₃ | 7-F | O | OMe |
| 4-CF₃ | 7-F | O | OCONHMe | 4-OCF₃ | 7-F | O | OCONHMe |
| 4-CF₃ | 7-F | O | CN | 4-OCF₃ | 7-F | O | CN |
| 4-CF₃ | 7-F | O | NMe₂ | 4-OCF₃ | 7-F | O | NMe₂ |
| 4-CF₃ | 7-Cl | O | OH | 4-OCF₃ | 7-Cl | O | OH |
| 4-CF₃ | 7-Cl | O | OMe | 4-OCF₃ | 7-Cl | O | OMe |
| 4-CF₃ | 7-Cl | O | OCONHMe | 4-OCF₃ | 7-Cl | O | OCONHMe |
| 4-CF₃ | 7-Cl | O | CN | 4-OCF₃ | 7-Cl | O | CN |
| 4-CF₃ | 7-Cl | O | NMe₂ | 4-OCF₃ | 7-Cl | O | NMe₂ |
| 4-CF₃ | 7-CF₃ | O | OH | 4-OCF₃ | 7-CF₃ | O | OH |
| 4-CF₃ | 7-CF₃ | O | OMe | 4-OCF₃ | 7-CF₃ | O | OMe |
| 4-CF₃ | 7-CF₃ | O | OCONHMe | 4-OCF₃ | 7-CF₃ | O | OCONHMe |
| 4-CF₃ | 7-CF₃ | O | CN | 4-OCF₃ | 7-CF₃ | O | CN |
| 4-CF₃ | 7-CF₃ | O | NMe₂ | 4-OCF₃ | 7-CF₃ | O | NMe₂ |
| 4-CF₃ | 7-OCF₃ | O | OH | 4-OCF₃ | 7-OCF₃ | O | OH |
| 4-CF₃ | 7-OCF₃ | O | OMe | 4-OCF₃ | 7-OCF₃ | O | OMe |
| 4-CF₃ | 7-OCF₃ | O | OCONHMe | 4-OCF₃ | 7-OCF₃ | O | OCONHMe |
| 4-CF₃ | 7-OCF₃ | O | CN | 4-OCF₃ | 7-OCF₃ | O | CN |
| 4-CF₃ | 7-OCF₃ | O | NMe₂ | 4-OCF₃ | 7-OCF₃ | O | NMe₂ |
| 4-CF₃ | 6-F | O | OH | 4-OCF₃ | 6-F | O | OH |
| 4-CF₃ | 6-F | O | OMe | 4-OCF₃ | 6-F | O | OMe |
| 4-CF₃ | 6-F | O | OCONHMe | 4-OCF₃ | 6-F | O | OCONHMe |
| 4-CF₃ | 6-F | O | CN | 4-OCF₃ | 6-F | O | CN |
| 4-CF₃ | 6-F | O | NMe₂ | 4-OCF₃ | 6-F | O | NMe₂ |
| 4-CF₃ | 7-F | NMe | OH | 4-OCF₃ | 7-F | NMe | OH |
| 4-CF₃ | 7-F | NMe | OMe | 4-OCF₃ | 7-F | NMe | OMe |
| 4-CF₃ | 7-F | NMe | OCONHMe | 4-OCF₃ | 7-F | NMe | OCONHMe |
| 4-CF₃ | 7-F | NMe | CN | 4-OCF₃ | 7-F | NMe | CN |
| 4-CF₃ | 7-F | NMe | NMe₂ | 4-OCF₃ | 7-F | NMe | NMe₂ |
| 4-CF₃ | 7-Cl | NMe | OH | 4-OCF₃ | 7-Cl | NMe | OH |
| 4-CF₃ | 7-Cl | NMe | OMe | 4-OCF₃ | 7-Cl | NMe | OMe |
| 4-CF₃ | 7-Cl | NMe | OCONHMe | 4-OCF₃ | 7-Cl | NMe | OCONHMe |
| 4-CF₃ | 7-Cl | NMe | CN | 4-OCF₃ | 7-Cl | NMe | CN |
| 4-CF₃ | 7-Cl | NMe | NMe₂ | 4-OCF₃ | 7-Cl | NMe | NMe₂ |
| 4-CF₃ | 7-CF₃ | NMe | OH | 4-OCF₃ | 7-CF₃ | NMe | OH |
| 4-CF₃ | 7-CF₃ | NMe | OMe | 4-OCF₃ | 7-CF₃ | NMe | OMe |
| 4-CF₃ | 7-CF₃ | NMe | OCONHMe | 4-OCF₃ | 7-CF₃ | NMe | OCONHMe |
| 4-CF₃ | 7-CF₃ | NMe | CN | 4-OCF₃ | 7-CF₃ | NMe | CN |
| 4-CF₃ | 7-CF₃ | NMe | NMe₂ | 4-OCF₃ | 7-CF₃ | NMe | NMe₂ |
| 4-CF₃ | 7-OCF₃ | NMe | OH | 4-OCF₃ | 7-OCF₃ | NMe | OH |
| 4-CF₃ | 7-OCF₃ | NMe | OMe | 4-OCF₃ | 7-OCF₃ | NMe | OMe |
| 4-CF₃ | 7-OCF₃ | NMe | OCONHMe | 4-OCF₃ | 7-OCF₃ | NMe | OCONHMe |
| 4-CF₃ | 7-OCF₃ | NMe | CN | 4-OCF₃ | 7-OCF₃ | NMe | CN |
| 4-CF₃ | 7-OCF₃ | NMe | NMe₂ | 4-OCF₃ | 7-OCF₃ | NMe | NMe₂ |
| 4-CF₃ | 6-F | NMe | OH | 4-OCF₃ | 6-F | NMe | OH |
| 4-CF₃ | 6-F | NMe | OMe | 4-OCF₃ | 6-F | NMe | OMe |
| 4-CF₃ | 6-F | NMe | OCONHMe | 4-OCF₃ | 6-F | NMe | OCONHMe |
| 4-CF₃ | 6-F | NMe | CN | 4-OCF₃ | 6-F | NMe | CN |
| 4-CF₃ | 6-F | NMe | NMe₂ | 4-OCF₃ | 6-F | NMe | NMe₂ |
| 4-CF₃ | 7-F | NSO₂Me | OH | 4-OCF₃ | 7-F | NSO₂Me | OH |
| 4-CF₃ | 7-F | NSO₂Me | OMe | 4-OCF₃ | 7-F | NSO₂Me | OMe |
| 4-CF₃ | 7-F | NSO₂Me | OCONHMe | 4-OCF₃ | 7-F | NSO₂Me | OCONHMe |
| 4-CF₃ | 7-F | NSO₂Me | CN | 4-OCF₃ | 7-F | NSO₂Me | CN |
| 4-CF₃ | 7-F | NSO₂Me | NMe₂ | 4-OCF₃ | 7-F | NSO₂Me | NMe₂ |
| 4-CF₃ | 7-Cl | NSO₂Me | OH | 4-OCF₃ | 7-Cl | NSO₂Me | OH |
| 4-CF₃ | 7-Cl | NSO₂Me | OMe | 4-OCF₃ | 7-Cl | NSO₂Me | OMe |
| 4-CF₃ | 7-Cl | NSO₂Me | OCONHMe | 4-OCF₃ | 7-Cl | NSO₂Me | OCONHMe |
| 4-CF₃ | 7-Cl | NSO₂Me | CN | 4-OCF₃ | 7-Cl | NSO₂Me | CN |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | OH | 4-OCF₃ | 7-CF₃ | NSO₂Me | OH |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | OCONHMe | 4-OCF₃ | 7-CF₃ | NSO₂Me | OCONHMe |
| 4-CF₃ | 7-CF₃ | NSO₂Me | CN | 4-OCF₃ | 7-CF₃ | NSO₂Me | CN |
| 4-CF₃ | 7-CF₃ | NSO₂Me | NMe₂ | 4-OCF₃ | 7-CF₃ | NSO₂Me | NMe₂ |
| 4-CF₃ | 7-OCF₃ | NSO₂Me | OH | 4-OCF₃ | 7-OCF₃ | NSO₂Me | OH |
| 4-CF₃ | 7-OCF₃ | NSO₂Me | OMe | 4-OCF₃ | 7-OCF₃ | NSO₂Me | OMe |
| 4-CF₃ | 7-OCF₃ | NSO₂Me | OCONHMe | 4-OCF₃ | 7-OCF₃ | NSO₂Me | OCONHMe |
| 4-CF₃ | 7-OCF₃ | NSO₂Me | CN | 4-OCF₃ | 7-OCF₃ | NSO₂Me | CN |
| 4-CF₃ | 7-OCF₃ | NSO₂Me | NMe₂ | 4-OCF₃ | 7-OCF₃ | NSO₂Me | NMe₂ |
| 4-CF₃ | 6-F | NSO₂Me | OH | 4-OCF₃ | 6-F | NSO₂Me | OH |
| 4-CF₃ | 6-F | NSO₂Me | OMe | 4-OCF₃ | 6-F | NSO₂Me | OMe |
| 4-CF₃ | 6-F | NSO₂Me | OCONHMe | 4-OCF₃ | 6-F | NSO₂Me | OCONHMe |
| 4-CF₃ | 6-F | NSO₂Me | CN | 4-OCF₃ | 6-F | NSO₂Me | CN |
| 4-CF₃ | 6-F | NSO₂Me | NMe₂ | 4-OCF₃ | 6-F | NSO₂Me | NMe₂ |

TABLE 16

| R¹ | R² | V | X² | R¹ | R² | V | X² |
|---|---|---|---|---|---|---|---|
| 4-CF₃ | 7-F | CH₂ | OH | 4-OCF₃ | 7-F | CH₂ | OH |
| 4-CF₃ | 7-F | CH₂ | OMe | 4-OCF₃ | 7-F | CH₂ | OMe |
| 4-CF₃ | 7-F | CH₂ | OCONHMe | 4-OCF₃ | 7-F | CH₂ | OCONHMe |
| 4-CF₃ | 7-F | CH₂ | CN | 4-OCF₃ | 7-F | CH₂ | CN |
| 4-CF₃ | 7-F | CH₂ | NMe₂ | 4-OCF₃ | 7-F | CH₂ | NMe₂ |
| 4-CF₃ | 7-Cl | CH₂ | OH | 4-OCF₃ | 7-Cl | CH₂ | OH |
| 4-CF₃ | 7-Cl | CH₂ | OMe | 4-OCF₃ | 7-Cl | CH₂ | OMe |
| 4-CF₃ | 7-Cl | CH₂ | OCONHMe | 4-OCF₃ | 7-Cl | CH₂ | OCONHMe |
| 4-CF₃ | 7-Cl | CH₂ | CN | 4-OCF₃ | 7-Cl | CH₂ | CN |
| 4-CF₃ | 7-Cl | CH₂ | NMe₂ | 4-OCF₃ | 7-Cl | CH₂ | NMe₂ |
| 4-CF₃ | 7-CF₃ | CH₂ | OH | 4-OCF₃ | 7-CF₃ | CH₂ | OH |
| 4-CF₃ | 7-CF₃ | CH₂ | OMe | 4-OCF₃ | 7-CF₃ | CH₂ | OMe |
| 4-CF₃ | 7-CF₃ | CH₂ | OCONHMe | 4-OCF₃ | 7-CF₃ | CH₂ | OCONHMe |
| 4-CF₃ | 7-CF₃ | CH₂ | CN | 4-OCF₃ | 7-CF₃ | CH₂ | CN |
| 4-CF₃ | 7-CF₃ | CH₂ | NMe₂ | 4-OCF₃ | 7-CF₃ | CH₂ | NMe₂ |
| 4-CF₃ | 7-OCF₃ | CH₂ | OH | 4-OCF₃ | 7-OCF₃ | CH₂ | OH |
| 4-CF₃ | 7-OCF₃ | CH₂ | OMe | 4-OCF₃ | 7-OCF₃ | CH₂ | OMe |
| 4-CF₃ | 7-OCF₃ | CH₂ | OCONHMe | 4-OCF₃ | 7-OCF₃ | CH₂ | OCONHMe |
| 4-CF₃ | 7-OCF₃ | CH₂ | CN | 4-OCF₃ | 7-OCF₃ | CH₂ | CN |
| 4-CF₃ | 7-OCF₃ | CH₂ | NMe₂ | 4-OCF₃ | 7-OCF₃ | CH₂ | NMe₂ |
| 4-CF₃ | 6-F | CH₂ | OH | 4-OCF₃ | 6-F | CH₂ | OH |
| 4-CF₃ | 6-F | CH₂ | OMe | 4-OCF₃ | 6-F | CH₂ | OMe |
| 4-CF₃ | 6-F | CH₂ | OCONHMe | 4-OCF₃ | 6-F | CH₂ | OCONHMe |
| 4-CF₃ | 6-F | CH₂ | CN | 4-OCF₃ | 6-F | CH₂ | CN |
| 4-CF₃ | 6-F | CH₂ | NMe₂ | 4-OCF₃ | 6-F | CH₂ | NMe₂ |
| 4-CF₃ | 7-F | O | OH | 4-OCF₃ | 7-F | O | OH |
| 4-CF₃ | 7-F | O | OMe | 4-OCF₃ | 7-F | O | OMe |
| 4-CF₃ | 7-F | O | OCONHMe | 4-OCF₃ | 7-F | O | OCONHMe |
| 4-CF₃ | 7-F | O | CN | 4-OCF₃ | 7-F | O | CN |
| 4-CF₃ | 7-F | O | NMe₂ | 4-OCF₃ | 7-F | O | NMe₂ |
| 4-CF₃ | 7-Cl | O | OH | 4-OCF₃ | 7-Cl | O | OH |
| 4-CF₃ | 7-Cl | O | OMe | 4-OCF₃ | 7-Cl | O | OMe |
| 4-CF₃ | 7-Cl | O | OCONHMe | 4-OCF₃ | 7-Cl | O | OCONHMe |
| 4-CF₃ | 7-Cl | O | CN | 4-OCF₃ | 7-Cl | O | CN |
| 4-CF₃ | 7-Cl | O | NMe₂ | 4-OCF₃ | 7-Cl | O | NMe₂ |
| 4-CF₃ | 7-CF₃ | O | OH | 4-OCF₃ | 7-CF₃ | O | OH |
| 4-CF₃ | 7-CF₃ | O | OMe | 4-OCF₃ | 7-CF₃ | O | OMe |
| 4-CF₃ | 7-CF₃ | O | OCONHMe | 4-OCF₃ | 7-CF₃ | O | OCONHMe |
| 4-CF₃ | 7-CF₃ | O | CN | 4-OCF₃ | 7-CF₃ | O | CN |
| 4-CF₃ | 7-CF₃ | O | NMe₂ | 4-OCF₃ | 7-CF₃ | O | NMe₂ |
| 4-CF₃ | 7-OCF₃ | O | OH | 4-OCF₃ | 7-OCF₃ | O | OH |
| 4-CF₃ | 7-OCF₃ | O | OMe | 4-OCF₃ | 7-OCF₃ | O | OMe |
| 4-CF₃ | 7-OCF₃ | O | OCONHMe | 4-OCF₃ | 7-OCF₃ | O | OCONHMe |
| 4-CF₃ | 7-OCF₃ | O | CN | 4-OCF₃ | 7-OCF₃ | O | CN |
| 4-CF₃ | 7-OCF₃ | O | NMe₂ | 4-OCF₃ | 7-OCF₃ | O | NMe₂ |
| 4-CF₃ | 6-F | O | OH | 4-OCF₃ | 6-F | O | OH |
| 4-CF₃ | 6-F | O | OMe | 4-OCF₃ | 6-F | O | OMe |
| 4-CF₃ | 6-F | O | OCONHMe | 4-OCF₃ | 6-F | O | OCONHMe |
| 4-CF₃ | 6-F | O | CN | 4-OCF₃ | 6-F | O | CN |
| 4-CF₃ | 6-F | O | NMe₂ | 4-OCF₃ | 6-F | O | NMe₂ |
| 4-CF₃ | 7-F | NMe | OH | 4-OCF₃ | 7-F | NMe | OH |
| 4-CF₃ | 7-F | NMe | OMe | 4-OCF₃ | 7-F | NMe | OMe |
| 4-CF₃ | 7-F | NMe | OCONHMe | 4-OCF₃ | 7-F | NMe | OCONHMe |
| 4-CF₃ | 7-F | NMe | CN | 4-OCF₃ | 7-F | NMe | CN |
| 4-CF₃ | 7-F | NMe | NMe₂ | 4-OCF₃ | 7-F | NMe | NMe₂ |
| 4-CF₃ | 7-Cl | NMe | OH | 4-OCF₃ | 7-Cl | NMe | OH |
| 4-CF₃ | 7-Cl | NMe | OMe | 4-OCF₃ | 7-Cl | NMe | OMe |
| 4-CF₃ | 7-Cl | NMe | OCONHMe | 4-OCF₃ | 7-Cl | NMe | OCONHMe |
| 4-CF₃ | 7-Cl | NMe | CN | 4-OCF₃ | 7-Cl | NMe | CN |
| 4-CF₃ | 7-Cl | NMe | NMe₂ | 4-OCF₃ | 7-Cl | NMe | NMe₂ |
| 4-CF₃ | 7-CF₃ | NMe | OH | 4-OCF₃ | 7-CF₃ | NMe | OH |
| 4-CF₃ | 7-CF₃ | NMe | OMe | 4-OCF₃ | 7-CF₃ | NMe | OMe |
| 4-CF₃ | 7-CF₃ | NMe | OCONHMe | 4-OCF₃ | 7-CF₃ | NMe | OCONHMe |
| 4-CF₃ | 7-CF₃ | NMe | CN | 4-OCF₃ | 7-CF₃ | NMe | CN |
| 4-CF₃ | 7-CF₃ | NMe | NMe₂ | 4-OCF₃ | 7-CF₃ | NMe | NMe₂ |
| 4-CF₃ | 7-OCF₃ | NMe | OH | 4-OCF₃ | 7-OCF₃ | NMe | OH |
| 4-CF₃ | 7-OCF₃ | NMe | OMe | 4-OCF₃ | 7-OCF₃ | NMe | OMe |
| 4-CF₃ | 7-OCF₃ | NMe | OCONHMe | 4-OCF₃ | 7-OCF₃ | NMe | OCONHMe |
| 4-CF₃ | 7-OCF₃ | NMe | CN | 4-OCF₃ | 7-OCF₃ | NMe | CN |
| 4-CF₃ | 7-OCF₃ | NMe | NMe₂ | 4-OCF₃ | 7-OCF₃ | NMe | NMe₂ |
| 4-CF₃ | 6-F | NMe | OH | 4-OCF₃ | 6-F | NMe | OH |
| 4-CF₃ | 6-F | NMe | OMe | 4-OCF₃ | 6-F | NMe | OMe |
| 4-CF₃ | 6-F | NMe | OCONHMe | 4-OCF₃ | 6-F | NMe | OCONHMe |
| 4-CF₃ | 6-F | NMe | CN | 4-OCF₃ | 6-F | NMe | CN |
| 4-CF₃ | 6-F | NMe | NMe₂ | 4-OCF₃ | 6-F | NMe | NMe₂ |
| 4-CF₃ | 7-F | NSO₂Me | OH | 4-OCF₃ | 7-F | NSO₂Me | OH |
| 4-CF₃ | 7-F | NSO₂Me | OMe | 4-OCF₃ | 7-F | NSO₂Me | OMe |
| 4-CF₃ | 7-F | NSO₂Me | OCONHMe | 4-OCF₃ | 7-F | NSO₂Me | OCONHMe |
| 4-CF₃ | 7-F | NSO₂Me | CN | 4-OCF₃ | 7-F | NSO₂Me | CN |
| 4-CF₃ | 7-F | NSO₂Me | NMe₂ | 4-OCF₃ | 7-F | NSO₂Me | NMe₂ |
| 4-CF₃ | 7-Cl | NSO₂Me | OH | 4-OCF₃ | 7-Cl | NSO₂Me | OH |

TABLE 16-continued

| R¹ | R² | V | X² | R¹ | R² | V | X² |
|---|---|---|---|---|---|---|---|
| 4-CF₃ | 7-Cl | NSO₂Me | OMe | 4-OCF₃ | 7-Cl | NSO₂Me | OMe |
| 4-CF₃ | 7-Cl | NSO₂Me | OCONHMe | 4-OCF₃ | 7-Cl | NSO₂Me | OCONHMe |
| 4-CF₃ | 7-Cl | NSO₂Me | CN | 4-OCF₃ | 7-Cl | NSO₂Me | CN |
| 4-CF₃ | 7-Cl | NSO₂Me | NMe₂ | 4-OCF₃ | 7-Cl | NSO₂Me | NMe₂ |
| 4-CF₃ | 7-CF₃ | NSO₂Me | OH | 4-OCF₃ | 7-CF₃ | NSO₂Me | OH |
| 4-CF₃ | 7-CF₃ | NSO₂Me | OMe | 4-OCF₃ | 7-CF₃ | NSO₂Me | OMe |
| 4-CF₃ | 7-CF₃ | NSO₂Me | OCONHMe | 4-OCF₃ | 7-CF₃ | NSO₂Me | OCONHMe |
| 4-CF₃ | 7-CF₃ | NSO₂Me | CN | 4-OCF₃ | 7-CF₃ | NSO₂Me | CN |
| 4-CF₃ | 7-CF₃ | NSO₂Me | NMe₂ | 4-OCF₃ | 7-CF₃ | NSO₂Me | NMe₂ |
| 4-CF₃ | 7-OCF₃ | NSO₂Me | OH | 4-OCF₃ | 7-OCF₃ | NSO₂Me | OH |
| 4-CF₃ | 7-OCF₃ | NSO₂Me | OMe | 4-OCF₃ | 7-OCF₃ | NSO₂Me | OMe |
| 4-CF₃ | 7-OCF₃ | NSO₂Me | OCONHMe | 4-OCF₃ | 7-OCF₃ | NSO₂Me | OCONHMe |
| 4-CF₃ | 7-OCF₃ | NSO₂Me | CN | 4-OCF₃ | 7-OCF₃ | NSO₂Me | CN |
| 4-CF₃ | 7-OCF₃ | NSO₂Me | NMe₂ | 4-OCF₃ | 7-OCF₃ | NSO₂Me | NMe₂ |
| 4-CF₃ | 6-F | NSO₂Me | OH | 4-OCF₃ | 6-F | NSO₂Me | OH |
| 4-CF₃ | 6-F | NSO₂Me | OMe | 4-OCF₃ | 6-F | NSO₂Me | OMe |
| 4-CF₃ | 6-F | NSO₂Me | OCONHMe | 4-OCF₃ | 6-F | NSO₂Me | OCONHMe |
| 4-CF₃ | 6-F | NSO₂Me | CN | 4-OCF₃ | 6-F | NSO₂Me | CN |
| 4-CF₃ | 6-F | NSO₂Me | NMe₂ | 4-OCF₃ | 6-F | NSO₂Me | NMe₂ |

TABLE 17

| R¹ | R² | R³ | X² | R¹ | R² | R³ | X² |
|---|---|---|---|---|---|---|---|
| 4-CF₃ | Cl | iPr | OCH₂Ph | 4-CF₃ | CF₃ | CO₂Me | OCH₂Ph |
| 4-CF₃ | Cl | iPr | OCH₂CHCH₂ | 4-CF₃ | CF₃ | CO₂Me | OCH₂CHCH₂ |
| 4-CF₃ | Cl | iPr | OCH₂CCH | 4-CF₃ | CF₃ | CO₂Me | OCH₂CCH |
| 4-CF₃ | Cl | iPr | OCONMe₂ | 4-CF₃ | CF₃ | CO₂Me | OCONMe₂ |
| 4-CF₃ | Cl | iPr | OCONH-4-Cl-Ph | 4-CF₃ | CF₃ | CO₂Me | OCONH-4-Cl-Ph |
| 4-CF₃ | Cl | iPr | OCONH-4-CF₃-Ph | 4-CF₃ | CF₃ | CO₂Me | OCONH-4-CF₃-Ph |
| 4-CF₃ | Cl | iPr | OCOMe | 4-CF₃ | CF₃ | CO₂Me | OCOMe |
| 4-CF₃ | Cl | iPr | OCO₂Me | 4-CF₃ | CF₃ | CO₂Me | OCO₂Me |
| 4-CF₃ | Cl | iPr | NHMe | 4-CF₃ | CF₃ | CO₂Me | NHMe |
| 4-CF₃ | Cl | iPr | NHCO₂Me | 4-CF₃ | CF₃ | CO₂Me | NHCO₂Me |
| 4-CF₃ | Cl | iPr | NHCH₂CF₃ | 4-CF₃ | CF₃ | CO₂Me | NHCH₂CF₃ |
| 4-CF₃ | Cl | iPr | NHPh | 4-CF₃ | CF₃ | CO₂Me | NHPh |
| 4-CF₃ | Cl | iPr | NHPy | 4-CF₃ | CF₃ | CO₂Me | NHPy |
| 4-CF₃ | Cl | iPr | NMePh | 4-CF₃ | CF₃ | CO₂Me | NMePh |
| 4-CF₃ | Cl | iPr | OSO₂Me | 4-CF₃ | CF₃ | CO₂Me | OSO₂Me |
| 4-CF₃ | Cl | iPr | OSO₂Ph | 4-CF₃ | CF₃ | CO₂Me | OSO₂Ph |
| 4-CF₃ | Cl | iPr | OCSNMe₂ | 4-CF₃ | CF₃ | CO₂Me | OCSNMe₂ |
| 4-OCF₃ | Cl | iPr | OCH₂Ph | 4-OCF₃ | CF₃ | CO₂Me | OCH₂Ph |
| 4-OCF₃ | Cl | iPr | OCH₂CHCH₂ | 4-OCF₃ | CF₃ | CO₂Me | OCH₂CHCH₂ |
| 4-OCF₃ | Cl | iPr | OCH₂CCH | 4-OCF₃ | CF₃ | CO₂Me | OCH₂CCH |
| 4-OCF₃ | Cl | iPr | OCONMe₂ | 4-OCF₃ | CF₃ | CO₂Me | OCONMe₂ |
| 4-OCF₃ | Cl | iPr | OCONH-4-Cl-Ph | 4-OCF₃ | CF₃ | CO₂Me | OCONH-4-Cl-Ph |
| 4-OCF₃ | Cl | iPr | OCONH-4-CF₃-Ph | 4-OCF₃ | CF₃ | CO₂Me | OCONH-4-CF₃-Ph |
| 4-OCF₃ | Cl | iPr | OCOMe | 4-OCF₃ | CF₃ | CO₂Me | OCOMe |
| 4-OCF₃ | Cl | iPr | OCO₂Me | 4-OCF₃ | CF₃ | CO₂Me | OCO₂Me |
| 4-OCF₃ | Cl | iPr | NHMe | 4-OCF₃ | CF₃ | CO₂Me | NHMe |
| 4-OCF₃ | Cl | iPr | NHCO₂Me | 4-OCF₃ | CF₃ | CO₂Me | NHCO₂Me |
| 4-OCF₃ | Cl | iPr | NHCH₂CF₃ | 4-OCF₃ | CF₃ | CO₂Me | NHCH₂CF₃ |
| 4-OCF₃ | Cl | iPr | NHPh | 4-OCF₃ | CF₃ | CO₂Me | NHPh |
| 4-OCF₃ | Cl | iPr | NHPy | 4-OCF₃ | CF₃ | CO₂Me | NHPy |
| 4-OCF₃ | Cl | iPr | NMePh | 4-OCF₃ | CF₃ | CO₂Me | NMePh |
| 4-OCF₃ | Cl | iPr | OSO₂Me | 4-OCF₃ | CF₃ | CO₂Me | OSO₂Me |
| 4-OCF₃ | Cl | iPr | OSO₂Ph | 4-OCF₃ | CF₃ | CO₂Me | OSO₂Ph |
| 4-OCF₃ | Cl | iPr | OCSNMe₂ | 4-OCF₃ | CF₃ | CO₂Me | OCSNMe₂ |

TABLE 18

| R¹ | R² | R³ | X² | R¹ | R² | R³ | X² | R¹ | R² | R³ | X² | R¹ | R² | R³ | X² |
|---|---|---|---|---|---|---|---|---|---|---|---|---|---|---|---|
| 4-CF₃ | 7-F | CO₂Me | OH | 4-OCF₃ | 7-F | CO₂Me | OH | 4-CF₃ | 7-F | 4-F-Ph | OH | 4-OCF₃ | 7-F | 4-F-Ph | OH |
| 4-CF₃ | 7-F | CO₂Me | OMe | 4-OCF₃ | 7-F | CO₂Me | OMe | 4-CF₃ | 7-F | 4-F-Ph | OMe | 4-OCF₃ | 7-F | 4-F-Ph | OMe |
| 4-CF₃ | 7-F | CO₂Me | CN | 4-OCF₃ | 7-F | CO₂Me | CN | 4-CF₃ | 7-F | 4-F-Ph | CN | 4-OCF₃ | 7-F | 4-F-Ph | CN |
| 4-CF₃ | 7-F | CO₂Me | NMe₂ | 4-OCF₃ | 7-F | CO₂Me | NMe₂ | 4-CF₃ | 7-F | 4-F-Ph | NMe₂ | 4-OCF₃ | 7-F | 4-F-Ph | NMe₂ |
| 4-CF₃ | 7-Cl | CO₂Me | OH | 4-OCF₃ | 7-Cl | CO₂Me | OH | 4-CF₃ | 7-Cl | 4-F-Ph | OH | 4-OCF₃ | 7-Cl | 4-F-Ph | OH |
| 4-CF₃ | 7-Cl | CO₂Me | OMe | 4-OCF₃ | 7-Cl | CO₂Me | OMe | 4-CF₃ | 7-Cl | 4-F-Ph | OMe | 4-OCF₃ | 7-Cl | 4-F-Ph | OMe |
| 4-CF₃ | 7-Cl | CO₂Me | CN | 4-OCF₃ | 7-Cl | CO₂Me | CN | 4-CF₃ | 7-Cl | 4-F-Ph | CN | 4-OCF₃ | 7-Cl | 4-F-Ph | CN |
| 4-CF₃ | 7-Cl | CO₂Me | NMe₂ | 4-OCF₃ | 7-Cl | CO₂Me | NMe₂ | 4-CF₃ | 7-Cl | 4-F-Ph | NMe₂ | 4-OCF₃ | 7-Cl | 4-F-Ph | NMe₂ |

TABLE 19

| R¹ | R² | R⁴ | X² | R¹ | R² | R⁴ | X² |
|---|---|---|---|---|---|---|---|
| 4-CF₃ | 5-F | Me | OH | 4-OCF₃ | 5-F | Me | OH |
| 4-CF₃ | 5-F | iPr | OH | 4-OCF₃ | 5-F | iPr | OH |
| 4-CF₃ | 5-F | Ph | OH | 4-OCF₃ | 5-F | Ph | OH |

TABLE 19-continued

| R¹ | R² | R⁴ | X² | R¹ | R² | R⁴ | X² |
|---|---|---|---|---|---|---|---|
| 4-CF₃ | 5-F | 4-F-Ph | OH | 4-OCF₃ | 5-F | 4-F-Ph | OH |
| 4-CF₃ | 5-F | 4-Cl-Ph | OH | 4-OCF₃ | 5-F | 4-Cl-Ph | OH |
| 4-CF₃ | 5-Cl | Me | OH | 4-OCF₃ | 5-Cl | Me | OH |
| 4-CF₃ | 5-Cl | iPr | OH | 4-OCF₃ | 5-Cl | iPr | OH |
| 4-CF₃ | 5-Cl | Ph | OH | 4-OCF₃ | 5-Cl | Ph | OH |
| 4-CF₃ | 5-Cl | 4-F-Ph | OH | 4-OCF₃ | 5-Cl | 4-F-Ph | OH |
| 4-CF₃ | 5-Cl | 4-Cl-Ph | OH | 4-OCF₃ | 5-Cl | 4-Cl-Ph | OH |
| 4-CF₃ | 5-CF₃ | Me | OH | 4-OCF₃ | 5-CF₃ | Me | OH |
| 4-CF₃ | 5-CF₃ | iPr | OH | 4-OCF₃ | 5-CF₃ | iPr | OH |
| 4-CF₃ | 5-CF₃ | Ph | OH | 4-OCF₃ | 5-CF₃ | Ph | OH |
| 4-CF₃ | 5-CF₃ | 4-F-Ph | OH | 4-OCF₃ | 5-CF₃ | 4-F-Ph | OH |
| 4-CF₃ | 5-CF₃ | 4-Cl-Ph | OH | 4-OCF₃ | 5-CF₃ | 4-Cl-Ph | OH |
| 4-CF₃ | 5-OCF₃ | Me | OH | 4-OCF₃ | 5-OCF₃ | Me | OH |
| 4-CF₃ | 5-OCF₃ | iPr | OH | 4-OCF₃ | 5-OCF₃ | iPr | OH |
| 4-CF₃ | 5-OCF₃ | Ph | OH | 4-OCF₃ | 5-OCF₃ | Ph | OH |
| 4-CF₃ | 5-OCF₃ | 4-F-Ph | OH | 4-OCF₃ | 5-OCF₃ | 4-F-Ph | OH |
| 4-CF₃ | 5-OCF₃ | 4-Cl-Ph | OH | 4-OCF₃ | 5-OCF₃ | 4-Cl-Ph | OH |
| 4-CF₃ | 4-F | Me | OH | 4-OCF₃ | 4-F | Me | OH |
| 4-CF₃ | 4-F | iPr | OH | 4-OCF₃ | 4-F | iPr | OH |
| 4-CF₃ | 4-F | Ph | OH | 4-OCF₃ | 4-F | Ph | OH |
| 4-CF₃ | 4-F | 4-F-Ph | OH | 4-OCF₃ | 4-F | 4-F-Ph | OH |
| 4-CF₃ | 4-F | 4-Cl-Ph | OH | 4-OCF₃ | 4-F | 4-Cl-Ph | OH |
| 4-CF₃ | 5-F | Me | OMe | 4-OCF₃ | 5-F | Me | OMe |
| 4-CF₃ | 5-F | iPr | OMe | 4-OCF₃ | 5-F | iPr | OMe |
| 4-CF₃ | 5-F | Ph | OMe | 4-OCF₃ | 5-F | Ph | OMe |
| 4-CF₃ | 5-F | 4-F-Ph | OMe | 4-OCF₃ | 5-F | 4-F-Ph | OMe |
| 4-CF₃ | 5-F | 4-Cl-Ph | OMe | 4-OCF₃ | 5-F | 4-Cl-Ph | OMe |
| 4-CF₃ | 5-Cl | Me | OMe | 4-OCF₃ | 5-Cl | Me | OMe |
| 4-CF₃ | 5-Cl | iPr | OMe | 4-OCF₃ | 5-Cl | iPr | OMe |
| 4-CF₃ | 5-Cl | Ph | OMe | 4-OCF₃ | 5-Cl | Ph | OMe |
| 4-CF₃ | 5-Cl | 4-F-Ph | OMe | 4-OCF₃ | 5-Cl | 4-F-Ph | OMe |
| 4-CF₃ | 5-Cl | 4-Cl-Ph | OMe | 4-OCF₃ | 5-Cl | 4-Cl-Ph | OMe |
| 4-CF₃ | 5-CF₃ | Me | OMe | 4-OCF₃ | 5-CF₃ | Me | OMe |
| 4-CF₃ | 5-CF₃ | iPr | OMe | 4-OCF₃ | 5-CF₃ | iPr | OMe |
| 4-CF₃ | 5-CF₃ | Ph | OMe | 4-OCF₃ | 5-CF₃ | Ph | OMe |
| 4-CF₃ | 5-CF₃ | 4-F-Ph | OMe | 4-OCF₃ | 5-CF₃ | 4-F-Ph | OMe |
| 4-CF₃ | 5-CF₃ | 4-Cl-Ph | OMe | 4-OCF₃ | 5-CF₃ | 4-Cl-Ph | OMe |
| 4-CF₃ | 5-OCF₃ | Me | OMe | 4-OCF₃ | 5-OCF₃ | Me | OMe |
| 4-CF₃ | 5-OCF₃ | iPr | OMe | 4-OCF₃ | 5-OCF₃ | iPr | OMe |
| 4-CF₃ | 5-OCF₃ | Ph | OMe | 4-OCF₃ | 5-OCF₃ | Ph | OMe |
| 4-CF₃ | 5-OCF₃ | 4-F-Ph | OMe | 4-OCF₃ | 5-OCF₃ | 4-F-Ph | OMe |
| 4-CF₃ | 5-OCF₃ | 4-Cl-Ph | OMe | 4-OCF₃ | 5-OCF₃ | 4-Cl-Ph | OMe |
| 4-CF₃ | 4-F | Me | OMe | 4-OCF₃ | 4-F | Me | OMe |
| 4-CF₃ | 4-F | iPr | OMe | 4-OCF₃ | 4-F | iPr | OMe |
| 4-CF₃ | 4-F | Ph | OMe | 4-OCF₃ | 4-F | Ph | OMe |
| 4-CF₃ | 4-F | 4-F-Ph | OMe | 4-OCF₃ | 4-F | 4-F-Ph | OMe |
| 4-CF₃ | 4-F | 4-Cl-Ph | OMe | 4-OCF₃ | 4-F | 4-Cl-Ph | OMe |
| 4-CF₃ | 5-F | Me | OCONHMe | 4-OCF₃ | 5-F | Me | OCONHMe |
| 4-CF₃ | 5-F | iPr | OCONHMe | 4-OCF₃ | 5-F | iPr | OCONHMe |
| 4-CF₃ | 5-F | Ph | OCONHMe | 4-OCF₃ | 5-F | Ph | OCONHMe |
| 4-CF₃ | 5-F | 4-F-Ph | OCONHMe | 4-OCF₃ | 5-F | 4-F-Ph | OCONHMe |
| 4-CF₃ | 5-F | 4-Cl-Ph | OCONHMe | 4-OCF₃ | 5-F | 4-Cl-Ph | OCONHMe |
| 4-CF₃ | 5-Cl | Me | OCONHMe | 4-OCF₃ | 5-Cl | Me | OCONHMe |
| 4-CF₃ | 5-Cl | iPr | OCONHMe | 4-OCF₃ | 5-Cl | iPr | OCONHMe |
| 4-CF₃ | 5-Cl | Ph | OCONHMe | 4-OCF₃ | 5-Cl | Ph | OCONHMe |
| 4-CF₃ | 5-Cl | 4-F-Ph | OCONHMe | 4-OCF₃ | 5-Cl | 4-F-Ph | OCONHMe |
| 4-CF₃ | 5-Cl | 4-Cl-Ph | OCONHMe | 4-OCF₃ | 5-Cl | 4-Cl-Ph | OCONHMe |
| 4-CF₃ | 5-CF₃ | Me | OCONHMe | 4-OCF₃ | 5-CF₃ | Me | OCONHMe |
| 4-CF₃ | 5-CF₃ | iPr | OCONHMe | 4-OCF₃ | 5-CF₃ | iPr | OCONHMe |
| 4-CF₃ | 5-CF₃ | Ph | OCONHMe | 4-OCF₃ | 5-CF₃ | Ph | OCONHMe |
| 4-CF₃ | 5-CF₃ | 4-F-Ph | OCONHMe | 4-OCF₃ | 5-CF₃ | 4-F-Ph | OCONHMe |
| 4-CF₃ | 5-CF₃ | 4-Cl-Ph | OCONHMe | 4-OCF₃ | 5-CF₃ | 4-Cl-Ph | OCONHMe |
| 4-CF₃ | 5-OCF₃ | Me | OCONHMe | 4-OCF₃ | 5-OCF₃ | Me | OCONHMe |
| 4-CF₃ | 5-OCF₃ | iPr | OCONHMe | 4-OCF₃ | 5-OCF₃ | iPr | OCONHMe |
| 4-CF₃ | 5-OCF₃ | Ph | OCONHMe | 4-OCF₃ | 5-OCF₃ | Ph | OCONHMe |
| 4-CF₃ | 5-OCF₃ | 4-F-Ph | OCONHMe | 4-OCF₃ | 5-OCF₃ | 4-F-Ph | OCONHMe |
| 4-CF₃ | 5-OCF₃ | 4-Cl-Ph | OCONHMe | 4-OCF₃ | 5-OCF₃ | 4-Cl-Ph | OCONHMe |
| 4-CF₃ | 4-F | Me | OCONHMe | 4-OCF₃ | 4-F | Me | OCONHMe |
| 4-CF₃ | 4-F | iPr | OCONHMe | 4-OCF₃ | 4-F | iPr | OCONHMe |
| 4-CF₃ | 4-F | Ph | OCONHMe | 4-OCF₃ | 4-F | Ph | OCONHMe |
| 4-CF₃ | 4-F | 4-F-Ph | OCONHMe | 4-OCF₃ | 4-F | 4-F-Ph | OCONHMe |
| 4-CF₃ | 4-F | 4-Cl-Ph | OCONHMe | 4-OCF₃ | 4-F | 4-Cl-Ph | OCONHMe |
| 4-CF₃ | 5-F | Me | CN | 4-OCF₃ | 5-F | Me | CN |
| 4-CF₃ | 5-F | iPr | CN | 4-OCF₃ | 5-F | iPr | CN |
| 4-CF₃ | 5-F | Ph | CN | 4-OCF₃ | 5-F | Ph | CN |
| 4-CF₃ | 5-F | 4-F-Ph | CN | 4-OCF₃ | 5-F | 4-F-Ph | CN |
| 4-CF₃ | 5-F | 4-Cl-Ph | CN | 4-OCF₃ | 5-F | 4-Cl-Ph | CN |
| 4-CF₃ | 5-Cl | Me | CN | 4-OCF₃ | 5-Cl | Me | CN |
| 4-CF₃ | 5-Cl | iPr | CN | 4-OCF₃ | 5-Cl | iPr | CN |
| 4-CF₃ | 5-Cl | Ph | CN | 4-OCF₃ | 5-Cl | Ph | CN |
| 4-CF₃ | 5-Cl | 4-F-Ph | CN | 4-OCF₃ | 5-Cl | 4-F-Ph | CN |

TABLE 19-continued

| R¹ | R² | R⁴ | X² | R¹ | R² | R⁴ | X² |
|---|---|---|---|---|---|---|---|
| 4-CF₃ | 5-Cl | 4-Cl-Ph | CN | 4-OCF₃ | 5-Cl | 4-Cl-Ph | CN |
| 4-CF₃ | 5-CF₃ | Me | CN | 4-OCF₃ | 5-CF₃ | Me | CN |
| 4-CF₃ | 5-CF₃ | iPr | CN | 4-OCF₃ | 5-CF₃ | iPr | CN |
| 4-CF₃ | 5-CF₃ | Ph | CN | 4-OCF₃ | 5-CF₃ | Ph | CN |
| 4-CF₃ | 5-CF₃ | 4-F-Ph | CN | 4-OCF₃ | 5-CF₃ | 4-F-Ph | CN |
| 4-CF₃ | 5-CF₃ | 4-Cl-Ph | CN | 4-OCF₃ | 5-CF₃ | 4-Cl-Ph | CN |
| 4-CF₃ | 5-OCF₃ | Me | CN | 4-OCF₃ | 5-OCF₃ | Me | CN |
| 4-CF₃ | 5-OCF₃ | iPr | CN | 4-OCF₃ | 5-OCF₃ | iPr | CN |
| 4-CF₃ | 5-OCF₃ | Ph | CN | 4-OCF₃ | 5-OCF₃ | Ph | CN |
| 4-CF₃ | 5-OCF₃ | 4-F-Ph | CN | 4-OCF₃ | 5-OCF₃ | 4-F-Ph | CN |
| 4-CF₃ | 5-OCF₃ | 4-Cl-Ph | CN | 4-OCF₃ | 5-OCF₃ | 4-Cl-Ph | CN |
| 4-CF₃ | 4-F | Me | CN | 4-OCF₃ | 4-F | Me | CN |
| 4-CF₃ | 4-F | iPr | CN | 4-OCF₃ | 4-F | iPr | CN |
| 4-CF₃ | 4-F | Ph | CN | 4-OCF₃ | 4-F | Ph | CN |
| 4-CF₃ | 4-F | 4-F-Ph | CN | 4-OCF₃ | 4-F | 4-F-Ph | CN |
| 4-CF₃ | 4-F | 4-Cl-Ph | CN | 4-OCF₃ | 4-F | 4-Cl-Ph | CN |
| 4-CF₃ | 5-F | Me | NMe₂ | 4-OCF₃ | 5-F | Me | NMe₂ |
| 4-CF₃ | 5-F | iPr | NMe₂ | 4-OCF₃ | 5-F | iPr | NMe₂ |
| 4-CF₃ | 5-F | Ph | NMe₂ | 4-OCF₃ | 5-F | Ph | NMe₂ |
| 4-CF₃ | 5-F | 4-F-Ph | NMe₂ | 4-OCF₃ | 5-F | 4-F-Ph | NMe₂ |
| 4-CF₃ | 5-F | 4-Cl-Ph | NMe₂ | 4-OCF₃ | 5-F | 4-Cl-Ph | NMe₂ |
| 4-CF₃ | 5-Cl | Me | NMe₂ | 4-OCF₃ | 5-Cl | Me | NMe₂ |
| 4-CF₃ | 5-Cl | iPr | NMe₂ | 4-OCF₃ | 5-Cl | iPr | NMe₂ |
| 4-CF₃ | 5-Cl | Ph | NMe₂ | 4-OCF₃ | 5-Cl | Ph | NMe₂ |
| 4-CF₃ | 5-Cl | 4-F-Ph | NMe₂ | 4-OCF₃ | 5-Cl | 4-F-Ph | NMe₂ |
| 4-CF₃ | 5-Cl | 4-Cl-Ph | NMe₂ | 4-OCF₃ | 5-Cl | 4-Cl-Ph | NMe₂ |
| 4-CF₃ | 5-CF₃ | Me | NMe₂ | 4-OCF₃ | 5-CF₃ | Me | NMe₂ |
| 4-CF₃ | 5-CF₃ | iPr | NMe₂ | 4-OCF₃ | 5-CF₃ | iPr | NMe₂ |
| 4-CF₃ | 5-CF₃ | Ph | NMe₂ | 4-OCF₃ | 5-CF₃ | Ph | NMe₂ |
| 4-CF₃ | 5-CF₃ | 4-F-Ph | NMe₂ | 4-OCF₃ | 5-CF₃ | 4-F-Ph | NMe₂ |
| 4-CF₃ | 5-CF₃ | 4-Cl-Ph | NMe₂ | 4-OCF₃ | 5-CF₃ | 4-Cl-Ph | NMe₂ |
| 4-CF₃ | 5-OCF₃ | Me | NMe₂ | 4-OCF₃ | 5-OCF₃ | Me | NMe₂ |
| 4-CF₃ | 5-OCF₃ | iPr | NMe₂ | 4-OCF₃ | 5-OCF₃ | iPr | NMe₂ |
| 4-CF₃ | 5-OCF₃ | Ph | NMe₂ | 4-OCF₃ | 5-OCF₃ | Ph | NMe₂ |
| 4-CF₃ | 5-OCF₃ | 4-F-Ph | NMe₂ | 4-OCF₃ | 5-OCF₃ | 4-F-Ph | NMe₂ |
| 4-CF₃ | 5-OCF₃ | 4-Cl-Ph | NMe₂ | 4-OCF₃ | 5-OCF₃ | 4-Cl-Ph | NMe₂ |
| 4-CF₃ | 4-F | Me | NMe₂ | 4-OCF₃ | 4-F | Me | NMe₂ |
| 4-CF₃ | 4-F | iPr | NMe₂ | 4-OCF₃ | 4-F | iPr | NMe₂ |
| 4-CF₃ | 4-F | Ph | NMe₂ | 4-OCF₃ | 4-F | Ph | NMe₂ |
| 4-CF₃ | 4-F | 4-F-Ph | NMe₂ | 4-OCF₃ | 4-F | 4-F-Ph | NMe₂ |
| 4-CF₃ | 4-F | 4-Cl-Ph | NMe₂ | 4-OCF₃ | 4-F | 4-Cl-Ph | NMe₂ |

TABLE 20

| R¹ | R² | R⁴ | X² | R¹ | R² | R⁴ | X² |
|---|---|---|---|---|---|---|---|
| 4-CF₃ | 5-F | Me | OH | 4-OCF₃ | 5-F | Me | OH |
| 4-CF₃ | 5-F | iPr | OH | 4-OCF₃ | 5-F | iPr | OH |
| 4-CF₃ | 5-F | Ph | OH | 4-OCF₃ | 5-F | Ph | OH |
| 4-CF₃ | 5-F | 4-F-Ph | OH | 4-OCF₃ | 5-F | 4-F-Ph | OH |
| 4-CF₃ | 5-F | 4-Cl-Ph | OH | 4-OCF₃ | 5-F | 4-Cl-Ph | OH |
| 4-CF₃ | 5-Cl | Me | OH | 4-OCF₃ | 5-Cl | Me | OH |
| 4-CF₃ | 5-Cl | iPr | OH | 4-OCF₃ | 5-Cl | iPr | OH |
| 4-CF₃ | 5-Cl | Ph | OH | 4-OCF₃ | 5-Cl | Ph | OH |
| 4-CF₃ | 5-Cl | 4-F-Ph | OH | 4-OCF₃ | 5-Cl | 4-F-Ph | OH |
| 4-CF₃ | 5-Cl | 4-Cl-Ph | OH | 4-OCF₃ | 5-Cl | 4-Cl-Ph | OH |
| 4-CF₃ | 5-CF₃ | Me | OH | 4-OCF₃ | 5-CF₃ | Me | OH |
| 4-CF₃ | 5-CF₃ | iPr | OH | 4-OCF₃ | 5-CF₃ | iPr | OH |
| 4-CF₃ | 5-CF₃ | Ph | OH | 4-OCF₃ | 5-CF₃ | Ph | OH |
| 4-CF₃ | 5-CF₃ | 4-F-Ph | OH | 4-OCF₃ | 5-CF₃ | 4-F-Ph | OH |
| 4-CF₃ | 5-CF₃ | 4-Cl-Ph | OH | 4-OCF₃ | 5-CF₃ | 4-Cl-Ph | OH |
| 4-CF₃ | 5-OCF₃ | Me | OH | 4-OCF₃ | 5-OCF₃ | Me | OH |
| 4-CF₃ | 5-OCF₃ | iPr | OH | 4-OCF₃ | 5-OCF₃ | iPr | OH |
| 4-CF₃ | 5-OCF₃ | Ph | OH | 4-OCF₃ | 5-OCF₃ | Ph | OH |
| 4-CF₃ | 5-OCF₃ | 4-F-Ph | OH | 4-OCF₃ | 5-OCF₃ | 4-F-Ph | OH |
| 4-CF₃ | 5-OCF₃ | 4-Cl-Ph | OH | 4-OCF₃ | 5-OCF₃ | 4-Cl-Ph | OH |
| 4-CF₃ | 4-F | Me | OH | 4-OCF₃ | 4-F | Me | OH |
| 4-CF₃ | 4-F | iPr | OH | 4-OCF₃ | 4-F | iPr | OH |
| 4-CF₃ | 4-F | Ph | OH | 4-OCF₃ | 4-F | Ph | OH |
| 4-CF₃ | 4-F | 4-F-Ph | OH | 4-OCF₃ | 4-F | 4-F-Ph | OH |
| 4-CF₃ | 4-F | 4-Cl-Ph | OH | 4-OCF₃ | 4-F | 4-Cl-Ph | OH |
| 4-CF₃ | 5-F | Me | OMe | 4-OCF₃ | 5-F | Me | OMe |
| 4-CF₃ | 5-F | iPr | OMe | 4-OCF₃ | 5-F | iPr | OMe |
| 4-CF₃ | 5-F | Ph | OMe | 4-OCF₃ | 5-F | Ph | OMe |
| 4-CF₃ | 5-F | 4-F-Ph | OMe | 4-OCF₃ | 5-F | 4-F-Ph | OMe |
| 4-CF₃ | 5-F | 4-Cl-Ph | OMe | 4-OCF₃ | 5-F | 4-Cl-Ph | OMe |
| 4-CF₃ | 5-Cl | Me | OMe | 4-OCF₃ | 5-Cl | Me | OMe |
| 4-CF₃ | 5-Cl | iPr | OMe | 4-OCF₃ | 5-Cl | iPr | OMe |
| 4-CF₃ | 5-Cl | Ph | OMe | 4-OCF₃ | 5-Cl | Ph | OMe |
| 4-CF₃ | 5-Cl | 4-F-Ph | OMe | 4-OCF₃ | 5-Cl | 4-F-Ph | OMe |

TABLE 20-continued

| R¹ | R² | R⁴ | X² | R¹ | R² | R⁴ | X² |
|---|---|---|---|---|---|---|---|
| 4-CF₃ | 5-Cl | 4-Cl-Ph | OMe | 4-OCF₃ | 5-Cl | 4-Cl-Ph | OMe |
| 4-CF₃ | 5-CF₃ | Me | OMe | 4-OCF₃ | 5-CF₃ | Me | OMe |
| 4-CF₃ | 5-CF₃ | iPr | OMe | 4-OCF₃ | 5-CF₃ | iPr | OMe |
| 4-CF₃ | 5-CF₃ | Ph | OMe | 4-OCF₃ | 5-CF₃ | Ph | OMe |
| 4-CF₃ | 5-CF₃ | 4-F-Ph | OMe | 4-OCF₃ | 5-CF₃ | 4-F-Ph | OMe |
| 4-CF₃ | 5-CF₃ | 4-Cl-Ph | OMe | 4-OCF₃ | 5-CF₃ | 4-Cl-Ph | OMe |
| 4-CF₃ | 5-OCF₃ | Me | OMe | 4-OCF₃ | 5-OCF₃ | Me | OMe |
| 4-CF₃ | 5-OCF₃ | iPr | OMe | 4-OCF₃ | 5-OCF₃ | iPr | OMe |
| 4-CF₃ | 5-OCF₃ | Ph | OMe | 4-OCF₃ | 5-OCF₃ | Ph | OMe |
| 4-CF₃ | 5-OCF₃ | 4-F-Ph | OMe | 4-OCF₃ | 5-OCF₃ | 4-F-Ph | OMe |
| 4-CF₃ | 5-OCF₃ | 4-Cl-Ph | OMe | 4-OCF₃ | 5-OCF₃ | 4-Cl-Ph | OMe |
| 4-CF₃ | 4-F | Me | OMe | 4-OCF₃ | 4-F | Me | OMe |
| 4-CF₃ | 4-F | iPr | OMe | 4-OCF₃ | 4-F | iPr | OMe |
| 4-CF₃ | 4-F | Ph | OMe | 4-OCF₃ | 4-F | Ph | OMe |
| 4-CF₃ | 4-F | 4-F-Ph | OMe | 4-OCF₃ | 4-F | 4-F-Ph | OMe |
| 4-CF₃ | 4-F | 4-Cl-Ph | OMe | 4-OCF₃ | 4-F | 4-Cl-Ph | OMe |
| 4-CF₃ | 5-F | Me | OCONHMe | 4-OCF₃ | 5-F | Me | OCONHMe |
| 4-CF₃ | 5-F | iPr | OCONHMe | 4-OCF₃ | 5-F | iPr | OCONHMe |
| 4-CF₃ | 5-F | Ph | OCONHMe | 4-OCF₃ | 5-F | Ph | OCONHMe |
| 4-CF₃ | 5-F | 4-F-Ph | OCONHMe | 4-OCF₃ | 5-F | 4-F-Ph | OCONHMe |
| 4-CF₃ | 5-F | 4-Cl-Ph | OCONHMe | 4-OCF₃ | 5-F | 4-Cl-Ph | OCONHMe |
| 4-CF₃ | 5-Cl | Me | OCONHMe | 4-OCF₃ | 5-Cl | Me | OCONHMe |
| 4-CF₃ | 5-Cl | iPr | OCONHMe | 4-OCF₃ | 5-Cl | iPr | OCONHMe |
| 4-CF₃ | 5-Cl | Ph | OCONHMe | 4-OCF₃ | 5-Cl | Ph | OCONHMe |
| 4-CF₃ | 5-Cl | 4-F-Ph | OCONHMe | 4-OCF₃ | 5-Cl | 4-F-Ph | OCONHMe |
| 4-CF₃ | 5-Cl | 4-Cl-Ph | OCONHMe | 4-OCF₃ | 5-Cl | 4-Cl-Ph | OCONHMe |
| 4-CF₃ | 5-CF₃ | Me | OCONHMe | 4-OCF₃ | 5-CF₃ | Me | OCONHMe |
| 4-CF₃ | 5-CF₃ | iPr | OCONHMe | 4-OCF₃ | 5-CF₃ | iPr | OCONHMe |
| 4-CF₃ | 5-CF₃ | Ph | OCONHMe | 4-OCF₃ | 5-CF₃ | Ph | OCONHMe |
| 4-CF₃ | 5-CF₃ | 4-F-Ph | OCONHMe | 4-OCF₃ | 5-CF₃ | 4-F-Ph | OCONHMe |
| 4-CF₃ | 5-CF₃ | 4-Cl-Ph | OCONHMe | 4-OCF₃ | 5-CF₃ | 4-Cl-Ph | OCONHMe |
| 4-CF₃ | 5-OCF₃ | Me | OCONHMe | 4-OCF₃ | 5-OCF₃ | Me | OCONHMe |
| 4-CF₃ | 5-OCF₃ | iPr | OCONHMe | 4-OCF₃ | 5-OCF₃ | iPr | OCONHMe |
| 4-CF₃ | 5-OCF₃ | Ph | OCONHMe | 4-OCF₃ | 5-OCF₃ | Ph | OCONHMe |
| 4-CF₃ | 5-OCF₃ | 4-F-Ph | OCONHMe | 4-OCF₃ | 5-OCF₃ | 4-F-Ph | OCONHMe |
| 4-CF₃ | 5-OCF₃ | 4-Cl-Ph | OCONHMe | 4-OCF₃ | 5-OCF₃ | 4-Cl-Ph | OCONHMe |
| 4-CF₃ | 4-F | Me | OCONHMe | 4-OCF₃ | 4-F | Me | OCONHMe |
| 4-CF₃ | 4-F | iPr | OCONHMe | 4-OCF₃ | 4-F | iPr | OCONHMe |
| 4-CF₃ | 4-F | Ph | OCONHMe | 4-OCF₃ | 4-F | Ph | OCONHMe |
| 4-CF₃ | 4-F | 4-F-Ph | OCONHMe | 4-OCF₃ | 4-F | 4-F-Ph | OCONHMe |
| 4-CF₃ | 4-F | 4-Cl-Ph | OCONHMe | 4-OCF₃ | 4-F | 4-Cl-Ph | OCONHMe |
| 4-CF₃ | 5-F | Me | CN | 4-OCF₃ | 5-F | Me | CN |
| 4-CF₃ | 5-F | iPr | CN | 4-OCF₃ | 5-F | iPr | CN |
| 4-CF₃ | 5-F | Ph | CN | 4-OCF₃ | 5-F | Ph | CN |
| 4-CF₃ | 5-F | 4-F-Ph | CN | 4-OCF₃ | 5-F | 4-F-Ph | CN |
| 4-CF₃ | 5-F | 4-Cl-Ph | CN | 4-OCF₃ | 5-F | 4-Cl-Ph | CN |
| 4-CF₃ | 5-Cl | Me | CN | 4-OCF₃ | 5-Cl | Me | CN |
| 4-CF₃ | 5-Cl | iPr | CN | 4-OCF₃ | 5-Cl | iPr | CN |
| 4-CF₃ | 5-Cl | Ph | CN | 4-OCF₃ | 5-Cl | Ph | CN |
| 4-CF₃ | 5-Cl | 4-F-Ph | CN | 4-OCF₃ | 5-Cl | 4-F-Ph | CN |
| 4-CF₃ | 5-Cl | 4-Cl-Ph | CN | 4-OCF₃ | 5-Cl | 4-Cl-Ph | CN |
| 4-CF₃ | 5-CF₃ | Me | CN | 4-OCF₃ | 5-CF₃ | Me | CN |
| 4-CF₃ | 5-CF₃ | iPr | CN | 4-OCF₃ | 5-CF₃ | iPr | CN |
| 4-CF₃ | 5-CF₃ | Ph | CN | 4-OCF₃ | 5-CF₃ | Ph | CN |
| 4-CF₃ | 5-CF₃ | 4-F-Ph | CN | 4-OCF₃ | 5-CF₃ | 4-F-Ph | CN |
| 4-CF₃ | 5-CF₃ | 4-Cl-Ph | CN | 4-OCF₃ | 5-CF₃ | 4-Cl-Ph | CN |
| 4-CF₃ | 5-OCF₃ | Me | CN | 4-OCF₃ | 5-OCF₃ | Me | CN |
| 4-CF₃ | 5-OCF₃ | iPr | CN | 4-OCF₃ | 5-OCF₃ | iPr | CN |
| 4-CF₃ | 5-OCF₃ | Ph | CN | 4-OCF₃ | 5-OCF₃ | Ph | CN |
| 4-CF₃ | 5-OCF₃ | 4-F-Ph | CN | 4-OCF₃ | 5-OCF₃ | 4-F-Ph | CN |
| 4-CF₃ | 5-OCF₃ | 4-Cl-Ph | CN | 4-OCF₃ | 5-OCF₃ | 4-Cl-Ph | CN |
| 4-CF₃ | 4-F | Me | CN | 4-OCF₃ | 4-F | Me | CN |
| 4-CF₃ | 4-F | iPr | CN | 4-OCF₃ | 4-F | iPr | CN |
| 4-CF₃ | 4-F | Ph | CN | 4-OCF₃ | 4-F | Ph | CN |
| 4-CF₃ | 4-F | 4-F-Ph | CN | 4-OCF₃ | 4-F | 4-F-Ph | CN |
| 4-CF₃ | 4-F | 4-Cl-Ph | CN | 4-OCF₃ | 4-F | 4-Cl-Ph | CN |
| 4-CF₃ | 5-F | Me | NMe₂ | 4-OCF₃ | 5-F | Me | NMe₂ |
| 4-CF₃ | 5-F | iPr | NMe₂ | 4-OCF₃ | 5-F | iPr | NMe₂ |
| 4-CF₃ | 5-F | Ph | NMe₂ | 4-OCF₃ | 5-F | Ph | NMe₂ |
| 4-CF₃ | 5-F | 4-F-Ph | NMe₂ | 4-OCF₃ | 5-F | 4-F-Ph | NMe₂ |
| 4-CF₃ | 5-F | 4-Cl-Ph | NMe₂ | 4-OCF₃ | 5-F | 4-Cl-Ph | NMe₂ |
| 4-CF₃ | 5-Cl | Me | NMe₂ | 4-OCF₃ | 5-Cl | Me | NMe₂ |
| 4-CF₃ | 5-Cl | iPr | NMe₂ | 4-OCF₃ | 5-Cl | iPr | NMe₂ |
| 4-CF₃ | 5-Cl | Ph | NMe₂ | 4-OCF₃ | 5-Cl | Ph | NMe₂ |
| 4-CF₃ | 5-Cl | 4-F-Ph | NMe₂ | 4-OCF₃ | 5-Cl | 4-F-Ph | NMe₂ |
| 4-CF₃ | 5-Cl | 4-Cl-Ph | NMe₂ | 4-OCF₃ | 5-Cl | 4-Cl-Ph | NMe₂ |
| 4-CF₃ | 5-CF₃ | Me | NMe₂ | 4-OCF₃ | 5-CF₃ | Me | NMe₂ |
| 4-CF₃ | 5-CF₃ | iPr | NMe₂ | 4-OCF₃ | 5-CF₃ | iPr | NMe₂ |
| 4-CF₃ | 5-CF₃ | Ph | NMe₂ | 4-OCF₃ | 5-CF₃ | Ph | NMe₂ |
| 4-CF₃ | 5-CF₃ | 4-F-Ph | NMe₂ | 4-OCF₃ | 5-CF₃ | 4-F-Ph | NMe₂ |
| 4-CF₃ | 5-CF₃ | 4-Cl-Ph | NMe₂ | 4-OCF₃ | 5-CF₃ | 4-Cl-Ph | NMe₂ |

TABLE 20-continued

| R¹ | R² | R⁴ | X² | R¹ | R² | R⁴ | X² |
|---|---|---|---|---|---|---|---|
| 4-CF₃ | 5-OCF₃ | Me | NMe₂ | 4-OCF₃ | 5-OCF₃ | Me | NMe₂ |
| 4-CF₃ | 5-OCF₃ | iPr | NMe₂ | 4-OCF₃ | 5-OCF₃ | iPr | NMe₂ |
| 4-CF₃ | 5-OCF₃ | Ph | NMe₂ | 4-OCF₃ | 5-OCF₃ | Ph | NMe₂ |
| 4-CF₃ | 5-OCF₃ | 4-F-Ph | NMe₂ | 4-OCF₃ | 5-OCF₃ | 4-F-Ph | NMe₂ |
| 4-CF₃ | 5-OCF₃ | 4-Cl-Ph | NMe₂ | 4-OCF₃ | 5-OCF₃ | 4-Cl-Ph | NMe₂ |
| 4-CF₃ | 4-F | Me | NMe₂ | 4-OCF₃ | 4-F | Me | NMe₂ |
| 4-CF₃ | 4-F | iPr | NMe₂ | 4-OCF₃ | 4-F | iPr | NMe₂ |
| 4-CF₃ | 4-F | Ph | NMe₂ | 4-OCF₃ | 4-F | Ph | NMe₂ |
| 4-CF₃ | 4-F | 4-F-Ph | NMe₂ | 4-OCF₃ | 4-F | 4-F-Ph | NMe₂ |
| 4-CF₃ | 4-F | 4-Cl-Ph | NMe₂ | 4-OCF₃ | 4-F | 4-Cl-Ph | NMe₂ |

TABLE 21

| R¹ | R² | R³ | R⁵ | X² | R¹ | R² | R³ | R⁵ | X² |
|---|---|---|---|---|---|---|---|---|---|
| 4-CF₃ | 4-Cl | CO₂Me | H | OH | 4-O-CF₃ | 4-Cl | 4-F-Ph | H | CN |
| 4-CF₃ | 4-Cl | CO₂Me | H | OMe | 4-CF₃ | 4-Cl | CO₂Me | Me | OH |
| 4-CF₃ | 4-Cl | CO₂Me | H | OCONHMe | 4-CF₃ | 4-Cl | CO₂Me | Me | OMe |
| 4-CF₃ | 4-Cl | CO₂Me | H | CN | 4-CF₃ | 4-Cl | CO₂Me | Me | OCONHMe |
| 4-CF₃ | 4-CF₃ | CO₂Me | H | OH | 4-CF₃ | 4-Cl | CO₂Me | Me | CN |
| 4-CF₃ | 4-CF₃ | CO₂Me | H | OMe | 4-CF₃ | 4-CF₃ | CO₂Me | Me | OH |
| 4-CF₃ | 4-CF₃ | CO₂Me | H | OCONHMe | 4-CF₃ | 4-CF₃ | CO₂Me | Me | OMe |
| 4-CF₃ | 4-CF₃ | CO₂Me | H | CN | 4-CF₃ | 4-CF₃ | CO₂Me | Me | OCONHMe |
| 4-CF₃ | 4-Cl | 4-F-Ph | H | OH | 4-CF₃ | 4-CF₃ | CO₂Me | Me | CN |
| 4-CF₃ | 4-Cl | 4-F-Ph | H | OMe | 4-OCF₃ | 4-Cl | CO₂Me | Me | OH |
| 4-CF₃ | 4-Cl | 4-F-Ph | H | OCONHMe | 4-OCF₃ | 4-Cl | CO₂Me | Me | OMe |
| 4-CF₃ | 4-Cl | 4-F-Ph | H | CN | 4-OCF₃ | 4-Cl | CO₂Me | Me | OCONHMe |
| 4-CF₃ | 4-CF₃ | 4-F-Ph | H | OH | 4-OCF₃ | 4-Cl | CO₂Me | Me | CN |
| 4-CF₃ | 4-CF₃ | 4-F-Ph | H | OMe | 4-OCF₃ | 4-CF₃ | CO₂Me | Me | OH |
| 4-CF₃ | 4-CF₃ | 4-F-Ph | H | OCONHMe | 4-OCF₃ | 4-CF₃ | CO₂Me | Me | OMe |
| 4-CF₃ | 4-CF₃ | 4-F-Ph | H | CN | 4-OCF₃ | 4-CF₃ | CO₂Me | Me | OCONHMe |
| 4-OCF₃ | 4-Cl | CO₂Me | H | OH | 4-OCF₃ | 4-CF₃ | CO₂Me | Me | CN |
| 4-OCF₃ | 4-Cl | CO₂Me | H | OMe | | | | | |
| 4-OCF₃ | 4-Cl | CO₂Me | H | OCONHMe | | | | | |
| 4-OCF₃ | 4-Cl | CO₂Me | H | CN | | | | | |
| 4-OCF₃ | 4-CF₃ | CO₂Me | H | OH | | | | | |
| 4-OCF₃ | 4-CF₃ | CO₂Me | H | OMe | | | | | |
| 4-OCF₃ | 4-CF₃ | CO₂Me | H | OCONHMe | | | | | |
| 4-OCF₃ | 4-CF₃ | CO₂Me | H | CN | | | | | |
| 4-OCF₃ | 4-Cl | 4-F-Ph | H | OH | | | | | |
| 4-OCF₃ | 4-Cl | 4-F-Ph | H | OMe | | | | | |
| 4-OCF₃ | 4-Cl | 4-F-Ph | H | OCONHMe | | | | | |

TABLE 22

| R¹ | R² | V | R¹ | R² | V |
|---|---|---|---|---|---|
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 7-F | O | 4-OCF₃ | 7-F | O |
| 4-CF₃ | 7-F | O | 4-OCF₃ | 7-F | O |
| 4-CF₃ | 7-F | O | 4-OCF₃ | 7-F | O |
| 4-CF₃ | 7-F | O | 4-OCF₃ | 7-F | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 6-F | O | 4-OCF₃ | 6-F | O |
| 4-CF₃ | 6-F | O | 4-OCF₃ | 6-F | O |
| 4-CF₃ | 6-F | O | 4-OCF₃ | 6-F | O |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |

TABLE 23

| R¹ | R² | V | R¹ | R² | V |
|---|---|---|---|---|---|
| 4-CF$_3$ | 7-F | CH$_2$ | 4-OCF$_3$ | 7-F | CH$_2$ |
| 4-CF$_3$ | 7-F | CH$_2$ | 4-OCF$_3$ | 7-F | CH$_2$ |
| 4-CF$_3$ | 7-F | CH$_2$ | 4-OCF$_3$ | 7-F | CH$_2$ |
| 4-CF$_3$ | 7-Cl | CH$_2$ | 4-OCF$_3$ | 7-Cl | CH$_2$ |
| 4-CF$_3$ | 7-Cl | CH$_2$ | 4-OCF$_3$ | 7-Cl | CH$_2$ |
| 4-CF$_3$ | 7-Cl | CH$_2$ | 4-OCF$_3$ | 7-Cl | CH$_2$ |
| 4-CF$_3$ | 7-CF$_3$ | CH$_2$ | 4-OCF$_3$ | 7-CF$_3$ | CH$_2$ |
| 4-CF$_3$ | 7-CF$_3$ | CH$_2$ | 4-OCF$_3$ | 7-CF$_3$ | CH$_2$ |
| 4-CF$_3$ | 7-CF$_3$ | CH$_2$ | 4-OCF$_3$ | 7-CF$_3$ | CH$_2$ |
| 4-CF$_3$ | 6-F | CH$_2$ | 4-OCF$_3$ | 6-F | CH$_2$ |
| 4-CF$_3$ | 6-F | CH$_2$ | 4-OCF$_3$ | 6-F | CH$_2$ |
| 4-CF$_3$ | 6-F | CH$_2$ | 4-OCF$_3$ | 6-F | CH$_2$ |
| 4-CF$_3$ | 7-F | O | 4-OCF$_3$ | 7-F | O |
| 4-CF$_3$ | 7-F | O | 4-OCF$_3$ | 7-F | O |
| 4-CF$_3$ | 7-F | O | 4-OCF$_3$ | 7-F | O |
| 4-CF$_3$ | 7-Cl | O | 4-OCF$_3$ | 7-Cl | O |
| 4-CF$_3$ | 7-Cl | O | 4-OCF$_3$ | 7-Cl | O |
| 4-CF$_3$ | 7-Cl | O | 4-OCF$_3$ | 7-Cl | O |
| 4-CF$_3$ | 7-CF$_3$ | O | 4-OCF$_3$ | 7-CF$_3$ | O |
| 4-CF$_3$ | 7-CF$_3$ | O | 4-OCF$_3$ | 7-CF$_3$ | O |
| 4-CF$_3$ | 7-CF$_3$ | O | 4-OCF$_3$ | 7-CF$_3$ | O |
| 4-CF$_3$ | 6-F | O | 4-OCF$_3$ | 6-F | O |
| 4-CF$_3$ | 6-F | O | 4-OCF$_3$ | 6-F | O |
| 4-CF$_3$ | 6-F | O | 4-OCF$_3$ | 6-F | O |
| 4-CF$_3$ | 7-F | NMe | 4-OCF$_3$ | 7-F | NMe |
| 4-CF$_3$ | 7-F | NMe | 4-OCF$_3$ | 7-F | NMe |
| 4-CF$_3$ | 7-F | NMe | 4-OCF$_3$ | 7-F | NMe |
| 4-CF$_3$ | 7-Cl | NMe | 4-OCF$_3$ | 7-Cl | NMe |
| 4-CF$_3$ | 7-Cl | NMe | 4-OCF$_3$ | 7-Cl | NMe |
| 4-CF$_3$ | 7-Cl | NMe | 4-OCF$_3$ | 7-Cl | NMe |
| 4-CF$_3$ | 7-CF$_3$ | NMe | 4-OCF$_3$ | 7-CF$_3$ | NMe |
| 4-CF$_3$ | 7-CF$_3$ | NMe | 4-OCF$_3$ | 7-CF$_3$ | NMe |
| 4-CF$_3$ | 7-CF$_3$ | NMe | 4-OCF$_3$ | 7-CF$_3$ | NMe |
| 4-CF$_3$ | 6-F | NMe | 4-OCF$_3$ | 6-F | NMe |
| 4-CF$_3$ | 6-F | NMe | 4-OCF$_3$ | 6-F | NMe |
| 4-CF$_3$ | 6-F | NMe | 4-OCF$_3$ | 6-F | NMe |
| 4-CF$_3$ | 7-F | NSO$_2$Me | 4-OCF$_3$ | 7-F | NSO$_2$Me |
| 4-CF$_3$ | 7-F | NSO$_2$Me | 4-OCF$_3$ | 7-F | NSO$_2$Me |
| 4-CF$_3$ | 7-F | NSO$_2$Me | 4-OCF$_3$ | 7-F | NSO$_2$Me |
| 4-CF$_3$ | 7-Cl | NSO$_2$Me | 4-OCF$_3$ | 7-Cl | NSO$_2$Me |
| 4-CF$_3$ | 7-Cl | NSO$_2$Me | 4-OCF$_3$ | 7-Cl | NSO$_2$Me |
| 4-CF$_3$ | 7-Cl | NSO$_2$Me | 4-OCF$_3$ | 7-Cl | NSO$_2$Me |
| 4-CF$_3$ | 7-CF$_3$ | NSO$_2$Me | 4-OCF$_3$ | 7-CF$_3$ | NSO$_2$Me |
| 4-CF$_3$ | 7-CF$_3$ | NSO$_2$Me | 4-OCF$_3$ | 7-CF$_3$ | NSO$_2$Me |
| 4-CF$_3$ | 7-CF$_3$ | NSO$_2$Me | 4-OCF$_3$ | 7-CF$_3$ | NSO$_2$Me |
| 4-CF$_3$ | 6-F | NSO$_2$Me | 4-OCF$_3$ | 6-F | NSO$_2$Me |
| 4-CF$_3$ | 6-F | NSO$_2$Me | 4-OCF$_3$ | 6-F | NSO$_2$Me |
| 4-CF$_3$ | 6-F | NSO$_2$Me | 4-OCF$_3$ | 6-F | NSO$_2$Me |

TABLE 24

| R¹ | R² | V | R¹ | R² | V |
|---|---|---|---|---|---|
| 4-CF$_3$ | 7-F | CH$_2$ | 4-OCF$_3$ | 7-F | CH$_2$ |
| 4-CF$_3$ | 7-F | CH$_2$ | 4-OCF$_3$ | 7-F | CH$_2$ |
| 4-CF$_3$ | 7-F | CH$_2$ | 4-OCF$_3$ | 7-F | CH$_2$ |
| 4-CF$_3$ | 7-Cl | CH$_2$ | 4-OCF$_3$ | 7-Cl | CH$_2$ |
| 4-CF$_3$ | 7-Cl | CH$_2$ | 4-OCF$_3$ | 7-Cl | CH$_2$ |
| 4-CF$_3$ | 7-Cl | CH$_2$ | 4-OCF$_3$ | 7-Cl | CH$_2$ |
| 4-CF$_3$ | 7-CF$_3$ | CH$_2$ | 4-OCF$_3$ | 7-CF$_3$ | CH$_2$ |
| 4-CF$_3$ | 7-CF$_3$ | CH$_2$ | 4-OCF$_3$ | 7-CF$_3$ | CH$_2$ |
| 4-CF$_3$ | 7-CF$_3$ | CH$_2$ | 4-OCF$_3$ | 7-CF$_3$ | CH$_2$ |
| 4-CF$_3$ | 6-F | CH$_2$ | 4-OCF$_3$ | 6-F | CH$_2$ |
| 4-CF$_3$ | 6-F | CH$_2$ | 4-OCF$_3$ | 6-F | CH$_2$ |
| 4-CF$_3$ | 6-F | CH$_2$ | 4-OCF$_3$ | 6-F | CH$_2$ |
| 4-CF$_3$ | 7-F | O | 4-OCF$_3$ | 7-F | O |
| 4-CF$_3$ | 7-F | O | 4-OCF$_3$ | 7-F | O |
| 4-CF$_3$ | 7-F | O | 4-OCF$_3$ | 7-F | O |
| 4-CF$_3$ | 7-Cl | O | 4-OCF$_3$ | 7-Cl | O |
| 4-CF$_3$ | 7-Cl | O | 4-OCF$_3$ | 7-Cl | O |
| 4-CF$_3$ | 7-Cl | O | 4-OCF$_3$ | 7-Cl | O |
| 4-CF$_3$ | 7-CF$_3$ | O | 4-OCF$_3$ | 7-CF$_3$ | O |
| 4-CF$_3$ | 7-CF$_3$ | O | 4-OCF$_3$ | 7-CF$_3$ | O |
| 4-CF$_3$ | 7-CF$_3$ | O | 4-OCF$_3$ | 7-CF$_3$ | O |
| 4-CF$_3$ | 6-F | O | 4-OCF$_3$ | 6-F | O |
| 4-CF$_3$ | 6-F | O | 4-OCF$_3$ | 6-F | O |
| 4-CF$_3$ | 6-F | O | 4-OCF$_3$ | 6-F | O |
| 4-CF$_3$ | 7-F | NMe | 4-OCF$_3$ | 7-F | NMe |
| 4-CF$_3$ | 7-F | NMe | 4-OCF$_3$ | 7-F | NMe |
| 4-CF$_3$ | 7-F | NMe | 4-OCF$_3$ | 7-F | NMe |
| 4-CF$_3$ | 7-Cl | NMe | 4-OCF$_3$ | 7-Cl | NMe |
| 4-CF$_3$ | 7-Cl | NMe | 4-OCF$_3$ | 7-Cl | NMe |
| 4-CF$_3$ | 7-Cl | NMe | 4-OCF$_3$ | 7-Cl | NMe |
| 4-CF$_3$ | 7-CF$_3$ | NMe | 4-OCF$_3$ | 7-CF$_3$ | NMe |
| 4-CF$_3$ | 7-CF$_3$ | NMe | 4-OCF$_3$ | 7-CF$_3$ | NMe |
| 4-CF$_3$ | 7-CF$_3$ | NMe | 4-OCF$_3$ | 7-CF$_3$ | NMe |
| 4-CF$_3$ | 6-F | NMe | 4-OCF$_3$ | 6-F | NMe |
| 4-CF$_3$ | 6-F | NMe | 4-OCF$_3$ | 6-F | NMe |
| 4-CF$_3$ | 6-F | NMe | 4-OCF$_3$ | 6-F | NMe |
| 4-CF$_3$ | 7-F | NSO$_2$Me | 4-OCF$_3$ | 7-F | NSO$_2$Me |
| 4-CF$_3$ | 7-F | NSO$_2$Me | 4-OCF$_3$ | 7-F | NSO$_2$Me |
| 4-CF$_3$ | 7-F | NSO$_2$Me | 4-OCF$_3$ | 7-F | NSO$_2$Me |
| 4-CF$_3$ | 7-Cl | NSO$_2$Me | 4-OCF$_3$ | 7-Cl | NSO$_2$Me |
| 4-CF$_3$ | 7-Cl | NSO$_2$Me | 4-OCF$_3$ | 7-Cl | NSO$_2$Me |
| 4-CF$_3$ | 7-Cl | NSO$_2$Me | 4-OCF$_3$ | 7-Cl | NSO$_2$Me |
| 4-CF$_3$ | 7-CF$_3$ | NSO$_2$Me | 4-OCF$_3$ | 7-CF$_3$ | NSO$_2$Me |
| 4-CF$_3$ | 7-CF$_3$ | NSO$_2$Me | 4-OCF$_3$ | 7-CF$_3$ | NSO$_2$Me |
| 4-CF$_3$ | 7-CF$_3$ | NSO$_2$Me | 4-OCF$_3$ | 7-CF$_3$ | NSO$_2$Me |
| 4-CF$_3$ | 6-F | NSO$_2$Me | 4-OCF$_3$ | 6-F | NSO$_2$Me |
| 4-CF$_3$ | 6-F | NSO$_2$Me | 4-OCF$_3$ | 6-F | NSO$_2$Me |
| 4-CF$_3$ | 6-F | NSO$_2$Me | 4-OCF$_3$ | 6-F | NSO$_2$Me |

TABLE 25

| R¹ | R² | V | R¹ | R² | V |
|---|---|---|---|---|---|
| 4-CF$_3$ | 7-F | CH$_2$ | 4-OCF$_3$ | 7-F | CH$_2$ |
| 4-CF$_3$ | 7-F | CH$_2$ | 4-OCF$_3$ | 7-F | CH$_2$ |
| 4-CF$_3$ | 7-F | CH$_2$ | 4-OCF$_3$ | 7-F | CH$_2$ |
| 4-CF$_3$ | 7-Cl | CH$_2$ | 4-OCF$_3$ | 7-Cl | CH$_2$ |
| 4-CF$_3$ | 7-Cl | CH$_2$ | 4-OCF$_3$ | 7-Cl | CH$_2$ |
| 4-CF$_3$ | 7-Cl | CH$_2$ | 4-OCF$_3$ | 7-Cl | CH$_2$ |
| 4-CF$_3$ | 7-CF$_3$ | CH$_2$ | 4-OCF$_3$ | 7-CF$_3$ | CH$_2$ |
| 4-CF$_3$ | 7-CF$_3$ | CH$_2$ | 4-OCF$_3$ | 7-CF$_3$ | CH$_2$ |
| 4-CF$_3$ | 7-CF$_3$ | CH$_2$ | 4-OCF$_3$ | 7-CF$_3$ | CH$_2$ |
| 4-CF$_3$ | 6-F | CH$_2$ | 4-OCF$_3$ | 6-F | CH$_2$ |
| 4-CF$_3$ | 6-F | CH$_2$ | 4-OCF$_3$ | 6-F | CH$_2$ |
| 4-CF$_3$ | 6-F | CH$_2$ | 4-OCF$_3$ | 6-F | CH$_2$ |
| 4-CF$_3$ | 7-F | O | 4-OCF$_3$ | 7-F | O |
| 4-CF$_3$ | 7-F | O | 4-OCF$_3$ | 7-F | O |
| 4-CF$_3$ | 7-F | O | 4-OCF$_3$ | 7-F | O |
| 4-CF$_3$ | 7-Cl | O | 4-OCF$_3$ | 7-Cl | O |
| 4-CF$_3$ | 7-Cl | O | 4-OCF$_3$ | 7-Cl | O |

TABLE 25-continued

| R¹ | R² | V | R¹ | R² | V |
|---|---|---|---|---|---|
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 6-F | O | 4-OCF₃ | 6-F | O |
| 4-CF₃ | 6-F | O | 4-OCF₃ | 6-F | O |
| 4-CF₃ | 6-F | O | 4-OCF₃ | 6-F | O |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |

TABLE 26

| R¹ | R² | V | R¹ | R² | V |
|---|---|---|---|---|---|
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 7-F | O | 4-OCF₃ | 7-F | O |
| 4-CF₃ | 7-F | O | 4-OCF₃ | 7-F | O |
| 4-CF₃ | 7-F | O | 4-OCF₃ | 7-F | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 6-F | O | 4-OCF₃ | 6-F | O |
| 4-CF₃ | 6-F | O | 4-OCF₃ | 6-F | O |
| 4-CF₃ | 6-F | O | 4-OCF₃ | 6-F | O |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |

TABLE 27

| R¹ | R² | V | R¹ | R² | V |
|---|---|---|---|---|---|
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 7-F | O | 4-OCF₃ | 7-F | O |
| 4-CF₃ | 7-F | O | 4-OCF₃ | 7-F | O |
| 4-CF₃ | 7-F | O | 4-OCF₃ | 7-F | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 6-F | O | 4-OCF₃ | 6-F | O |
| 4-CF₃ | 6-F | O | 4-OCF₃ | 6-F | O |
| 4-CF₃ | 6-F | O | 4-OCF₃ | 6-F | O |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |

TABLE 27-continued

| R¹ | R² | V | R¹ | R² | V |
|---|---|---|---|---|---|
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |

TABLE 28

| R¹ | R² | V | R¹ | R² | V |
|---|---|---|---|---|---|
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 7-F | O | 4-OCF₃ | 7-F | O |
| 4-CF₃ | 7-F | O | 4-OCF₃ | 7-F | O |
| 4-CF₃ | 7-F | O | 4-OCF₃ | 7-F | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 6-F | O | 4-OCF₃ | 6-F | O |
| 4-CF₃ | 6-F | O | 4-OCF₃ | 6-F | O |
| 4-CF₃ | 6-F | O | 4-OCF₃ | 6-F | O |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |

TABLE 29

| R¹ | R² | V | R¹ | R² | V |
|---|---|---|---|---|---|
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 7-F | O | 4-OCF₃ | 7-F | O |
| 4-CF₃ | 7-F | O | 4-OCF₃ | 7-F | O |
| 4-CF₃ | 7-F | O | 4-OCF₃ | 7-F | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 6-F | O | 4-OCF₃ | 6-F | O |
| 4-CF₃ | 6-F | O | 4-OCF₃ | 6-F | O |
| 4-CF₃ | 6-F | O | 4-OCF₃ | 6-F | O |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |

TABLE 30

| R¹ | R² | V | R¹ | R² | V |
|---|---|---|---|---|---|
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 7-F | O | 4-OCF₃ | 7-F | O |
| 4-CF₃ | 7-F | O | 4-OCF₃ | 7-F | O |
| 4-CF₃ | 7-F | O | 4-OCF₃ | 7-F | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 6-F | O | 4-OCF₃ | 6-F | O |
| 4-CF₃ | 6-F | O | 4-OCF₃ | 6-F | O |
| 4-CF₃ | 6-F | O | 4-OCF₃ | 6-F | O |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |

TABLE 31

| R¹ | R² | V | R¹ | R² | V |
|---|---|---|---|---|---|
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-F | CH₂ | 4-OCF₃ | 7-F | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-Cl | CH₂ | 4-OCF₃ | 7-Cl | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 7-CF₃ | CH₂ | 4-OCF₃ | 7-CF₃ | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 6-F | CH₂ | 4-OCF₃ | 6-F | CH₂ |
| 4-CF₃ | 7-F | O | 4-OCF₃ | 7-F | O |
| 4-CF₃ | 7-F | O | 4-OCF₃ | 7-F | O |
| 4-CF₃ | 7-F | O | 4-OCF₃ | 7-F | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-Cl | O | 4-OCF₃ | 7-Cl | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 7-CF₃ | O | 4-OCF₃ | 7-CF₃ | O |
| 4-CF₃ | 6-F | O | 4-OCF₃ | 6-F | O |
| 4-CF₃ | 6-F | O | 4-OCF₃ | 6-F | O |
| 4-CF₃ | 6-F | O | 4-OCF₃ | 6-F | O |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-F | NMe | 4-OCF₃ | 7-F | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-Cl | NMe | 4-OCF₃ | 7-Cl | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 7-CF₃ | NMe | 4-OCF₃ | 7-CF₃ | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 6-F | NMe | 4-OCF₃ | 6-F | NMe |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-F | NSO₂Me | 4-OCF₃ | 7-F | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-Cl | NSO₂Me | 4-OCF₃ | 7-Cl | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 7-CF₃ | NSO₂Me | 4-OCF₃ | 7-CF₃ | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |
| 4-CF₃ | 6-F | NSO₂Me | 4-OCF₃ | 6-F | NSO₂Me |

TABLE 32

| R¹ | R² | V | R¹ | R² | V |
|---|---|---|---|---|---|
| 4-CF₃ | 7-F | CO₂Me | 4-OCF₃ | 7-F | CO₂Me |
| 4-CF₃ | 7-F | CO₂Me | 4-OCF₃ | 7-F | CO₂Me |
| 4-CF₃ | 7-F | CO₂Me | 4-OCF₃ | 7-F | CO₂Me |
| 4-CF₃ | 7-Cl | CO₂Me | 4-OCF₃ | 7-Cl | CO₂Me |
| 4-CF₃ | 7-Cl | CO₂Me | 4-OCF₃ | 7-Cl | CO₂Me |
| 4-CF₃ | 7-Cl | CO₂Me | 4-OCF₃ | 7-Cl | CO₂Me |
| 4-CF₃ | 7-F | 4-F—Ph | 4-OCF₃ | 7-F | 4-F—Ph |
| 4-CF₃ | 7-F | 4-F—Ph | 4-OCF₃ | 7-F | 4-F—Ph |
| 4-CF₃ | 7-F | 4-F—Ph | 4-OCF₃ | 7-F | 4-F—Ph |
| 4-CF₃ | 7-Cl | 4-F—Ph | 4-OCF₃ | 7-Cl | 4-F—Ph |
| 4-CF₃ | 7-Cl | 4-F—Ph | 4-OCF₃ | 7-Cl | 4-F—Ph |
| 4-CF₃ | 7-Cl | 4-F—Ph | 4-OCF₃ | 7-Cl | 4-F—Ph |

TABLE 33

| R¹ | R² | R⁴ | R¹ | R² | R⁴ |
|---|---|---|---|---|---|
| 4-CF₃ | 5-F | Me | 4-OCF₃ | 5-F | Me |

TABLE 33-continued

| R¹ | R² | R⁴ | R¹ | R² | R⁴ |
|---|---|---|---|---|---|
| 4-CF₃ | 5-F | iPr | 4-OCF₃ | 5-F | iPr |
| 4-CF₃ | 5-F | Ph | 4-OCF₃ | 5-F | Ph |
| 4-CF₃ | 5-F | 4-F—Ph | 4-OCF₃ | 5-F | 4-F—Ph |
| 4-CF₃ | 5-F | 4-Cl—Ph | 4-OCF₃ | 5-f | 4-Cl—Ph |
| 4-CF₃ | 5-Cl | Me | 4-OCF₃ | 5-Cl | Me |
| 4-CF₃ | 5-Cl | iPr | 4-OCF₃ | 5-Cl | iPr |
| 4-CF₃ | 5-Cl | Ph | 4-OCF₃ | 5-Cl | Ph |
| 4-CF₃ | 5-Cl | 4-F—Ph | 4-OCF₃ | 5-Cl | 4-F—Ph |
| 4-CF₃ | 5-Cl | 4-Cl—Ph | 4-OCF₃ | 5-Cl | 4-Cl—Ph |
| 4-CF₃ | 5-CF₃ | Me | 4-OCF₃ | 5-CF₃ | Me |
| 4-CF₃ | 5-CF₃ | iPr | 4-OCF₃ | 5-CF₃ | iPr |
| 4-CF₃ | 5-CF₃ | Ph | 4-OCF₃ | 5-CF₃ | Ph |
| 4-CF₃ | 5-CF₃ | 4-F—Ph | 4-OCF₃ | 5-CF₃ | 4-F—Ph |
| 4-CF₃ | 5-CF₃ | 4-Cl—Ph | 4-OCF₃ | 5-CF₃ | 4-Cl—Ph |
| 4-CF₃ | 5-OCF₃ | Me | 4-OCF₃ | 5-OCF₃ | Me |
| 4-CF₃ | 5-OCF₃ | iPr | 4-OCF₃ | 5-OCF₃ | iPr |
| 4-CF₃ | 5-OCF₃ | Ph | 4-OCF₃ | 5-OCF₃ | Ph |
| 4-CF₃ | 5-OCF₃ | 4-F—Ph | 4-OCF₃ | 5-OCF₃ | 4-F—Ph |
| 4-CF₃ | 5-OCF₃ | 4-Cl—Ph | 4-OCF₃ | 5-OCF₃ | 4-Cl—Ph |
| 4-CF₃ | 4-F | Me | 4-OCF₃ | 4-F | Me |
| 4-CF₃ | 4-F | iPr | 4-OCF₃ | 4-F | iPr |
| 4-CF₃ | 4-F | Ph | 4-OCF₃ | 4-F | Ph |
| 4-CF₃ | 4-F | 4-F—Ph | 4-OCF₃ | 4-F | 4-F—Ph |
| 4-CF₃ | 4-F | 4-Cl—Ph | 4-OCF₃ | 4-F | 4-Cl—Ph |
| 4-CF₃ | 5-F | Me | 4-OCF₃ | 5-F | Me |
| 4-CF₃ | 5-F | iPr | 4-OCF₃ | 5-F | iPr |
| 4-CF₃ | 5-F | Ph | 4-OCF₃ | 5-F | Ph |
| 4-CF₃ | 5-F | 4-F—Ph | 4-OCF₃ | 5-F | 4-F—Ph |
| 4-CF₃ | 5-F | 4-Cl—Ph | 4-OCF₃ | 5-F | 4-Cl—Ph |
| 4-CF₃ | 5-Cl | Me | 4-OCF₃ | 5-Cl | Me |
| 4-CF₃ | 5-Cl | iPr | 4-OCF₃ | 5-Cl | iPr |
| 4-CF₃ | 5-Cl | Ph | 4-OCF₃ | 5-Cl | Ph |
| 4-CF₃ | 5-Cl | 4-F—Ph | 4-OCF₃ | 5-Cl | 4-F—Ph |
| 4-CF₃ | 5-Cl | 4-Cl—Ph | 4-OCF₃ | 5-Cl | 4-Cl—Ph |
| 4-CF₃ | 5-CF₃ | Me | 4-OCF₃ | 5-CF₃ | Me |
| 4-CF₃ | 5-CF₃ | iPr | 4-OCF₃ | 5-CF₃ | iPr |
| 4-CF₃ | 5-CF₃ | Ph | 4-OCF₃ | 5-CF₃ | Ph |
| 4-CF₃ | 5-CF₃ | 4-F—Ph | 4-OCF₃ | 5-CF₃ | 4-F—Ph |
| 4-CF₃ | 5-CF₃ | 4-Cl—Ph | 4-OCF₃ | 5-CF₃ | 4-Cl—Ph |
| 4-CF₃ | 5-OCF₃ | Me | 4-OCF₃ | 5-OCF₃ | Me |
| 4-CF₃ | 5-OCF₃ | iPr | 4-OCF₃ | 5-OCF₃ | iPr |
| 4-CF₃ | 5-OCF₃ | Ph | 4-OCF₃ | 5-OCF₃ | Ph |
| 4-CF₃ | 5-OCF₃ | 4-F—Ph | 4-OCF₃ | 5-OCF₃ | 4-F—Ph |
| 4-CF₃ | 5-OCF₃ | 4-Cl—Ph | 4-OCF₃ | 5-OCF₃ | 4-Cl—Ph |
| 4-CF₃ | 4-F | Me | 4-OCF₃ | 4-F | Me |
| 4-CF₃ | 4-F | iPr | 4-OCF₃ | 4-F | iPr |
| 4-CF₃ | 4-F | Ph | 4-OCF₃ | 4-F | Ph |
| 4-CF₃ | 4-F | 4-F—Ph | 4-OCF₃ | 4-F | 4-F—Ph |
| 4-CF₃ | 4-F | 4-Cl—Ph | 4-OCF₃ | 4-F | 4-Cl—Ph |
| 4-CF₃ | 5-F | Me | 4-OCF₃ | 5-F | Me |
| 4-CF₃ | 5-F | iPr | 4-OCF₃ | 5-F | iPr |
| 4-CF₃ | 5-F | Ph | 4-OCF₃ | 5-F | Ph |
| 4-CF₃ | 5-F | 4-F—Ph | 4-OCF₃ | 5-F | 4-F—Ph |
| 4-CF₃ | 5-F | 4-Cl—Ph | 4-OCF₃ | 5-F | 4-Cl—Ph |
| 4-CF₃ | 5-Cl | Me | 4-OCF₃ | 5-Cl | Me |
| 4-CF₃ | 5-Cl | iPr | 4-OCF₃ | 5-Cl | iPr |
| 4-CF₃ | 5-Cl | Ph | 4-OCF₃ | 5-Cl | Ph |
| 4-CF₃ | 5-Cl | 4-F—Ph | 4-OCF₃ | 5-Cl | 4-F—Ph |
| 4-CF₃ | 5-Cl | 4-Cl—Ph | 4-OCF₃ | 5-Cl | 4-Cl—Ph |
| 4-CF₃ | 5-CF₃ | Me | 4-OCF₃ | 5-CF₃ | Me |
| 4-CF₃ | 5-CF₃ | iPr | 4-OCF₃ | 5-CF₃ | iPr |
| 4-CF₃ | 5-CF₃ | Ph | 4-OCF₃ | 5-CF₃ | Ph |
| 4-CF₃ | 5-CF₃ | 4-F—Ph | 4-OCF₃ | 5-CF₃ | 4-F—Ph |
| 4-CF₃ | 5-CF₃ | 4-Cl—Ph | 4-OCF₃ | 5-CF₃ | 4-Cl—Ph |
| 4-CF₃ | 5-OCF₃ | Me | 4-OCF₃ | 5-OCF₃ | Me |
| 4-CF₃ | 5-OCF₃ | iPr | 4-OCF₃ | 5-OCF₃ | iPr |
| 4-CF₃ | 5-OCF₃ | Ph | 4-OCF₃ | 5-OCF₃ | Ph |
| 4-CF₃ | 5-OCF₃ | 4-F—Ph | 4-OCF₃ | 5-OCF₃ | 4-F—Ph |
| 4-CF₃ | 5-OCF₃ | 4-Cl—Ph | 4-OCF₃ | 5-OCF₃ | 4-Cl—Ph |
| 4-CF₃ | 4-F | Me | 4-OCF₃ | 4-F | Me |
| 4-CF₃ | 4-F | iPr | 4-OCF₃ | 4-F | iPr |
| 4-CF₃ | 4-F | Ph | 4-OCF₃ | 4-F | Ph |
| 4-CF₃ | 4-F | 4-F—Ph | 4-OCF₃ | 4-F | 4-F—Ph |
| 4-CF₃ | 4-F | 4-Cl—Ph | 4-OCF₃ | 4-F | 4-Cl—Ph |

TABLE 34

| R¹ | R² | R⁴ | R¹ | R² | R⁴ |
|---|---|---|---|---|---|
| 4-CF₃ | 5-F | Me | 4-OCF₃ | 5-F | Me |
| 4-CF₃ | 5-F | iPr | 4-OCF₃ | 5-F | iPr |
| 4-CF₃ | 5-F | Ph | 4-OCF₃ | 5-F | Ph |
| 4-CF₃ | 5-F | 4-F—Ph | 4-OCF₃ | 5-F | 4-F—Ph |
| 4-CF₃ | 5-F | 4-Cl—Ph | 4-OCF₃ | 5-f | 4-Cl—Ph |
| 4-CF₃ | 5-Cl | Me | 4-OCF₃ | 5-Cl | Me |
| 4-CF₃ | 5-Cl | iPr | 4-OCF₃ | 5-Cl | iPr |
| 4-CF₃ | 5-Cl | Ph | 4-OCF₃ | 5-Cl | Ph |
| 4-CF₃ | 5-Cl | 4-F—Ph | 4-OCF₃ | 5-Cl | 4-F—Ph |
| 4-CF₃ | 5-Cl | 4-Cl—Ph | 4-OCF₃ | 5-Cl | 4-Cl—Ph |
| 4-CF₃ | 5-CF₃ | Me | 4-OCF₃ | 5-CF₃ | Me |
| 4-CF₃ | 5-CF₃ | iPr | 4-OCF₃ | 5-CF₃ | iPr |
| 4-CF₃ | 5-CF₃ | Ph | 4-OCF₃ | 5-CF₃ | Ph |
| 4-CF₃ | 5-CF₃ | 4-F—Ph | 4-OCF₃ | 5-CF₃ | 4-F—Ph |
| 4-CF₃ | 5-CF₃ | 4-Cl—Ph | 4-OCF₃ | 5-CF₃ | 4-Cl—Ph |
| 4-CF₃ | 5-OCF₃ | Me | 4-OCF₃ | 5-OCF₃ | Me |
| 4-CF₃ | 5-OCF₃ | iPr | 4-OCF₃ | 5-OCF₃ | iPr |
| 4-CF₃ | 5-OCF₃ | Ph | 4-OCF₃ | 5-OCF₃ | Ph |
| 4-CF₃ | 5-OCF₃ | 4-F—Ph | 4-OCF₃ | 5-OCF₃ | 4-F—Ph |
| 4-CF₃ | 5-OCF₃ | 4-Cl—Ph | 4-OCF₃ | 5-OCF₃ | 4-Cl—Ph |
| 4-CF₃ | 4-F | Me | 4-OCF₃ | 4-F | Me |
| 4-CF₃ | 4-F | iPr | 4-OCF₃ | 4-F | iPr |
| 4-CF₃ | 4-F | Ph | 4-OCF₃ | 4-F | Ph |
| 4-CF₃ | 4-F | 4-F—Ph | 4-OCF₃ | 4-F | 4-F—Ph |
| 4-CF₃ | 4-F | 4-Cl—Ph | 4-OCF₃ | 4-F | 4-Cl—Ph |
| 4-CF₃ | 5-F | Me | 4-OCF₃ | 5-F | Me |
| 4-CF₃ | 5-F | iPr | 4-OCF₃ | 5-F | iPr |
| 4-CF₃ | 5-F | Ph | 4-OCF₃ | 5-F | Ph |
| 4-CF₃ | 5-F | 4-F—Ph | 4-OCF₃ | 5-F | 4-F—Ph |
| 4-CF₃ | 5-F | 4-Cl—Ph | 4-OCF₃ | 5-F | 4-Cl—Ph |
| 4-CF₃ | 5-Cl | Me | 4-OCF₃ | 5-Cl | Me |
| 4-CF₃ | 5-Cl | iPr | 4-OCF₃ | 5-Cl | iPr |
| 4-CF₃ | 5-Cl | Ph | 4-OCF₃ | 5-Cl | Ph |
| 4-CF₃ | 5-Cl | 4-F—Ph | 4-OCF₃ | 5-Cl | 4-F—Ph |
| 4-CF₃ | 5-Cl | 4-Cl—Ph | 4-OCF₃ | 5-Cl | 4-Cl—Ph |
| 4-CF₃ | 5-CF₃ | Me | 4-OCF₃ | 5-CF₃ | Me |
| 4-CF₃ | 5-CF₃ | iPr | 4-OCF₃ | 5-CF₃ | iPr |
| 4-CF₃ | 5-CF₃ | Ph | 4-OCF₃ | 5-CF₃ | Ph |
| 4-CF₃ | 5-CF₃ | 4-F—Ph | 4-OCF₃ | 5-CF₃ | 4-F—Ph |
| 4-CF₃ | 5-CF₃ | 4-Cl—Ph | 4-OCF₃ | 5-CF₃ | 4-Cl—Ph |
| 4-CF₃ | 5-OCF₃ | Me | 4-OCF₃ | 5-OCF₃ | Me |
| 4-CF₃ | 5-OCF₃ | iPr | 4-OCF₃ | 5-OCF₃ | iPr |
| 4-CF₃ | 5-OCF₃ | Ph | 4-OCF₃ | 5-OCF₃ | Ph |
| 4-CF₃ | 5-OCF₃ | 4-F—Ph | 4-OCF₃ | 5-OCF₃ | 4-F—Ph |
| 4-CF₃ | 5-OCF₃ | 4-Cl—Ph | 4-OCF₃ | 5-OCF₃ | 4-Cl—Ph |
| 4-CF₃ | 4-F | Me | 4-OCF₃ | 4-F | Me |
| 4-CF₃ | 4-F | iPr | 4-OCF₃ | 4-F | iPr |
| 4-CF₃ | 4-F | Ph | 4-OCF₃ | 4-F | Ph |
| 4-CF₃ | 4-F | 4-F—Ph | 4-OCF₃ | 4-F | 4-F—Ph |
| 4-CF₃ | 4-F | 4-Cl—Ph | 4-OCF₃ | 4-F | 4-Cl—Ph |
| 4-CF₃ | 5-F | Me | 4-OCF₃ | 5-F | Me |
| 4-CF₃ | 5-F | iPr | 4-OCF₃ | 5-F | iPr |
| 4-CF₃ | 5-F | Ph | 4-OCF₃ | 5-F | Ph |
| 4-CF₃ | 5-F | 4-F—Ph | 4-OCF₃ | 5-F | 4-F—Ph |
| 4-CF₃ | 5-F | 4-Cl—Ph | 4-OCF₃ | 5-F | 4-Cl—Ph |
| 4-CF₃ | 5-Cl | Me | 4-OCF₃ | 5-Cl | Me |
| 4-CF₃ | 5-Cl | iPr | 4-OCF₃ | 5-Cl | iPr |

TABLE 34-continued

| R¹ | R² | R⁴ | R¹ | R² | R⁴ |
|---|---|---|---|---|---|
| 4-CF₃ | 5-Cl | Ph | 4-OCF₃ | 5-Cl | Ph |
| 4-CF₃ | 5-Cl | 4-F—Ph | 4-OCF₃ | 5-Cl | 4-F—Ph |
| 4-CF₃ | 5-Cl | 4-Cl—Ph | 4-OCF₃ | 5-Cl | 4-Cl—Ph |
| 4-CF₃ | 5-CF₃ | Me | 4-OCF₃ | 5-CF₃ | Me |
| 4-CF₃ | 5-CF₃ | iPr | 4-OCF₃ | 5-CF₃ | iPr |
| 4-CF₃ | 5-CF₃ | Ph | 4-OCF₃ | 5-CF₃ | Ph |
| 4-CF₃ | 5-CF₃ | 4-F—Ph | 4-OCF₃ | 5-CF₃ | 4-F—Ph |
| 4-CF₃ | 5-CF₃ | 4-Cl—Ph | 4-OCF₃ | 5-CF₃ | 4-Cl—Ph |
| 4-CF₃ | 5-OCF₃ | Me | 4-OCF₃ | 5-OCF₃ | Me |
| 4-CF₃ | 5-OCF₃ | iPr | 4-OCF₃ | 5-OCF₃ | iPr |
| 4-CF₃ | 5-OCF₃ | Ph | 4-OCF₃ | 5-OCF₃ | Ph |
| 4-CF₃ | 5-OCF₃ | 4-F—Ph | 4-OCF₃ | 5-OCF₃ | 4-F—Ph |
| 4-CF₃ | 5-OCF₃ | 4-Cl—Ph | 4-OCF₃ | 5-OCF₃ | 4-Cl—Ph |
| 4-CF₃ | 4-F | Me | 4-OCF₃ | 4-F | Me |
| 4-CF₃ | 4-F | iPr | 4-OCF₃ | 4-F | iPr |
| 4-CF₃ | 4-F | Ph | 4-OCF₃ | 4-F | Ph |
| 4-CF₃ | 4-F | 4-F—Ph | 4-OCF₃ | 4-F | 4-F—Ph |
| 4-CF₃ | 4-F | 4-Cl—Ph | 4-OCF₃ | 4-F | 4-Cl—Ph |
| 4-CF₃ | 5-F | Me | 4-OCF₃ | 5-F | Me |
| 4-CF₃ | 5-F | iPr | 4-OCF₃ | 5-F | iPr |
| 4-CF₃ | 5-F | Ph | 4-OCF₃ | 5-F | Ph |
| 4-CF₃ | 5-F | 4-F—Ph | 4-OCF₃ | 5-F | 4-F—Ph |
| 4-CF₃ | 5-F | 4-Cl—Ph | 4-OCF₃ | 5-F | 4-Cl—Ph |
| 4-CF₃ | 5-Cl | Me | 4-OCF₃ | 5-Cl | Me |
| 4-CF₃ | 5-Cl | iPr | 4-OCF₃ | 5-Cl | iPr |
| 4-CF₃ | 5-Cl | Ph | 4-OCF₃ | 5-Cl | Ph |
| 4-CF₃ | 5-Cl | 4-F—Ph | 4-OCF₃ | 5-Cl | 4-F—Ph |
| 4-CF₃ | 5-Cl | 4-Cl—Ph | 4-OCF₃ | 5-Cl | 4-Cl—Ph |
| 4-CF₃ | 5-CF₃ | Me | 4-OCF₃ | 5-CF₃ | Me |
| 4-CF₃ | 5-CF₃ | iPr | 4-OCF₃ | 5-CF₃ | iPr |
| 4-CF₃ | 5-CF₃ | Ph | 4-OCF₃ | 5-CF₃ | Ph |
| 4-CF₃ | 5-CF₃ | 4-F—Ph | 4-OCF₃ | 5-CF₃ | 4-F—Ph |
| 4-CF₃ | 5-CF₃ | 4-Cl—Ph | 4-OCF₃ | 5-CF₃ | 4-Cl—Ph |
| 4-CF₃ | 5-OCF₃ | Me | 4-OCF₃ | 5-OCF₃ | Me |
| 4-CF₃ | 5-OCF₃ | iPr | 4-OCF₃ | 5-OCF₃ | iPr |
| 4-CF₃ | 5-OCF₃ | Ph | 4-OCF₃ | 5-OCF₃ | Ph |
| 4-CF₃ | 5-OCF₃ | 4-F—Ph | 4-OCF₃ | 5-OCF₃ | 4-F—Ph |
| 4-CF₃ | 5-OCF₃ | 4-Cl—Ph | 4-OCF₃ | 5-OCF₃ | 4-Cl—Ph |
| 4-CF₃ | 4-F | Me | 4-OCF₃ | 4-F | Me |
| 4-CF₃ | 4-F | iPr | 4-OCF₃ | 4-F | iPr |
| 4-CF₃ | 4-F | Ph | 4-OCF₃ | 4-F | Ph |
| 4-CF₃ | 4-F | 4-F—Ph | 4-OCF₃ | 4-F | 4-F—Ph |
| 4-CF₃ | 4-F | 4-Cl—Ph | 4-OCF₃ | 4-F | 4-Cl—Ph |

TABLE 35

| R¹ | R² | R³ | R⁵ | R¹ | R² | R³ | R⁵ |
|---|---|---|---|---|---|---|---|
| 4-CF₃ | 4-Cl | CO₂Me | H | 4-OCF₃ | 4-Cl | 4-Cl—Ph | H |
| 4-CF₃ | 4-Cl | CO₂Me | H | 4-CF₃ | 4-Cl | CO₂Me | Me |
| 4-CF₃ | 4-Cl | CO₂Me | H | 4-CF₃ | 4-Cl | CO₂Me | Me |
| 4-CF₃ | 4-Cl | CO₂Me | H | 4-CF₃ | 4-Cl | CO₂Me | Me |
| 4-CF₃ | 4-CF₃ | CO₂Me | H | 4-CF₃ | 4-Cl | CO₂Me | Me |
| 4-CF₃ | 4-CF₃ | CO₂Me | H | 4-CF₃ | 4-CF₃ | CO₂Me | Me |
| 4-CF₃ | 4-CF₃ | CO₂Me | H | 4-CF₃ | 4-CF₃ | CO₂Me | Me |
| 4-CF₃ | 4-Cl | 4-Cl—Ph | H | 4-CF₃ | 4-CF₃ | CO₂Me | Me |
| 4-CF₃ | 4-Cl | 4-Cl—Ph | H | 4-OCF₃ | 4-Cl | CO₂Me | Me |
| 4-CF₃ | 4-Cl | 4-Cl—Ph | H | 4-OCF₃ | 4-Cl | CO₂Me | Me |
| 4-CF₃ | 4-CF₃ | 4-Cl—Ph | H | 4-OCF₃ | 4-Cl | CO₂Me | Me |
| 4-CF₃ | 4-CF₃ | 4-Cl—Ph | H | 4-OCF₃ | 4-CF₃ | CO₂Me | Me |
| 4-CF₃ | 4-CF₃ | 4-Cl—Ph | H | 4-OCF₃ | 4-CF₃ | CO₂Me | Me |
| 4-OCF₃ | 4-Cl | CO₂Me | H | 4-OCF₃ | 4-CF₃ | CO₂Me | Me |
| 4-OCF₃ | 4-Cl | CO₂Me | H | | | | |
| 4-OCF₃ | 4-Cl | CO₂Me | H | | | | |
| 4-OCF₃ | 4-Cl | CO₂Me | H | | | | |
| 4-OCF₃ | 4-CF₃ | CO₂Me | H | | | | |
| 4-OCF₃ | 4-CF₃ | CO₂Me | H | | | | |
| 4-OCF₃ | 4-CF₃ | CO₂Me | H | | | | |
| 4-OCF₃ | 4-Cl | 4-Cl—Ph | H | | | | |
| 4-OCF₃ | 4-Cl | 4-Cl—Ph | H | | | | |
| 4-OCF₃ | 4-Cl | 4-Cl—Ph | H | | | | |

TABLE 36

| R¹ | R² | R³ | R⁵ | R¹ | R² | R³ | R⁵ |
|---|---|---|---|---|---|---|---|
| 4-CF₃ | 4-Cl | CO₂Me | H | 4-OCF₃ | 4-CF₃ | 4-F—Ph | H |
| 4-CF₃ | 4-Cl | CO₂Me | H | 4-CF₃ | 4-Cl | CO₂Me | Me |
| 4-CF₃ | 4-Cl | CO₂Me | H | 4-CF₃ | 4-Cl | CO₂Me | Me |
| 4-CF₃ | 4-Cl | CO₂Me | H | 4-CF₃ | 4-Cl | CO₂Me | Me |
| 4-CF₃ | 4-CF₃ | CO₂Me | H | 4-CF₃ | 4-Cl | CO₂Me | Me |
| 4-CF₃ | 4-CF₃ | CO₂Me | H | 4-CF₃ | 4-CF₃ | CO₂Me | Me |
| 4-CF₃ | 4-CF₃ | CO₂Me | H | 4-CF₃ | 4-CF₃ | CO₂Me | Me |
| 4-CF₃ | 4-Cl | 4-F—Ph | H | 4-CF₃ | 4-CF₃ | CO₂Me | Me |
| 4-CF₃ | 4-Cl | 4-F—Ph | H | 4-OCF₃ | 4-Cl | CO₂Me | Me |
| 4-CF₃ | 4-Cl | 4-F—Ph | H | 4-OCF₃ | 4-Cl | CO₂Me | Me |
| 4-CF₃ | 4-CF₃ | 4-F—Ph | H | 4-OCF₃ | 4-Cl | CO₂Me | Me |
| 4-CF₃ | 4-CF₃ | 4-F—Ph | H | 4-OCF₃ | 4-CF₃ | CO₂Me | Me |
| 4-CF₃ | 4-CF₃ | 4-F—Ph | H | 4-OCF₃ | 4-CF₃ | CO₂Me | Me |
| 4-OCF₃ | 4-Cl | CO₂Me | H | 4-OCF₃ | 4-CF₃ | CO₂Me | Me |
| 4-OCF₃ | 4-Cl | CO₂Me | H | | | | |
| 4-OCF₃ | 4-Cl | CO₂Me | H | | | | |
| 4-OCF₃ | 4-Cl | CO₂Me | H | | | | |
| 4-OCF₃ | 4-CF₃ | CO₂Me | H | | | | |
| 4-OCF₃ | 4-CF₃ | CO₂Me | H | | | | |

TABLE 36-continued

| $R^1$ | $R^2$ | $R^3$ | $R^5$ | $R^1$ | $R^2$ | $R^3$ | $R^5$ |
|---|---|---|---|---|---|---|---|
| 4-OCF$_3$ | 4-CF$_3$ | CO$_2$Me | H | | | | |
| 4-OCF$_3$ | 4-CF$_3$ | CO$_2$Me | H | | | | |
| 4-OCF$_3$ | 4-Cl | 4-F—Ph | H | | | | |
| 4-OCF$_3$ | 4-Cl | 4-F—Ph | H | | | | |
| 4-OCF$_3$ | 4-Cl | 4-F—Ph | H | | | | |
| 4-OCF$_3$ | 4-Cl | 4-F—Ph | H | | | | |
| 4-OCF$_3$ | 4-CF$_3$ | 4-F—Ph | H | | | | |
| 4-OCF$_3$ | 4-CF$_3$ | 4-F—Ph | H | | | | |
| 4-OCF$_3$ | 4-CF$_3$ | 4-F—Ph | H | | | | |

Formulation and Use

The compounds of this invention will generally be used in formulation with an agriculturally suitable carrier comprising a liquid or solid diluent or an organic solvent. Useful formulations of the compounds of Formula I can be prepared in conventional ways. They include dusts, granules, baits, pellets, solutions, suspensions, emulsions, wettable powders, emulsifiable concentrates, dry flowables and the like. Many of these can be applied directly. Sprayable formualtions can be extended in suitable media and used at spray volumes of from about one to several hundred liters per hectare. High strength compositions are primarily used as intermediates for further formulation. The formulations, broadly, contain from less than about 1% to 99% by weight of active ingredient(s) and at least one of a) about 0.1% to 20% surfactant(s) and b) about 5% to 99% solid or liquid diluent(s). More specifically, they will contain effective amounts of these ingredients in the following approximate proportions:

| | Percent by Weight | | |
|---|---|---|---|
| | Active Ingredient | Diluent(s) | Surfactant(s) |
| Wettable Powders | 25–90 | 0–74 | 1–10 |
| Oil Suspensions, Emulsions, Solutions (including Emulsifiable Concentrates) | 5–50 | 40–95 | 0–15 |
| Dusts | 1–25 | 70–99 | 0–5 |
| Granules, Baits and Pellets | 0.01–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques. See J. E. Browning, "Agglomeration", Chemical Engineering, Dec. 4, 1967, pages 147 and following, and "Perry's Chemical Engineer's Handbook", 4th Ed., McGraw-Hill, New York, 1963, pages 8 to 59 and following.

EXAMPLE A

| Emulsifiable Concentrate | |
|---|---|
| 7-chloro-2,3,3a,4-tetrahydro-3a-(1-methylethyl)-N-[4-(trifluoromethyl)phenyl][1]benzopyrano[4,3-c]-pyrazole-2-carboximidoyl chloride | 20% |
| blend of oil soluble sulfonates and polyoxyethylene ethers | 10% |
| isophorone | 70% |

The ingredients are combined and stirred with gentle warming to speed solution. A fine screen filter is included in packaging operation to insure the absence of any extraneous undissolved material in the product.

EXAMPLE B

| Wettable Powder | |
|---|---|
| N-(4-chlorophenyl)-4,5-dihydro-α-(methylthio)-4-phenyl-3-[4-(trifluoromethyl)phenyl]-1H-pyrazole-1-methanimine | 30% |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammermill, the material is re-blended and sifted through a 50 mesh screen.

EXAMPLE C

| Dust | |
|---|---|
| Wettable powder of Example B | 10% |
| pyrophyllite (powder) | 90% |

The wettable powder and the pyrophyllite diluent are thoroughly blended and then packaged. The product is suitable for use as a dust.

EXAMPLE D

| Granule | |
|---|---|
| 1-(4-chlorophenyl)-5-(4-fluorophenyl)-4,5-dihydro-N-[4-(trifluoromethyl)phenyl]-1H-pyrazole-3-carboximidoyl chloride | 10% |
| attapulgite granules (low volative matter, 0.71/0.30 mm; U.S.S. No. 25–50 sieves) | 90% |

The active ingredient is dissolved in a volatile solvent such as acetone and sprayed upon dedusted and prewarmed attapulgite granules in a double cone blender. The acetone is then driven off by heating. The granules are then allowed to cool and are packaged.

EXAMPLE E

| Granule | |
|---|---|
| Wettable powder of Example B | 15% |
| gypsum | 69% |
| potassium sulfate | 16% |

The ingredients are blended in a rotating mixer and water sprayed on to accomplish granulation. When most of the material has reached the desired range of 0.1 to 0.42 mm (U.S. Ser. No. 18 to 40 sieves), the granules are removed, dried, and screened. Oversize material is crushed to produce additional material in the desired range. These granules contain 4.5% active ingredient.

EXAMPLE F

| Solution | |
|---|---|
| 7-chloro-2,3,3a,4-tetrahydro-3a-(1-methylethyl)-N-[4-(trifluoromethyl)phenyl][1]benzopyrano[4,3-c]-pyrazole-2-carboximidoyl chloride | 25% |
| N-methyl-pyrrolidone | 75% |

The ingredients are combined and stirred to produce a solution suitable for direct, low volume application.

EXAMPLE G

| Aqueous Suspension | |
|---|---|
| N-(4-chlorophenyl)-4,5-dihydro-α-(methylthio)-4-phenyl-3-[4-(trifluoromethyl)phenyl]-1H-pyrazole-1-methanimine | 40% |
| polyacrylic acid thickener | 0.3% |
| dodecyclophenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles substantially all under 5 microns in size.

EXAMPLE H

| Oil Suspension | |
|---|---|
| 1-(4-chlorophenyl)-5-(4-fluorophenyl)-4,5-dihydro-N-[4-(trifluoromethyl)phenyl]-1H-pyrazole-3-carboximidoyl chloride | 35.0% |
| blend of polyalcohol carboxylic esters and oil soluble petroleum sulfonates | 6.0% |
| xylene range solvent | 59.0% |

The ingredients are combined and ground together in a sand mill to produce particles substantially all below 5 microns. The product can be used directly, extended with oils, or emulsified in water.

EXAMPLE I

| Bait Granules | |
|---|---|
| 1-(4-chlorophenyl)-5-(4-fluorophenyl)-4,5-dihydro-N-[4-(trifluoromethyl)phenyl]-1H-pyrazole-3-carboximidoyl chloride | 3.0% |
| blend of polyethoxylated nonylphenols and sodium dodecylbenzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged.

Compounds of Formula I can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of this invention can be formulated are:

Insecticides:
3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl O-(methylcarbamoyl)thioacetohydroxamate (methomyl)
N'-(4-chloro-o-tolyl)-N,N-dimethylformamidine (chlordimeform)
O,O-diethyl-O-(2-isopropyl-4-methyl-6-pyrimidylphosphorothioate (diazinon)
octachlorocamphene (toxaphene)
O-ethyl-O-p-nitrophenyl phenylphosphonothioate (EPN)
(S)-α-cyano-m-phenoxybenzyl(1R,3R)-3-(2,2-dibromovinyl)-2,2-dimethylcyclopropanecarboxylate (deltamethrin)
Methyl-N',N'-dimethyl-N-[(methylcarbamoyl)oxy]-1-thioox amimidate (oxamyl)
cyano(3-phenoxyphenyl)-methyl-4-chloro-a-(1-methylethyl)benzeneacetate (fenvalerate)
(3-phenoxyphenyl)methyl(+)-cis,trans-3-(2,2-dichloroethenyl)-2,2-dimethylcyclopropanecarboxylate (permethrin)
α-cyano-3-phenoxybenzyl 3-(2,2-dichlorovinyl)-2,2-dimethylcyclopropane carboxylate (cypermethrin)

O-ethyl-S-(p-chlorophenyl)ethylphosphonodithioate (profenofos)
phosphorothiolothionic acid,
O-ethyl-O-[4-(methylthio)-phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenphos, methidathion, methamidiphos, monocrotphos, phosmet, phosphamidon, phosalone, pirimicarb, phorate, profenofos, terbufos, trichlorfon, methoxychlor, bifenthrin, biphenate, cyfluthrin, fenpropathrin, fluvalinate, flucythrinate, tralomethrin, metaldehyde and rotenone.

Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2-ylmethyl]-1H-1,2,4-triazole (propiconazole)
2-cyano-N-ethylcarbamoyl-2-methoxyiminoacetamide (cymoxanil)
1-(4-chlorophenoxy)-3,3-dimethyl-1-(1H-1,2,4-triazol-1-yl)-2-butanone (triadimefon)
N-(trichloromethylthio)tetrahydrophthalimide (captan)
N-(trichloromethylthio)phthalimide (folpet)
1-[[[bis(4-fluorophenyl)][methyl]silyl]methyl]-1H-1,2,4-triazole.

Nematocides:
S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid, O-ethyl O'-[4-(methylthio)-m-tolyl]diester (fenamiphos)

Bactericides:
tribasic copper sulfate
streptomycin sulfate

Acaricides:
senecionic acid, ester with 2-sec-butyl-4,6-dinitrophenol (binapacryl)
6-methyl-1,3-cithiolo[4,5-$\beta$]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide Biological
*Bacillus thuringiensis*
*Avermectin B.*

Utility

The compounds of this invention exhibit activity against a wide spectrum of foliar and soil inhabiting arthropods which are pests of growing and stored agronomic crops, forestry, greenhouse crops, ornamentals, nursery crops, stored food and fiber products, livestock, household, and public and animal health. Those skilled in the art will recognize that not all compounds are equally effective against all pests but the compounds of this invention display activity against economically important agronomic, forestry, greenhouse, ornamental food and fiber product, stored product, domestic structure, and nursery pests, such as:

larvae of the order Lepidotera including fall and beet armyworm and other Spodoptera spp., tobacco budworm, corn earworm and other Heliothis spp., European corn borer, navel orangeworm, stalk/stem borers and other pyralids, cabbage and soybean loopers and other loopers, codling moth, grape berry moth and other tortricids, black cutworm, spotted cutworm, other cutworms and other noctuids, diamondback moth, green cloverworm, velvetbean caterpillar, green cloverworm, pink bollworm, gypsy moth, and spruce budworm;

foliar feeding larvae and adults of the order Coleoptera including Colorado potato beetle, Mexican bean beetle, flea beetle, Japanese beetles, and other leaf beetles, boll weevil, rice water weevil, granary weevil, rice weevil and other weevil pests, and soil inhabiting insects such as Western corn rootworm and other Diabrotica spp., Japanese beetle, European chafer and other coleopteran grubs, and wireworms;

adults and larvae of the orders Hemiptera and Homoptera including tarnished plant bug and other plant bugs (miridae), aster leafhopper and other leafhoppers (cicadellidae), rice planthopper, brown planthopper, and other planthoppers (fulgoroidea), psylids, whiteflies (aleurodidae), aphids (aphidae), scales (coccidae and diaspididae), lace bugs (tingidae), stink bugs (pentatomidae), cinch bugs and other seed bugs (lygaeidae), cicadas (cicadidae), spittlebugs (cercopids), squash bugs (coreidae), red bugs and cotton stainers (pyrrhocoridae);

adults and larvae of the order acari (mites) including European red mite, two spotted spider mite, rust mites, McDaniel mite, and foliar feeding mites;

adults and immatures of the order Orthoptera including grasshoppers;

adults and immatures of the order Diptera including leafminers, midges, fruit flies (tephritidae), and soil maggots;

adults and immatures of the order Thysanoptera including onion thrips and other foliar feeding thrips.

The compounds are also active against economically important livestock, household, public and animal health pests such as:

insect pests of the order Hymenoptera including carpenter ants, bees, hornets, and wasps;

insect pests of the order Diptera including house flies, stable flies, face flies, horn flies, blow flies, and other muscoid fly pests, horse flies, deer flies and other Brachycera, mosquitoes, black flies, biting midges, sand flies, sciarids, and other Nematocera;

insect pests of the order Orthoptera including cockroaches and crickets;

insect pests of the order Isoptera including the Eastern subterranean termite and other termites;

insect pests of the order Mallophaga and Anoplura including the head louse, body louse, chicken head louse and other sucking and chewing parasitic lice that attack man and animals;

insect pests of the order Siphonoptera including the cat flea, dog flea and other fleas.

The specific species for which control is exemplified are: fall armyworm, *Spodoptera fruigiperda*; tobacco budworm, *Heliothis virescens*; boll weevil, *Anthonomus grandis*; aster leafhopper, *Macrosteles fascifrons*; black bean aphid, (*Aphis Fabae*); southern corn rootworm, *Diabrotica undecimpunctata*. The pest control protection afforded by the compounds of the present invention is not limited, however, to these species. The compounds of this invention may also be utilized as rodenticides.

Application

Arthropod pests are controlled and protection of agronomic crops, animal and human health is achieved by applying one or more of the Formula I compounds of this invention, in an effective amount, to the environment of the pests including the agronomic and/or nonagronomic locus of infestation, to the area to be protected, or directly on the pests to be controlled. Because of the diversity of habitat and behavior of these arthropod pest species, many different methods of application are employed. A preferred method of application is by spraying with equipment that distributes the compound in the environment of the pests, on the foliage, animal, person, or premise, in the soil or animal, to the plant part that is infested or needs to be protected. Alternatively, granular formulations of these toxicant compounds can be applied to or incorporated into the soil. Other methods of application can also be employed including direct and residual sprays, aerial sprays, baits, eartags, boluses, foggers, aerosols, and many others. The compounds can be incorporated into baits that are consumed by the arthropods or in devices such as traps and the like which entice them to ingest or otherwise contact the compounds.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, and synergists such as piperonyl butoxide often enhance the efficacy of the compounds of Formula I.

The rate of application of the Formula I compounds required for effective control will depend on such factors as the species of arthropod to be controlled, the pest's life cycle, life stage, its size, location, time of year, host crop or animal, feeding behavior, mating behavior, ambient moisture, temperature, etc. In general, application rates of 0.01 to 2 kg of active ingredient per hectare are sufficient to provide large-scale effective control of pests in agronomic ecosystems under normal circumstances, but as little as 0.001 kg/hectare or as much as 8 kg hectare may be required. For nonagronomic applications, effective use rates will range from about 1.0 to 50 mg/square meter but as much as 150 mg/square meter may be required.

The following Examples demonstrate the control efficacy of compounds of Formula I on specific pests; see Index Table A for compound descriptions.

INDEX TABLE A

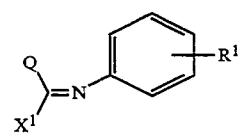

| CMPD | Q | $X^1$ | V | $Y^1$ | $R^1$ | $R^2$ | $R^3$ | $R^4$ | $R^5$ | mp(°C.) |
|---|---|---|---|---|---|---|---|---|---|---|
| 1 | 4 | Cl | — | — | 4-$CF_3$ | 4-Cl | $CO_2Me$ | — | H | 115–118 |
| 2 | 5 | Cl | — | — | 4-$CF_3$ | 4-Cl | 4-F—Ph | — | H | 154–156 |
| 3 | 1 | Cl | O | — | 4-$CF_3$ | 7-Cl | iPr | — | — | 148–149 |
| 4 | 1 | Cl | O | — | 4-$CF_3$ | 7-$CF_3$ | $CO_2Me$ | — | — | 150–152 |
| 5 | 1 | Cl | O | — | 4-$CF_3$ | 6-F | 4-F—Ph | — | — | 184–186 |
| 6 | 4 | SMe | — | — | 4-Cl | 4-$CF_3$ | Ph | — | H | oil |
| 7 | 1 | SMe | O | — | 4-$CF_3$ | 7-$CF_3$ | H | — | — | oil |
| 8 | 3 | SMe | $CH_2$ | H | 4-$CF_3$ | 5-F | — | Ph | H | 135–137 |
| 9 | 3 | $SCH_2Ph$ | $CH_2$ | H | 4-$CF_3$ | 5-F | — | Ph | H | oil |
| 10 | 1 | $OCO_2Me$ | O | — | 4-$CF_3$ | 7-$CF_3$ | $CO_2Me$ | — | — | 112–114 |

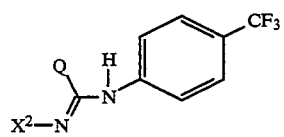

| CMPD | Q | $X^2$ | $R^2$ | $R^3$ | $R^4$ | $R^5$ | mp(°C.) |
|---|---|---|---|---|---|---|---|
| 11 | 5 | OH | 4-Cl | 4-F—Ph | — | H | 188–191 |
| 12 | 5 | OCONHMe | 4-Cl | 4-F—Ph | — | H | 75–77 |

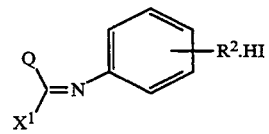

| CMPD | Q | $X^1$ | $R^1$ | $R^2$ | $R^3$ | $R^4$ | $R^5$ | (mp°C.) |
|---|---|---|---|---|---|---|---|---|

-continued

| 13 | 4 | SMe | 4-Cl | 4-CF$_3$ | Ph | — | H | 194–195 |

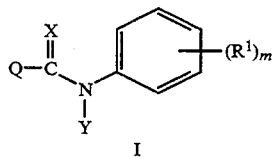

I

| CMPD | Q | R$^3$ | V | A | X | Y | R$^1$ | R$^2$ | R | mp(°C.) |
|---|---|---|---|---|---|---|---|---|---|---|
| 14 | 6 | CO$_2$Me | O | — | O | H | 4-CF$_3$ | H | H | 211–212 |
| 15 | 6 | CO$_2$Me | O | — | O | H | 4-CF$_3$ | H | CONHMe | 208–209 |
| 16 | 6 | 4-F—Ph | O | — | O | H | 4-CF$_3$ | H | H | 155–158 |
| 17 | 9 | 4-Cl—Ph | — | — | O | H | 4-CF$_3$ | 4-Cl | H | 242–243 |
| 18 | 6 | Ph | O | — | O | H | 4-CF$_3$ | H | H | 197–203 |
| 19 | 8 | 4-F—Ph | — | CH$_2$ | O | H | 4-CF$_3$ | 5-F | H | 167–170 |
| 20 | 10 | 4-F—Ph | — | — | O | H | 4-CF$_3$ | Cl | H | 50–55 |

EXAMPLE J

Fall Armyworm

Test units, each consisting of an 8-ounce (230 mL) plastic cup containing a layer of wheat germ diet, approximately 0.5 cm thick, were prepared. Ten third-instar larvae of fall armyworm (*Spodoptera frugiperda*) were placed into each cup. Solutions of each of the test compounds (acetone/distilled water 75/25 solvent) were sprayed onto the cups, a single solution per set of three cups. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i (207 kPa). The cups were then covered and held at 27° C. and 50% relative humidity for 72 hours, after which time readings were taken. Of the compounds tested, the following resulted in greater than or equal to 80% mortality: 1, 2, 6, 9, 10, 11, 12, 13, 14, 16 and 17.

EXAMPLE K

Tobacco Budworm

The test procedure of Example J was repeated for efficacy against third-instar larvae of the tobacco budworm (*Heliothis virescens*) except that mortality was assessed at 48 hours. Of the compounds tested, the following resulted in greater than or equal to 80% mortality: 2, 9, 10, 11, 14, 15 and 16.

EXAMPLE L

Southern Corn Rootworm

Test units, each consisting of an 8-ounce (230 mL) plastic cup containing 1 sprouted corn seed, were prepared. Sets of three test units were sprayed as described in Example J with individual solutions of the test compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken. Of the compounds tested, the following resulted in greater than or equal to 80% mortality: 2, 8, 10, 11, 13, 14, 15, 17 and 18.

EXAMPLE M

Aster Leafhopper

Test units were prepared from a series of 12-ounce (345 mL) cups, each containing oat (*Avena sativa*) seedlings in a 2.54 cm layer of sterilized soil. The test units were sprayed as described in Example J with individual solutions of the below-listed compounds. After the oats had dried from the spraying, between 10 and 15 adult aster leafhoppers (*Mascrosteles fascifrons*) were aspirated into each of the covered cups. The cups were held at 27° C. and 50% relative humidity for 48 hours, after which time mortality readings were taken. Of the compounds tested, the following resulted in greater than or equal to 80% mortality: 1, 10, 14, 15 and 16.

EXAMPLE N

Black Bean Aphid

Test units were prepared, each consisting of a single nasturtium (Tropaeolum sp.) leaf infested with 5 to 10 black bean aphids (*Aphis fabae*). Each leaf was cut and individually held in a 1-dram glass vial filled with a 10% sugar solution prior to and after spraying. During spraying, the infested leaves were inverted to expose the aphids, and each leaf was held in place by a clip. Three test units with leaves were sprayed with individual solutions of the below-listed compounds following the spray procedure of Example J. Sprayed leaves were returned to the individual glass vials, covered with a clear plastic 1-ounce (29 mL) cup and were held at 27° C. and 50% relative humidity for 48 hours, after which time mortality readings were taken. None of the compounds that were tested exhibited mortality of 80% or greater.

EXAMPLE 0

Boll Weevil

Five adult boll weevils (*Anthonomus grandis*) were placed into each of a series of 9-ounce (260 mL) cups. The test procedure employed was then otherwise the same as in Example J. Mortality readings were taken 48 hours after treatment. Of the compounds tested, the following resulted in greater than or equal to 80% mortality: 3, 4, 6, 7, 8, 10, 13, 14, 15, 16 and 18.

EXAMPLE P

Two-Spotted Spider Mite

Test units, each consisting of 2.54 cm$^2$ sections of kidney bean leaves, were infested with 20 to 30 adult two-spotted spider mites (*Tetranychus urticae*) and sprayed as described in Example J with individual solutions of the below-listed compounds. Three test units were sprayed per solution. Sprayed leaf sections were then placed on a layer of moistened cotton in a Petri dish and held at 27° C. and 50% relative humidity for 48 hours, after which time mortality readings were taken. None of the compounds that were tested exhibited mortality of 80% or greater.

What is claimed is:

1. A compound of the formula

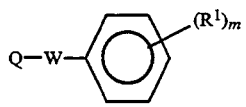

wherein:

Q is attached to the carbon terminus of W and is selected from the group

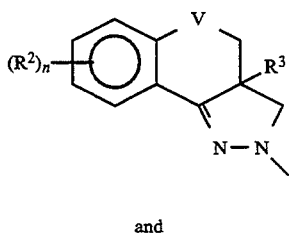

and

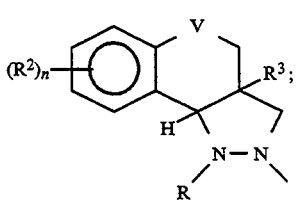

W is selected from the group

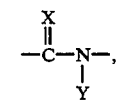

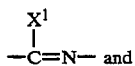

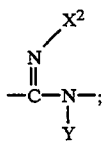

wherein:

V is O;

X is selected from the group O and S;

$X^1$ is selected from the group Cl, Br, $OR^6$, $SR^6$, and $NR^6R^7$;

$X^2$ is selected from the group $R^6$, OH, $OR^6$, CN, $SO_2R^6$, $OC(O)NR^7R^8$, $OC(O)OCH_3$, $NR^7R^8$, phenyl optionally substituted with $R^9$ and $SO_2Ph$ optionally substituted with $R^9$;

Y is selected from the group H, $C_1$-$C_6$ alkyl, benzyl, $C_2$-$C_6$ alkoxyalkyl, CHO, $C_2$-$C_6$ alkylcarbonyl, $C_2$-$C_6$ alkoxycarbonyl, $C_2$-$C_6$ haloalkylcarbonyl, $C_1$-$C_6$ alkylthio, $C_1$-$C_6$ haloalkylthio, phenylthio, $R^{17}OC(O)N(R)^{18}S$ and $SN(R^{19})R^{20}$;

R is selected from the group H, $C_1$-$C_4$ alkyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl, $C_2$-$C_4$ haloalkoxycarbonyl, $C_2$-$C_5$ alkylcarbamoyl, $C_3$-$C_6$ cycloalkyl, $C_3$-$C_6$ halocycloalkyl, $C_4$-$C_7$ alkylcycloalkyl, $C_4$-$C_7$ haloalkylcycloalkyl, $C_1$-$C_4$ alkylsulfonyl, $C_1$-$C_4$ haloalkylsulfonyl and $SO_2Ph$;

$R^1$, $R^2$, $R^9$, $R^{10}$, $R^{14}$ are each independently selected from the group H, halogen, CN, $C_1$-$C_3$ haloalkyl, $C_1$-$C_3$ haloalkoxy and $OS(O)_2C_1$-$C_3$ haloalkyl;

$R^3$ is selected from the group H, $C_1$-$C_6$ alkyl, $C_2$-$C_6$ alkenyl, $CO_2R^{13}$ and phenyl optionally substituted by $(R^{14})_p$;

$R^5$ is selected from the group H and $C_1$-$C_4$ alkyl;

$R^6$ is selected from the group $C_1$-$C_3$ alkyl, benzyl optionally substituted with $R^9$, $C_2$-$C_4$ alkenyl, $C_2$-$C_4$ alkynyl, $C_1$-$C_3$ haloalkyl, $C_2$-$C_4$ haloalkenyl, $C_2$-$C_3$ alkoxycarbonyl, $C_3$-$C_6$ cycloalkyl and $C_2$-$C_3$ alkylcarbonyl; or $R^6$ is $C_1$-$C_3$ alkyl substituted with a member selected from the group $OCH_3$, $OCH_2CH_3$, $NO_2$, CN, $CO_2CH_3$, $CO_2CH_2CH_3$, $SCH_3$ and $SCH_2CH_3$;

$R^7$ is selected from the group H, $C_1$-$C_4$ alkyl, $C_1$-$C_4$ haloalkyl, $C_2$-$C_4$ alkoxycarbonyl, phenyl optionally substituted with $R^{10}$ and pyridyl optionally substituted with $R^{10}$; or $R^6$ and $R^7$ are taken together as $CH_2CH_2CH_2CH_2$, $CH_2CH_2CH_2CH_2CH_2$, or $CH_2CH_2OCH_2CH_2$ when $X^1$ is $NR^6R^7$;

$R^8$ is selected from the group H and $C_1$-$C_4$ alkyl; or $R^7$ and $R^8$ are taken together as $CH_2CH_2CH_2CH_2$, $CH_2CH_2CH_2CH_2CH_2$, or $CH_2CH_2OCH_2CH_2$;

$R^{13}$ is selected from the group H and $C_1$-$C_3$ alkyl;

$R^{17}$ is selected from $C_1$-$C_6$ alkyl;

$R^{18}$ is selected from $C_1$-$C_6$ alkyl;

$R^{19}$ and $R^{20}$ are independently $C_1$-$C_4$ alkyl; or $R^{19}$ and $R^{20}$ are taken together as $CH_2CH_2CH_2CH_2CH_2$ or $CH_2CH_2OCH_2CH_2$;

m is 1 or 2;

n is 1 or 2; and p is 1 or 2;

wherein when Q is Q-1, then W is W-2 or W-3.

2. A compound according to claim 1 wherein:

X is O;

$X^1$ is selected from the group Cl, $SR^6$, $N(CH_3)_2$ and $OR^6$;

$X^2$ is selected from the group CN, $OR^6$, OH and $N(CH_3)_2$;

R is H;

$R^1$, $R^2$, $R^{14}$ are each independently selected from the group H, F, Cl, Br, $CF_3$, $OCF_3$, $OCF_2H$, $OCH_2CF_3$ and $OSO_2CF_3$;

$R^3$ is selected from the group $CO_2CH_3$, $CH(CH_3)_2$, $CH_3$ and phenyl optionally substituted with $R^{14}$;

$R^5$ is selected from the group H and $CH_3$;

$R^6$ is $C_1$-$C_2$ alkyl;

Y is selected from the group H, $C(O)CH_3$, $CH_3$ and $CO_2CH_3$; and m and n are 1.

3. A compound according to claim 2 wherein Q is Q-1 and W is W-2.

4. A compound according to claim 2 wherein Q is Q-1 and W is W-3.

5. A compound according to claim 2 wherein Q is Q-6 and W is W-1.

6. An arthropodicidal composition comprising a compound according to claim 1 and a carrier therefor.

7. A method for controlling arthropods comprising contacting them or their environment with an arthropodicidally effective amount of a compound according to any one of claims 1 to 3, 4 and 5.

* * * * *